(12) United States Patent
Bourke, Jr. et al.

(10) Patent No.: US 11,938,011 B2
(45) Date of Patent: Mar. 26, 2024

(54) COLOR ENHANCEMENT UTILIZING UP CONVERTERS AND/OR DOWN CONVERTERS

(71) Applicant: IMMUNOLIGHT, LLC., Detroit, MI (US)

(72) Inventors: Frederic A. Bourke, Jr., Aspen, CO (US); Harold Walder, Oak Island, NC (US)

(73) Assignee: Immunolight, LLC

( * ) Notice: Subject to any disclaimer, the term of this patent is extended or adjusted under 35 U.S.C. 154(b) by 919 days.

(21) Appl. No.: 16/915,058

(22) Filed: Jun. 29, 2020

(65) Prior Publication Data

US 2020/0323711 A1 Oct. 15, 2020

Related U.S. Application Data

(62) Division of application No. 13/204,355, filed on Aug. 5, 2011, now abandoned.

(51) Int. Cl.
*H01L 33/50* (2010.01)
*A61F 13/20* (2006.01)
(Continued)

(52) U.S. Cl.
CPC .... *A61F 13/55185* (2013.01); *A61F 13/2097* (2013.01); *A61F 13/26* (2013.01);
(Continued)

(58) Field of Classification Search
CPC ......... H01L 33/44; H01L 33/48; H01L 33/50; H01L 33/504; H01L 33/405; H10K 59/38; H10K 50/125
See application file for complete search history.

(56) References Cited

U.S. PATENT DOCUMENTS 3,922,155 A 11/1975 Broemer et al.
3,981,736 A 9/1976 Broemer et al.
(Continued)

FOREIGN PATENT DOCUMENTS

CN 1649455 A 8/2005
CN 1714134 A 12/2005
(Continued)

OTHER PUBLICATIONS

Combined Chinese Office Action and Search Report dated Jul. 3, 2014 in Patent Application No. 201180048021.5.
(Continued)

*Primary Examiner* — Matthew E. Hoban
(74) *Attorney, Agent, or Firm* — TUCKER ELLIS, L.L.P.; J. Derek Mason

(57) ABSTRACT

A light emitting composition including first color emitters and second color emitters. The first color emitters are configured to emit, upon exposure to an energy source, visible light at a target color in response to absorption of energy across a first band of wavelengths. The second color emitters are configured to emit, upon exposure to the energy source, visible light at the target color in response to absorption of energy across a second band of wavelengths. The light intensity observable at the target color is enhanced relative to reflected white light without emission from the first and second color emitters. The light emitting composition can be a part of a paint, an ink, a fabric, a thread, a road sign, a highway marking, an automobile, a boat, a plane, a reflector, a building product, a concrete product, an epoxy product, a jewelry product, colored contact lens, a candle product, a rubber product, a plastic product, or other colored surface.

258 Claims, 13 Drawing Sheets

(51) Int. Cl.
  *A61F 13/26* (2006.01)
  *A61F 13/551* (2006.01)
  *H10K 50/125* (2023.01)
  *H10K 59/38* (2023.01)

(52) U.S. Cl.
  CPC ......... *H01L 33/504* (2013.01); *H10K 50/125* (2023.02); *H10K 59/38* (2023.02); *Y10S 604/904* (2013.01); *Y10T 29/4984* (2015.01); *Y10T 29/49908* (2015.01)

(56) References Cited

U.S. PATENT DOCUMENTS

| | | |
|---|---|---|
| 4,120,730 A | 10/1978 | Trojer et al. |
| 4,283,320 A | 8/1981 | Carroll |
| 4,613,633 A | 9/1986 | Masayoshi |
| 4,705,952 A | 11/1987 | Lindmayer |
| 4,786,617 A | 11/1988 | Andrieu et al. |
| 4,789,694 A | 12/1988 | Hahn, Jr. |
| 5,034,353 A | 7/1991 | Shibuya et al. |
| 5,134,186 A | 7/1992 | Ingle et al. |
| 5,441,774 A | 8/1995 | Dutta et al. |
| 5,650,213 A | 7/1997 | Rizika et al. |
| 6,054,724 A | 4/2000 | Ogihara et al. |
| 6,104,740 A | 8/2000 | Floyd |
| 6,169,185 B1 | 1/2001 | Likavec et al. |
| 6,375,864 B1 | 4/2002 | Phillips et al. |
| 6,744,960 B2 | 6/2004 | Pelka |
| 6,896,369 B2 | 5/2005 | Streibig |
| 7,090,355 B2 | 8/2006 | Liu et al. |
| 7,468,146 B2 | 12/2008 | Andriessen |
| 7,501,092 B2 | 3/2009 | Chen |
| 7,608,237 B2 | 10/2009 | Alexandridis et al. |
| 7,615,169 B2 | 11/2009 | Strouse et al. |
| 7,645,318 B2 | 1/2010 | Anderson et al. |
| 7,682,435 B2 | 3/2010 | Mizutani et al. |
| 7,846,412 B2 | 12/2010 | Nie et al. |
| 8,221,651 B2 | 7/2012 | Murase et al. |
| 8,236,199 B2 | 8/2012 | Mahany et al. |
| 2004/0257330 A1 | 12/2004 | Minami |
| 2005/0031838 A1 | 2/2005 | Lagunowich et al. |
| 2005/0120907 A1 | 6/2005 | Aoyama et al. |
| 2005/0203495 A1 | 9/2005 | Malak |
| 2005/0265935 A1 | 12/2005 | Hollingsworth et al. |
| 2006/0083762 A1 | 4/2006 | Brun et al. |
| 2006/0165621 A1 | 6/2006 | Dubertret et al. |
| 2006/0275368 A1 | 12/2006 | Deppisch et al. |
| 2007/0274938 A1 | 11/2007 | Alfano et al. |
| 2008/0057096 A1 | 3/2008 | Ibsen |
| 2008/0277267 A1 | 11/2008 | Biberger et al. |
| 2008/0277268 A1 | 11/2008 | Layman |
| 2008/0277270 A1 | 11/2008 | Biberger et al. |
| 2009/0034055 A1 | 2/2009 | Gibson |
| 2009/0088500 A1 | 4/2009 | Nishimoto et al. |
| 2009/0095970 A1 | 4/2009 | Yen et al. |
| 2009/0159510 A1 | 6/2009 | Haushalter et al. |
| 2009/0294692 A1 | 12/2009 | Bourke, Jr. et al. |
| 2010/0023101 A1 | 1/2010 | Wallace et al. |
| 2010/0062194 A1 | 3/2010 | Sun |
| 2010/0126566 A1 | 5/2010 | Ji |
| 2010/0126567 A1 | 5/2010 | Kaufman |

FOREIGN PATENT DOCUMENTS

| | | |
|---|---|---|
| CN | 101238592 A | 8/2008 |
| FR | 2 846 647 S1 | 5/2004 |
| JP | 2010118686 * | 5/2010 |
| TW | 200950846 A1 | 12/2009 |
| WO | WO 99/52982 | 10/1999 |
| WO | WO 2004044090 A1 | 5/2004 |
| WO | WO 2009114567 A1 | 9/2009 |

OTHER PUBLICATIONS

Second Office Action issued in corresponding Chinese Patent Application No. 201180048021.5 dated Feb. 16, 2015.
International Search Report and Written Opinion of the International Searching Authority dated Feb. 10, 2012 in patent application No. PCT/US11/46709 filed Aug. 5, 2011.
Extended European Search Report dated Apr. 24, 2015 in corresponding European Patent Application No. 11815361.8.
Taiwan Office Action issued in corresponding Taiwan application No. 100128053 dated Jul. 22, 2015.
Combined Chinese Office Action and Search Report dated Feb. 28, 2017 in Patent Application No. 201510691063.0.
Yu-Lin Min, et al., "Au@$Y_2O_3$:$Eu^{3+}$ Rare Earth Oxide Hollow Sub-Microspheres with Encapsulated Gold Nanoparticles and their Optical Properties", Solid State Sciences, 11 (2009), pp. 96-101.
Office Action dated Oct. 30, 2017, in Chinese Patent Application No. 201510691063 filed Aug. 5, 2011.
Xing. Synthesis of monodisperse spherical Y2O2S:Yb,Ho upconversion nanoparticles.Solid State Communications 149 (2009) 911-914.
Jia. Uniform YVO4:Ln3+ (Ln=Eu, Dy, and Sm) nanocrystals: Solvothermal synthesis and luminescence properties. Optical Materials 31 (2009) 1032-1037.
Diaz-Torres. A New Blue, Green and Red Upconversion Emission Nanophosphor: BaZrO3:Er,Yb. Journal of Nanoscience and Nanotechnology vol. 8, 6425-6430, 2008.
Zhang. Photoluminescence of YVO4:Tm phosphor prepared by a polymerizable complex method. Solid State Communications 132 (2004) 527-531.
Pires. Yttrium oxysulfide nanosized spherical particles doped with Yb and Er or Yb and Tm: efficient materials for up-converting phosphor technology field.Journal of Alloys and Compounds 374 (2004) 181-184.
Lee. CdTe and Au quantum-dot bioconjugated super-molecules: light emission and energy transport. 2004 Al Che Annual Meeting. Austin Texas Nov. 7-12, 2004.
Yi. Colloidal LaF3:Yb,Er, LaF3:Yb,Ho and LaF3:Yb,Tm nanocrystals with multicolor upconversion fluorescence. I J. Mater. Chem., 2005, 15, 4460-4464 (Year: 2005).
Boyer. Synthesis of Colloidal Upconverting NaYF4: Er3+/Yb3+ and Tm3+/Yb3+ Monodisperse Nanocrystals. Nano Letters 2007 vol. 7, No. 3.

* cited by examiner

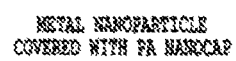 
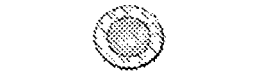  

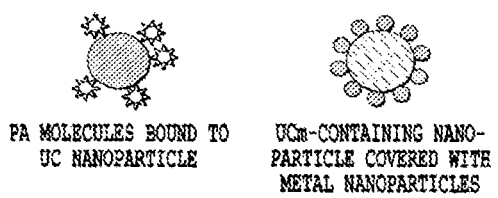
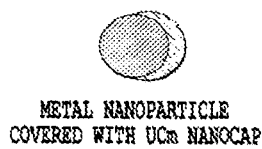 
  

Fig. 6A-A  PA molecules bound to UC nanoparticle
Fig. 6A-B  UCm-containing nanoparticle covered with metal nanoparticles
Fig. 6A-C  Metal nanoparticle covered with UCm nanocap
Fig. 6A-D  UCm-containing nanoparticle covered with metal nanocap
Fig. 6A-E  Metal nanoparticle covered with UCm nanoshell
Fig. 6A-F  UCm-containing nanoparticle covered with metal nanoshell
Fig. 6A-G  UCm-containing nanoparticle covered with metal nanoshell with protective coating layer

PLASMONICS PHOTO-ACTIVE PROBES WITH
ENERGY UPCONVERTING MATERIALS

☆ PHOTO-ACTIVE (PA) MOLECULE (PHOTOSENSITIZER)

METAL (e.g. Au, Ag)

UPCONVERTING MATERIAL (UCm)

PROTECTIVE COATING

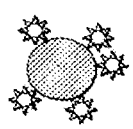

PA MOLECULES BOUND TO UC NANOPARTICLE

*Fig. 6B-A*

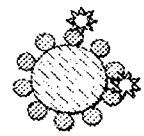

UCm-CONTAINING NANO-PARTICLE COVERED WITH METAL NANOPARTICLES

*Fig. 6B-B*

METAL NANOPARTICLE COVERED WITH UCm NANOCAP

*Fig. 6B-C*

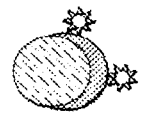

UCm-CONTAINING NANO-PARTICLE COVERED WITH METAL NANOCAP

*Fig. 6B-D*

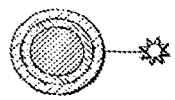

METAL NANOPARTICLE COVERED WITH DIELECTRIC LAYER AND UCm NANOSHELL

*Fig. 6B-E*

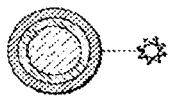

METAL NANOPARTICLE COVERED WITH DIELECTRIC LAYER AND METAL NANOSHELL

*Fig. 6B-F*

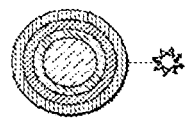

METAL NANOPARTICLE COVERED WITH DIELECTRIC LAYER AND METAL NANOSHELL WITH PROTECTIVE COATING LAYER

*Fig. 6B-G*

PLASMONICS-ACTIVE METAL STRUCTURES

METAL NANOPARTICLE

*Fig. 6C-A*

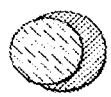

DIELECTRIC NANOPARTICLE CORE COVERED WITH METAL NANOCAP

*Fig. 6C-B*

▨ METAL 1 (e.g. Au, Ag)
▨ METAL 2 (e.g. Au, Ag)
▨ UPCONVERSION MATERIAL
▨ PROTECTIVE COATING

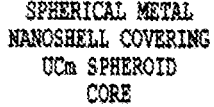

SPHERICAL METAL NANOSHELL COVERING UCm SPHEROID CORE

*Fig. 6C-C*

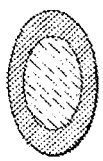

OBLATE METAL NANO-SHELL COVERING UCm SPHEROID CORE

*Fig. 6C-D*

METAL NANOPARTICLE CORE COVERED WITH UCm NANOSHELL

*Fig. 6C-E*

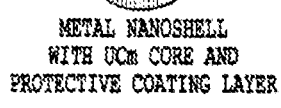

METAL NANOSHELL WITH UCm CORE AND PROTECTIVE COATING LAYER

*Fig. 6C-F*

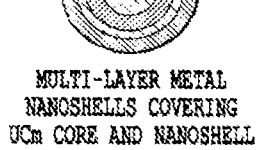

MULTI-LAYER METAL NANOSHELLS COVERING UCm CORE AND NANOSHELL

*Fig. 6C-G*

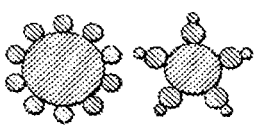

MULTI-NANO-PARTICLE STRUCTURES

*Fig. 6C-H*

METAL NANOCUBE AND NANO-TRIANGLE/NANO-PRISM

*Fig. 6C-I*

METAL CYLINDER

*Fig. 6C-J*

COLOR ENHANCEMENT UTILIZING UP CONVERTERS AND/OR DOWN CONVERTERS

CROSS REFERENCE TO RELATED APPLICATIONS

This application is a Divisional of U.S. Ser. No. 13/204,355, filed Aug. 5, 2011, pending. This application is related to and claims priority under 35 U.S.C. 119(e) to U.S. provisional patent application 61/371,549, filed Aug. 6, 2010. This application is related to U.S. provisional patent application 61/161,328, filed Mar. 18, 2009 and to U.S. provisional patent application 61/259,940, filed Nov. 10, 2009, the entire disclosures of which are hereby incorporated by reference. This application is related to U.S. Ser. No. 12/725,108, the entire disclosures of which are hereby incorporated by reference.

This application is related to Provisional Application Ser. No. 60/954,263, filed Aug. 6, 2007, and 61/030,437, filed Feb. 21, 2008, and U.S. application Ser. No. 12/059,484, filed Mar. 31, 2008, the contents of which are hereby incorporated herein by reference. This application is also related to U.S. application Ser. No. 11/935,655, filed Nov. 6, 2007; and Provisional Application Ser. No. 61/042,561, filed Apr. 4, 2008; 61/035,559, filed Mar. 11, 2008, and 61/080,140, filed Jul. 11, 2008, the entire contents of which are hereby incorporated herein by reference. This application is related to U.S. patent application Ser. No. 12/401,478 filed Mar. 10, 2009, the entire contents of which are hereby incorporated herein by reference. This application is related to U.S. patent application Ser. No. 11/935,655, filed Nov. 6, 2007, and Ser. No. 12/059,484, filed Mar. 31, 2008; U.S. patent application Ser. No. 12/389,946, filed Feb. 20, 2009; U.S. patent application Ser. No. 12/417,779, filed Apr. 3, 2009, the entire disclosures of which are hereby incorporated by reference.

BACKGROUND OF THE INVENTION

Field of the Invention

The invention relates to methods and systems for generating or enhancing light emission or reflectance from visible displays and colored surfaces so as to enhance the appearance of the visible object.

Discussion of the Background

Presently, light (i.e., electromagnetic radiation from the radio frequency through the visible to the X-ray wavelength range) is used in a number of industrial, communication, electronic, and pharmaceutical processes. Light in the infrared and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged particles, such as parts of molecules (or adjacent atoms) with high thermal energy, or electrons in atoms (or molecules).

For reference purposes, infra-red (IR) radiation just beyond the red end of the visible region; and, ultra-violet (UV) radiation has a shorter wavelength than violet light. The UV portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including W-filaments, halogen-protected W-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ ($lm/m^2$) in a certain direction per steradian (unit of solid angle) and the irradiance (illuminance) of a surface in $W/m^2$ ($lm/m^2$ or lux).

With the development of ultraviolet sources, ultraviolet radiation is being increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semi-conductor phosphors from the excitation of these phosphors from high energy sources such as, for example, X-ray irradiation.

With the development of infrared radiation sources, infra-red radiation is being increasingly utilized for communications and signaling purposes. Typically, infrared sources use broad spectrum light sources referred to as glowbars to generate a broad spectrum of light centered in the infrared range or use lasers to emit very specific infrared wavelengths. For the broad band sources, the emitted light is optically filtered to remove many, if not all, of the non-infrared frequencies.

It is generally desirable to have devices, materials, and capabilities to convert light from one frequency range to another. Down conversion has been one way to convert higher energy light to lower energy, as used in the phosphors noted above. Up conversion has also been shown where lower energy light is converted to higher energy light. Typically, this process is a multi-photon absorption process where two or more photons are used to promote an excited electronic state in a host medium which in turn radiates at a wavelength of light that has a higher energy than the energy of the incident light which promoted the multi-photon absorption process. Both down conversion and up conversion have been studied and documented in the past.

Indeed, workers have studied the phenomenon of photoluminescence and fluorescence, which is the ability of certain solids to emit light when driven or charged by an external energy source. Many well-known phosphors and fluorescors are triggered by high-energy electrons or photons and emit photons of lower energy. It has been recognized that certain infrared phosphors can convert infrared light to light in the visible range (violet through red).

The properties of light such as its radiance is particularly important in reading or display applications where the human eye has to perceive and discern temporary images or permanent images (as for example shown by road and highway signs) formed with visible light. Televisions, computer monitors, displays, and signs use a cathode ray technology (CRT) technology where high energy electrons impinge on phosphors that emit visible light. Televisions, computer monitors, displays, and signs more recently have used liquid crystal display or plasma display technology to generate visible images discernable to the human eye.

In these and other reading or display applications, attempts have been made to develop displays with relatively high contrast images while minimizing the amount of broadband light emitted or reflected from a display, which may detract from the contrast of the image displayed.

SUMMARY OF THE INVENTION

In one embodiment, there is provided a light emitting composition including first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters.

In another embodiment, there is provided a paint including a pigment and a mixture of color-emitters included in the pigment. The mixture includes first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters.

In another embodiment, there is provided an ink including a dye and a mixture of color-emitters included in the dye. The mixture includes first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters.

In another embodiment, there is provided a display including a color filter or a color reflective surface and a mixture of color-emitters included in the color filter or the color reflective surface. The mixture includes first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters.

In another embodiment, there is provided a method for enhancing visible light emission from a surface. The method provides on the surface a mixture of color emitters including first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters. The method exposes the color emitters to an energy source. The method emits the visible light at a first wavelength $\lambda_1$ by conversion of a part of the energy into the visible light at the first wavelength $\lambda_1$.

In another embodiment, there is provided a method for enhancing visible light emission from a paint. The method provides in the paint or in a vicinity of a surface of the paint a mixture of color emitters including first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters. The method exposes the color emitters to an energy source. The method emits the visible light at a first wavelength $\lambda_1$ by conversion of a part of the energy into the visible light at the first wavelength $\lambda_1$.

In another embodiment, there is provided a method for enhancing visible light emission from an ink. The method provides in the ink a mixture of color emitters including first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters. The method exposes the color emitters to an energy source. The method emits the visible light at a first wavelength $\lambda_1$ by conversion of a part of the energy into the visible light at the first wavelength $\lambda_1$.

In another embodiment, there is provided a method for enhancing visible light emission from a display. The method provides on a color filter or a color reflective surface of the display a mixture of color emitters including first color emitters configured to emit, upon exposure to an energy source, visible light at a target color in response to absorption of energy across a first band of wavelengths and including second color emitters configured to emit, upon exposure to the energy source, visible light at the target color in response to absorption of energy across a second band of wavelengths. The light intensity observable at the target color is enhanced relative to reflected white light without emission from the first and second color emitters. The method exposes the color emitters to an energy source. The method emits the visible light at a first wavelength $\lambda_1$ by conversion of a part of the energy into the visible light at the first wavelength $\lambda_1$.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 4A is a schematic illustration of various upconverter structures of the invention;

FIG. 6A is a schematic illustration of other various upconverter structures of the invention;

FIG. 6B is another schematic illustration of other various upconverter structures of the invention;

FIG. 6C is a schematic illustration of plasmonics-active upconverter structures of the invention;

DETAILED DESCRIPTION OF THE INVENTION

Figure 1:
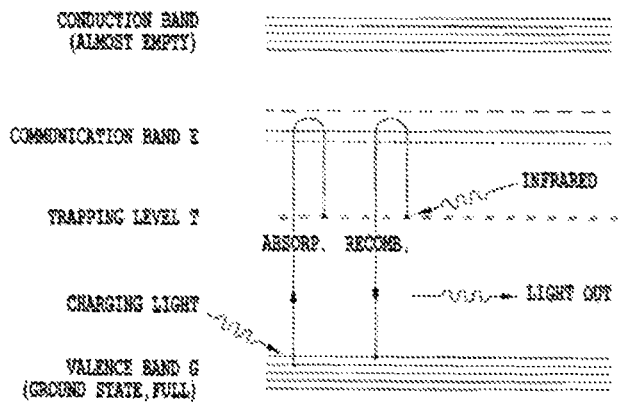
FIG. 1 is an energy diagram of an infrared phosphor system.

This invention is directed to methods and systems for producing electromagnetic radiation having desirable frequency windows (at least one frequency within a desirable frequency range) from other electromagnetic radiation having lower or higher frequency ranges using up converting transitional media or down converting transitional media as the case may apply.

In various embodiments of the invention, there are provided systems and methods for up conversion of light e.g., from the IR regime into visible electromagnetic radiation and for down conversion of light e.g., from the UV range into visible electromagnetic radiation. The invention in various embodiments up converts energy, preferably light in the visible spectrum and/or downLets also include other areas of the electromagnetic spectrum, from radio to gamma converts energy, preferably light in the visible spectrum. The invention encompasses a variety of applications where the up and down conversions are conducted to enhance the color of the object being displayed. These application areas can include paints on signs, walls, cars, buildings, boats, airplanes. These application areas can include display monitors, computer monitors, telephone displays, watch dials, instrument dials to name but a few.

Among various materials, luminescent nanoparticles have attracted increasing technological and industrial interest. In the context of the invention, nanoparticle refers to a particle having a size less than one micron. While the description of the invention describes specific examples using nanoparticles, the invention in many embodiments is not limited to particles having a size less than one micron. However, in many of the embodiments, the size range of less than one micron, and especially less than 100 nm produces properties of special interest such as for example emission lifetime luminescence quenching, luminescent quantum efficiency, and concentration quenching and such as for example diffusion, penetration, and dispersion into mediums where larger size particles would not migrate.

The invention in various embodiments can use a wide variety of down conversion materials (or mixtures of down converters) to enhance a particular color of light observable from reflective material or surface. These down conversion materials can include quantum dots, semiconductor materials, alloys of semiconductor materials, scintillation and phosphor materials, materials that exhibit X-ray excited luminescence (XEOL), organic solids, metal complexes, inorganic solids, crystals, rare earth materials (lanthanides), polymers, scintillators, phosphor materials, etc., and materials that exhibit excitonic properties. Accordingly, the down conversion materials to enhance color emission can convert energy from one of ultraviolet light, x-rays, and high energy particles to visible light. The down conversion materials to enhance color emission can convert energy from higher energy visible light to lower energy visible light.

In one embodiment of the invention, a quantum dot mixture can be used for the multiple nanoparticles. Quantum dots are in general nanometer size particles whose energy states in the material of the quantum dot are dependent on the size of the quantum dot. For example, quantum dots are known to be semiconductors whose conducting characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. In fluorescent dye applications, this equates to higher frequencies of light emitted after excitation of the dot as the crystal size grows smaller, resulting in a color shift from red to blue in the light emitted. Quantum dots represent one way to down convert ultraviolet light of the spectrum to a targeted color emission, such as for example a green light emission. Quantum dots represent one way to down convert blue light of the spectrum to a targeted color emission, such as for example a green light emission.

Specifically, in one embodiment of the invention, a quantum dot mixture (QDM) coating can be deposited using CVD and or sol-gel techniques using standard precipitation techniques. The QDM coating can be made of a silicate structure that does not diminish UV output. Within the silicate family, silica ($SiO_2$) is suitable since it maximizes UV transmission through the coating. The coating can further include a second layer of a biocompatible glass. Such bio-compatible glass and glass ceramic compositions can contain calcium, a lanthanide or yttrium, silicon, phosphorus and oxygen. Other biocompatible materials and techniques are described in the following patents which are incorporated herein in their entirety: U.S. Pat. Nos. 5,034,353; 4,786,617; 3,981,736; 3,922,155; 4,120,730; and U.S. Pat. Appl. Nos. 2008/0057096; 2006/0275368; and 2010/0023101.

Further, the down conversion materials for the invention described here can be coated with insulator materials such as for example silica which will reduce the likelihood of any chemical interaction between the luminescent particles and the medium the particles are included therein. For biocompatible applications of inorganic nanoparticles, one of the major limiting factors is their toxicity. Generally speaking, all semiconductor nanoparticles are more or less toxic. For biocompatible applications, nanoparticles with toxicity as low as possible are desirable or else the nanoparticles have to remain separated from the medium. Pure $TiO_2$, ZnO, and $Fe_2O_3$ are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. Other suitable down conversion materials which would seem the most biocompatible are zinc sulfide, ZnS: $Mn^{2+}$, ferric oxide, titanium oxide, zinc oxide, zinc oxide containing small amounts of $Al_2O_3$ and AgI nanoclusters encapsulated in zeolite. For non-medical applications, where toxicity may not be as critical a concern, the following materials (as well as those listed elsewhere) are considered suitable: lanthanum and gadolinium oxyhalides activated with thulium; $Er^{3+}$ doped $BaTiO_3$ nanoparticles, $Yb^{3+}$ doped $CsMnCl_3$ and $RbMnCl_3$, $BaFBr:Eu^{2+}$ nanoparticles, Cesium Iodine, Bismuth Germanate, Cadmium Tungstate, and CsBr doped with divalent Eu.

In various embodiments of the invention, the following luminescent polymers are also suitable as conversion materials: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

In various embodiments of the invention, the following particles can be used similar to that detailed in U.S. Pat. No. 7,090,355, the entire contents of which are incorporated herein by reference. For down-conversion, the following materials can be used. Inorganic or ceramic phosphors or nano-particles, including but not limited to metal oxides, metal halides, metal chalcogenides (e.g. metal sulfides), or their hybrids, such as metal oxo-halides, metal oxo-chalcoginides. Laser dyes and small organic molecules, and fluorescent organic polymers. Semiconductor nano-particles, such as II-VI or III-V compound semiconductors, e.g. fluorescent quantum dots. Organometallic molecules including at least a metal center such as rare earth elements (e.g. Eu, Tb, Ce, Er, Tm, Pr, Ho) and transitional metal elements such as Cr, Mn, Zn, Ir, Ru, V, and main group elements such as B, Al, Ga, etc. The metal elements are chemically bonded to organic groups to prevent the quenching of the fluorescence from the hosts or solvents. Phosphors can be used including the Garnet series of phosphors: $(Y_m A_{1-m})_3 (Al_n B_{1-n})_5 O_{12}$, doped with Ce; where $0 \leq m$, $n \leq 1$, where A includes other rare earth elements, B includes B, Ga. In addition, phosphors containing metal silicates, metal borates, metal phosphates, and metal aluminates hosts can be used. In addition, nano-particulates phosphors containing common rare earth elements (e.g. Eu, Tb, Ce, Dy, Er, Pr, Tm) and transitional or main group elements (e.g. Mn, Cr, Ti, Ag, Cu, Zn, Bi, Pb, Sn, Tl) as the fluorescent activators, can be used. Materials such as Ca, Zn, Cd in tungstates, metal vanadates, ZnO, etc. can be used.

The commercial laser dyes obtained from several laser dye vendors, including Lambda Physik, and Exciton, etc can be used. A partial list of the preferred laser dye classes includes: Pyrromethene, Coumarin, Rhodamine, Fluorescein, other aromatic hydrocarbons and their derivatives, etc. In addition, there are many polymers containing unsaturated carbon-carbon bonds, which also serve as fluorescent materials and find many optical and fluorescent applications. For example, MEH-PPV, PPV, etc have been used in optoelectronic devices, such as polymer light emitting diodes (PLED). Such fluorescent polymers can be used directly as the fluorescent layer of the transparent 2-D display screen.

As noted above, semiconductor nanoparticles (e.g., quantum dots) can be used. The terms "semiconductor nanoparticles," in the art refers to an inorganic crystallite between 1 nm and 1000 nm in diameter, preferably between 2 nm to 50 nm. A semiconductor nano-particle is capable of emitting electromagnetic radiation upon excitation (i.e., the semiconductor nano-particle is luminescent). The nanoparticle can be either a homogeneous nano-crystal, or comprises of multiple shells. For example, the nanoparticle can include a "core" of one or more first semiconductor materials, and may be surrounded by a "shell" of a second semiconductor material. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

Fluorescent organometallic molecules containing rare earth or transitional element cations can be used for down conversion. Such molecules include a metal center of rare earth elements including Eu, Tb, Er, Tm, Ce protected with organic chelating groups. The metal center may also include transitional elements such as Zn, Mn, Cr, Ir, etc and main group elements such as B, Al, Ga. Such organometallic molecules can readily dissolved in liquid or transparent solid host media. Some examples of such fluorescent organometallic molecules include: 1. Tris(dibenzoylmethane)mono(phenanthroline)europium(III); 2. Tris(8-hydroxyquinoline)erbium; 3. Tris(1-phenyl-3-methyl-4-(2,2-dimethylpropan-1-oyl)pyrazolin-5-one)terbium(III); 4. Bis(2-methyl-8-hydroxyquinolato)zinc; 5. Diphenylborane-8-hydroxyquinolate.

Specific examples of down-converting particles for red emission include those discussed above and europium complexes such as those described in JP Laid-open Patent Publication (Kokai) No. 2003-26969, constructed such that β-diketone ligand is coordinated to europium forming an europium complex capable of emitting red fluorescence. Other specific examples of the rare earth element complexes include complexes include lanthanum (Ln), europium (Eu), terbium (Tb), and gadolinium (Gd) and combinations thereof. An europium (Eu) complex is capable of emitting red fluorescence when irradiated with ultraviolet rays having a wavelength ranging from 365 nm to 410 nm. Terbium (Tb) is capable of emitting green fluorescence when irradiated with ultraviolet rays having a wavelength of 365 nm.

In other down-conversion embodiments, light emitting particles which emit red light may include europium, light emitting particles which emit green light may include Terbium, and light emitting particles which emit blue or yellow light may include cerium (and/or thulium). In up-conversion embodiments, light emitting particles which emit red light may include praseodymium, light emitting particles which emit green light may include erbium, and light emitting particles which emit blue light may include thulium. In embodiments, light emitting particles can be fluorescent molecules that emit different colors (e.g. red, green, and blue). In embodiments, light emitting particles can be included in pure organic or organometallic dyes.

In addition to the combinations of rare earth complexes, such as a combination of a europium complex and a terbium complex, it is also possible employ a combination of a europium complex and a green-emitting fluorescent substance which is not a complex, or a combination of a terbium complex and a red-emitting fluorescent substance which is not a complex.

Other down converters include for example ZnS, PbS, $SbS_3$, $MoS_2$, PbTe, PbSe, BeO, MgO. $Li_2CO_3$, $Ca(OH)_2$, $MoO_3$, $SiO_2$, $Al_2O_3$, $TeO_2$, $SnO_2$, KBr, KCl, and NaCl. These materials can include dopants to tailor the emission properties, as noted above. Examples of doped (or alloyed) glass systems suitable for the include $Y_2O_3$:Gd, $Y_2O_3$:Dy, $Y_2O_3$:Tb, $Y_2O_3$:Ho, $Y_2O_3$:Er, $Y_2O_3$:Tm, $Gd_2O_3$:Eu, $Y_2O_2S$:Pr, $Y_2O_2S$:Sm, $Y_2O_2S$:Eu, $Y_2O_2S$:Tb, $Y_2O_2S$:Ho, $Y_2O_2S$:Er, $Y_2O_2S$:Dy, $Y_2O_2S$:Tm, ZnS:Ag:Cl (blue), ZnS:Cu:Al (green), $Y_2O_2S$:Eu (red), $Y_2O_3$:Eu (red), $YVO_4$:Eu (red), and $Zn_2SiO_4$:Mn (green).

Alternatively, quantum dots (as described above) can be used to tailor the down conversion process. As described in U.S. Pat. No. 6,744,960 (the entire contents of which are incorporated by reference), different size quantum dots produce different color emissions. In that work and applicable to this invention, quantum dots can comprise various materials including semiconductors such as zinc selenide (ZnSe), cadmium selenide (CdSe), cadmium sulfide (CdS), indium arsenide (InAs), and indium phosphide (InP). Another material that may suitably be employed is titanium dioxide ($TiO_2$). The size of the particle, i.e., the quantum dot 18, may range from about 2 to 10 nm. Since the size of these particles is so small, quantum physics governs many of the electrical and optical properties of the quantum dot. One such result of the application of quantum mechanics to the quantum dot 18 is that quantum dots absorb a broad spectrum of optical wavelengths and re-emit radiation having a wavelength that is longer than the wavelength of the absorbed light. The wavelength of the emitted light is governed by the size of the quantum dot. For example, CdSe quantum dots 5.0 nm in diameter emit radiation having a narrow spectral distribution centered about 625 nm while quantum dots 18 including CdSe 2.2 nm in size emit light having a center wavelength of about 500 nm. Semiconductor quantum dots comprising CdSe, InP, and InAs, can emit radiation having center wavelengths in the range between 400 nm to about 1.5 μm. Titanium dioxide $TiO_2$ also emits in this range. The linewidth of the emission, i.e., full-width half-maximum (FWHM), for these semiconductor materials may range from about 20 to 30 nm. To produce this narrowband emission, quantum dots simply need to absorb light having wavelengths shorter than the wavelength of the light emitted by the dots. For example, for 5.0 nm diameter CdSe quantum dots light having wavelengths shorter than about 625 nm is absorbed to produce emission at about 625 nm while for 2.2 nm quantum dots comprising CdSe light having wavelengths smaller than about 500 nm is absorbed and re-emitted at about 500 nm. In practice, however, the excitation or pump radiation is at least about 50 nanometers shorter than the emitted radiation.

With regard more specifically to down converters suitable for the invention, U.S. Pat. No. 4,705,952 (the contents of which are hereby incorporated herein by reference) describes an infrared-triggered phosphor that stores energy in the form of visible light of a first wavelength and released energy in the form of visible light of a second wavelength when triggered by infrared light. The phosphors in U.S. Pat. No. 4,705,952 were compositions of alkaline earth metal sulfides, rare earth dopants, and fusible salts. The phosphors in U.S. Pat. No. 4,705,952 were more specifically phosphors made from strontium sulfide, barium sulfide and mixtures thereof; including a dopant from the rare earth series and europium oxide, and mixtures thereof; and including a fusible salt of fluorides, chlorides, bromides, and iodides of lithium, sodium, potassium, cesium, magnesium, calcium, strontium, and barium, and mixtures thereof. The materials described in U.S. Pat. No. 4,705,952 are useful in various embodiments of the invention.

In other embodiments of the invention, the down converters (or mixtures of down converters) can include $Y_2O_3$:Li. Sun et al "Luminescent properties of Li+ doped nano-sized $Y_2O_3$:Eu," Solid State Comm. 119 (2001) 393-396 (the entire contents of which are incorporated herein by reference) describe such materials. Hou et al "Luminescent properties nano-sized $Y_2O_3$:Eu fabricated by co-precipitation method," Journal of Alloys and Compounds, vol. 494, issue 1-2, 2 Apr. 2010, pages 382-385 (the entire contents of which are incorporated herein by reference) describe that nano-sized yttria ($Y_2O_3$) powders have been successfully synthesized by a co-precipitation method. The powders were well crystallized, and the grains were almost spherical with good dispersibility. The quenching concentration of $Eu^{3+}$ ions is 9 mol % which is much higher than micro-scaled powders. The incorporation of Li+ ions greatly improved the luminescence intensity. The highest emission intensity was observed with 4 mol % Li+ doped $Y_2O_3$:Eu powder (($Y_{0.87}Eu_{0.09}Li_{0.04})_2O_3$) and the fluorescence intensity was increased by as much as 79%. Yi et al "Improved cathodoluminescent characteristics of $Y_2O_3$:$Eu^{3+}$ thin films by Li-doping," Appl. Phys. A 87, 667-671 (2007) (the entire contents of which are incorporated herein by reference) describe cathodoluminescent spectra for both $Y_2O_3$:$Eu^{3+}$ and Li-doped $Y_2O_3$:$Eu^{3+}$ films and methods for making these materials.

These references show that Li-doped $Y_2O_3$ materials can be used as down converters or in the mixtures of down converters and therefore would be acceptable materials for the color enhancing mixtures of the invention. This material is an especially suited material for x-ray stimulated emissions in the ultraviolet to violet region of the light spectrum.

The invention in other embodiments use a wide variety of up conversion materials (or mixtures of up converters) to enhance a particular color of light observable from reflective material or surface. These up conversion materials can include similar materials as discussed above with regard to down conversion but typically included doped or impurity states in a host crystal that provide a mechanism for up conversion pumping. Accordingly, the up conversion materials to enhance color emission can convert energy from one of near infrared, infrared, and microwave irradiation. The upconversion materials to enhance color emission can convert energy from lower energy visible light to higher energy visible light.

Reference will now be made in detail to a number of embodiments of the invention, examples of which are illustrated in the accompanying drawings, in which like reference characters refer to corresponding elements.

The energy relations present in the upconverter in U.S. Pat. No. 4,705,952 are shown in the energy diagram of FIG. 1, where energy states E and T are introduced by two selected impurities. Excitation of these states by absorption of light or energy having a minimum energy of E minus G will cause electrons to be raised to the band at energy state E. When charging illumination ceases, many of the excited electrons will fall to energy state T and remain trapped there. The trapping phenomenon is illustrated at the left of FIG. 1. Later exposure to triggering illumination of infrared light can supply E minus T energies, permitting the infrared-triggered phosphor in excited state T to transition to level E, as shown at the right of FIG. 1. A photon is emitted during this transition process. The resulting light emission is characterized by a wavelength associated with E minus G.

If the depth of the trap is several times higher than the thermal energy, more than 99% of the electrons are in the electron-hole trap. If the depth of the traps is about 1 eV, then in the dark, most of the traps are filled, band E is almost empty and electron hole recombination is negligible. Here the choice of appropriate phosphors presents an occurrence where the charging light (of an energy higher than visible light) stores itself to be emitted upon exposure to infrared light (of an energy lower than visible light) to thereby emit visible light.

Considerable effort has gone into the synthesis of luminescent nanoparticles, and numerous investigations of their optical properties have been performed. The synthesis of oxide nanoparticles such as those that are based on lanthanides have been achieved by a number of processes including solid-gel (sol-gel) techniques, gas phase condensation or colloidal chemical methods. While efforts to make concentrated colloidal solutions of highly uniform size luminescent nanoparticles have met with some technical difficulties, synthesis of useful amounts of some 5 nanometer sized lanthanide doped oxides have been achieved as shown in a paper by Bazzi et al entitled *Synthesis and luminescent properties of sub 5-nm lanthanide oxide particles*, in the Journal of Luminescence 102 (2003) pages 445-450, the entire contents of which are incorporated herein by reference. The work by Bazzi et al concentrated on understanding the properties on lanthanide oxide nanonparticles with an emphasis on the microstructural properties and optical emission properties (i.e. concentrated on the fluorescence and down conversion properties of these materials). Nevertheless, the materials described by Bazzi et al are useful in various embodiments of the invention.

The present inventors have realized that such upconversion materials can be used in various ways to enhance visible light emission by way of conversion of infrared light from a solar spectrum (as in daylight exposure) or a black body spectrum (as in an incandescent lamp). In one example to be described below, a nanoparticle of a lanthanide doped oxide can be excited with near infrared laser light such as 980 nm and 808 nm to produce visible light in different parts of the red, green, blue spectrum depending on the dopant trivalent rare earth ion(s) chosen, their concentration, and the host lattice.

Other work reported by Suyver et al in *Upconversion spectroscopy and properties of NaYF$_4$ doped with Er$^{3+}$, Tm$^{3+}$ and or Yb$^{3+}$*, in Journal of Luminescence 117 (2006) pages 1-12, the entire contents of which are incorporated herein by reference, recognizes in the NaYF$_4$ material system upconversion properties. Yet, there is no discussion as to the quality or quantity of upconverted light to even suggest that the amount produced could be useful for display or color enhancing applications The materials described by Suyver et al are useful in various embodiments of the invention.

Figure 2:
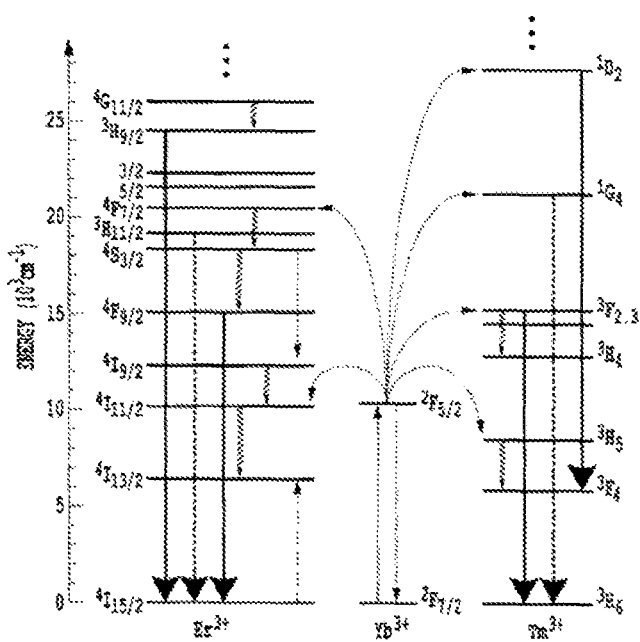
FIG. 2 is a schematic energy level diagram showing upconversion excitation and visible emissions schemes for $Er^{3+}$, $Tm^{3+}$ and or $Yb^{3+}$ ions.

FIG. 2 is a schematic reproduced from Suyver et al showing a schematic energy level diagram of upconversion excitation and visible emissions schemes for Er$^{3+}$, Tm$^{3+}$ and or Yb$^{3+}$ ions. Full, dotted, dashed, and curly arrows indicate respectively radiative, non-radiative energy transfer, cross relaxation and other relaxation processes.

The lanthanide doped oxides differ from more traditional multi-photon up conversion processes where the absorption of, for example, two photons is needed in a simultaneous event to promote an electron from a valence state directly into an upper level conduction band state where relaxation across the band gap of the material produces fluorescence. Here, the co-doping produces states in the band gap of the NaYF$_4$ such that the Yb$^{3+}$ ion has an energy state at $^2F_{5/2}$ pumpable by a single photon event and from which other single photon absorption events can populate even higher states. Once in this exited state, transitions to higher energy radiative states are possible, from which light emission will be at a higher energy than that of the incident light pumping the $^2F_{5/2}$ energy state. In other words, the energy state at $^2F_{5/2}$ of the Yb$^{3+}$ ion is the state that absorbs 980 nm light permitting a population build up serving as the basis for the transitions to the higher energy states such as the $^4F_{7/2}$ energy state. Here, transitions from the $^4F_{7/2}$ energy state produce visible emissions.

Figure 3:
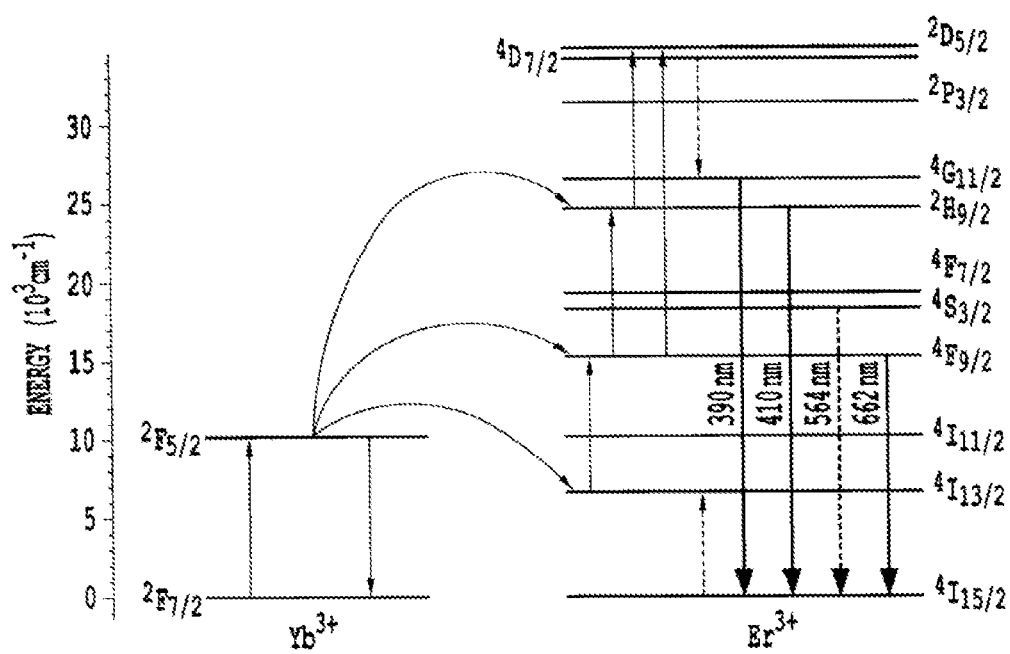
FIG. 3 is an energy diagram showing energy states for a four-photon upconversion process in $Y_2O_3$ nanocrystals.

Chen et al have described a four-photon upconversion in *Four-photon upconversion induced by infrared diode laser excitation in rare-earth-ion-doped Y$_2$O$_3$ nanocrystals*, Chemical Physics Letters, 448 (2007) pp. 127-131 In that paper, emissions at 390 nm and at 409 nm were associated with a four-photon upconversion process in the Y$_2$O$_3$ nanocrystals. FIG. 3 reproduced from Chen et al shows a ladder of states by which an infrared light source can progressively pump until the $^4D_{7/2}$ state is reached. From this upper state, transitions downward in energy occur until the $^4G_{1/2}$ state is reached, where a transition downward in energy emits a 390 nm photon. The materials described by Chen et al are useful in various embodiments of the invention.

The transitions from 390 nm, 410 nm, 564 nm, and 662 nm represent potential emissions across the visible spectrum that could for example enhance white light emission upon absorption of light or energy from an IR light source, or depending on the relative strengths for each of these emissions could be used to enhance a particular color emission upon absorption of light or energy from an IR light source.

U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 (including the ZnS as well as Er$^{3+}$ doped BaTiO$_3$ nanoparticles and Yb$^{3+}$ doped CsMnCl$_3$) are suitable in various embodiments of the invention.

Further, materials specified for up conversion in the invention include CdTe, CdSe, ZnO, CdS, Y$_2$O$_3$, MgS, CaS, SrS and BaS. Such up conversion materials may be any semiconductor and more specifically, but not by way of limitation, sulfide, telluride, selenide, and oxide semiconductors and their nanoparticles, such as $Zn_{1-x}Mn_xS_y$, $Zn_{1-x}Mn_xSe_y$, $Zn_{1-x}Mn_xTe_y$, $Cd_{1-x}MnS_y$, $Cd_{1-x}MnSe_y$, $Cd_{1-x}Mn_xTe_y$, $Pb_{1-x}Mn_xS_y$, $Pb_{1-x}MnSe_y$, $Pb_{1-x}Mn_xTe_y$, $Mg_{1-x}MnS_y$, $Ca_{1-x}Mn_xS_y$, $Ba_{1-x}Mn_xS_y$ and $Sr_{1-x}$, etc. (wherein, $0<x\leq1$, and $0<y\leq1$). Complex compounds of the above-described semiconductors are also contemplated for use in the invention—e.g. $(M_{1-z}N_z)_{1-x}Mn_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, Se, Te, O; 0<x≤1, 0<y≤1, 0<z≤1). Two examples of such complex compounds are $Zn_{0.4}Cd_{0.4}Mn_{0.2}S$ and $Zn_{0.9}Mn_{0.1}S_{0.8}Se_{0.2}$. Additional conversion materials include insulating and nonconducting materials such as $BaF_2$, BaFBr, and $BaTiO_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: $(M_{1-z}N_z)_{1-x}(Mn_qR_{1-q})_xA_{1-y}B_y$ (M=Zn, Cd, Pb, Ca, Ba, Sr, Mg; N=Zn, Cd, Pb, Ca, Ba, Sr, Mg; A=S, Se, Te, O; B=S, . . . 0<z≤1, o<q≤1).

Some nanoparticles such as $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$ are known in the art to function for both down-conversion luminescence and upconversion luminescence and would be suitable for the invention. In up-conversion embodiments, light emitting particles which emit red light may include praseodymium, light emitting particles which emit green light may include erbium, and light emitting particles which emit blue light may include thulium.

In general, the upconversion process generally requires one of more rare-earth dopants, such as Er, Eu, Yb, Tm, Nd, Tb, Ce, Y, U, Pr, La, Gd and other rare-earth species or a combination thereof, doped into a dielectric crystal (of any size >0.1 nm), including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$, where incident radiation is at longer wavelength than emissive radiation from the crystal. The wavelength emitted in based entirely on the dopant ion(s) chosen and their associated and relative contration in the host crystal. For the example of upconversion in a $Y_2O_3$ host crystal, to achieve a blue emission (~450-480 nm) one could synthesize [$Y_2O_3$; Yb (3%), Tm (0.2%)], where the Yb and Tm are the percentages doped in the crystal relative to the Y atoms being 100%. Likewise, typical green upconversion materials are [$Y_2O_3$; Yb (5%), Ho (1%)] and [$Y_2O_3$; Yb (2%), Er (1%)], and typical red upconversion materials are [$Y_2O_3$; Yb (10%), Er (1%)] and [$Y_2O_3$; Yb (5%), Eu (1%)]. The concentrations of dopants relative to each other and the crystal matrix must be tuned for every combination, and there are multiple ways to achieve multiple colors from even the same dopants.

Up-conversion of red light with a wavelength of about 650 nm in $Tm^{3+}$ doped flourozirconate glasses can be used in the invention to produce blue light. In this system, the blue light consists of two emission bands; one at 450 nm which is ascribed to the 1D2→3H4 transition, the others at 475 nm is ascribed to the 1G4→3H6 transition. The emission intensities of both bands have been observed by others to vary quadratically with the excitation power. For glasses with a $Tm^{3+}$ concentration of 0.2 mol % and greater, cross-relaxation processes occur which decrease the up-conversion efficiency.

The emission of visible light upon excitation in the near-infrared (NIR) has been observed in optically clear colloidal solutions of $LuPO_4:Yb^{3+}$, $Tm^{3+}$, and $YbPO_4:Er^{3+}$ nanocrystals in chloroform. Excitation at 975 nm has been shown by others to produce visible luminescence in the blue, green, or red spectral regions.

Tellurium and germanium oxides (tellurites and germinates) are also suitable upconverters. These glasses can be doped with Tm, Yb, Ho, Er, Pr, for example.

$Yb^{3+}$ doped $BaZrO_3$ is also suitable for upconversion. $Er^{3+}$ and/or $Tm^{3+}$ doping is also suitable for tailoring the emission wavelengths.

In another embodiment, $Nd^{3+}:Cs_2NaGdCl_6$ and $Nd^{3+}$, $Yb^{3+}:Cs_2NaGdCl_6$ polycrystalline powder samples prepared by Morss method have been reported to be up converters and are suitable for the present invention. These materials, under 785 nm irradiation, have shown upconversion emissions near 538 nm (Green), 603 nm (Orange), and 675 nm (Red) were observed and assigned to 4G7/2→4I9/2, (4G7/2→4I11/2; 4G5/2→4I9/2), and (4G7/2→4I13/2; 4G5/2→4I11/2), respectively.

In another embodiment, $Nd^{3+}$ and $Ho^{3+}$ co-doped-based $ZrF_4$ fluoride glasses under 800 nm excitation have been reported to be up converters and are suitable for the present invention. Among the up-conversion luminescences for the $ZrF_4$ fluoride glasses, the green emission was seen to be extremely strong and the blue and red emission intensities were very weak.

In another embodiment, $Tm^{3+}/Yb^{3+}$-codoped $TeO_2$—$Ga_2O_3$—$R_2O$ (R=Li, Na, K) glasses have been reported to be up converters and are suitable for the present invention. These materials, under excitation at 977 nm, showed intense blue upconversion emission centered at 476 nm along with a weak red emission at 650 nm.

In another embodiment, metal-to-ligand charge transfer (MLCT) transition in $[Ru(dmb)_3]^{2+}$ (dmb=4,4'-dimethyl-2, 2'-bipyridine) in the presence of anthracene or 9,10-diphenylanthracene have been reported to be up converters and are suitable for the present invention. Upconverted singlet fluorescence resulting from triplet-triplet annihilation at low excitation power has been reported. In particular 9,10-diphenylanthracene (DPA) (substituted for anthracene) showed higher efficiencies for upconversion. In these experiments, workers with this material system assumed that DPA's increased singlet fluorescence quantum yield (=0.95) relative to anthracene (=0.27)7. This work lead to an approximate 24.4±6.1 enhancement of green-to-blue light upconversion permitting direct visualization of the process at low excitation power, for example by a commercial green laser pointer ($\lambda_{ex}$=532 nm, <5 mW peak power).

FIG. 4A is a schematic of a depiction of an upconverter or a down converter material (i.e., a photoactive material) according to one embodiment of the invention.

FIG. 4A shows a number of structural configurations for placement of a dielectric core upconverter or a down converter material (which is of a nanometer sized scale) in proximity to a metal shell. Incident light at a wavelength $\lambda_1$ interacts with the upconverting dielectric core. The interaction of light $\lambda_1$ with the dielectric core produces a secondary emission at a frequency $\lambda_2$ which has a shorter wavelength than $\lambda_1$ and accordingly has a higher energy than $\lambda_1$. While the exact physical mechanisms for the upconversion may depend on the particular upconversion material and process being used in a particular application, for the purposes for discussion and illustration, the following explanation is offered.

In the context of FIG. 4A, when a wavelength $\lambda_1$ interacts with a dielectric material core, three separate processes are well understood for the upconversion process involving trivalent rare earth ions. These three processes are:
1) excited state absorption whereby two photons are absorbed sequentially by the same ion to excite and populate one or more states;
2) energy transfer upconversion which is a transfer of excitation from one ion to another already in an excited state; and 3) a cooperative process of multiphotons where two nearby ions in excited states are emitting collectively from a virtual state.

Regardless of which one of these processes is occurring between the chosen ion(s) and the host lattice, the end result is a photon of energy greater than the excitation energy being emitted from the host lattice for the upconversion process.

Therefore, the particular ion being activated (whether it be a dopant ion or a host ion of a lattice such as in the neodymium oxide) will be chosen based on the host material being processed, in order that the dopant ion or the host ion in the dielectric core provide ion states which are pumpable by a NIR source to generate the resultant emission $\lambda_2$.

Hence, the invention in one embodiment provides an upconversion or a down conversion system including a nanoparticle configured, upon exposure to a first wavelength $\lambda_1$ of radiation, to generate a second wavelength $\lambda_2$ of radiation having an energy higher or lower than the first wavelength $\lambda_1$. The system can include a metallic structure disposed in relation to the nanoparticle (e.g. a metallic shell covering a fraction of the nanoparticle). The system may include a receptor disposed in the medium in proximity to the nanoparticle. The receptor upon activation by the second wavelength $\lambda_2$ may itself fluoresce producing visible light. In one embodiment of the invention, a physical characteristic of metallic structure (such as those described above and below in the drawings) is set to a value where a surface plasmon resonance in the metallic structure resonates at a frequency which provides spectral overlap with either the first wavelength $\lambda_1$ or the second wavelength $\lambda_2$.

Within the context of the invention, the term "physical characteristic" of the metallic shell or core can relate to any characteristic of the metal itself or the shell or core dimensions or shape which affects the surface plasmon resonance frequency. Such physical characteristics can include, but are not limited to, a conductivity, a radial dimension, a chemical composition or a crystalline state of the metal shell or core.

In various embodiments, the metallic structures can be a metallic shell encapsulating at least a fraction of the nanoparticle in the metallic shell wherein a conductivity, a radial dimension, or a crystalline state of the metallic shell sets the surface plasmon resonance in the metallic structure to resonate at a frequency which provides spectral overlap with either the first wavelength $\lambda_1$ or the second wavelength $\lambda_2$. In various embodiments, the metallic structures can be a multi-layer metallic shell encapsulating at least a fraction of the nanoparticle in the metallic shell wherein a conductivity, a radial dimension, or a crystalline state of the metallic shell sets the surface plasmon resonance in the metallic structure to resonate at the first wavelength $\lambda_1$ and the second wavelength $\lambda_2$. This capability permits radiation at $\lambda_1$ and $\lambda_2$ to be amplified.

In various embodiments, the metallic structures can be a metallic particle existing in one or more multiple structures. These multiple structures can have a variety of shapes including for example sphere, spheroid, rod, cube, triangle, pyramid, pillar, crescent, tetrahedral shape, star or combination thereof disposed adjacent the nanoparticle wherein a conductivity, a dimension (e.g. a lateral dimension or a thickness), or a crystalline state of the metallic structure sets the surface plasmon resonance in the metallic particle or rod to resonate at a frequency which provides spectral overlap with either the first wavelength $\lambda_1$ or the second wavelength $\lambda_2$. Such shapes are described in the present figures and in the figures in U.S. Ser. No. 12/401,478 which is incorporated by reference in its entirety. The shape choice can affect the frequency of the surface plasmon resonance. It is known that the plasmon band is changed by the shape of nanoparticles (e.g., prolate and obloid spheroids). The paper "Spectral bounds on plasmon resonances for Ag and Au prolate and oblate nanospheroids," in the Journal of Nanophotonics, Vol. 2, 029501 (26 Sep. 2008), the entire contents of which are incorporated by reference, shows plasmon resonance shifts for shaping of Ag and plasmon resonance shifts for shaping of Au of prolate and obloid spheroids. In one embodiment of the invention, with an increasing aspect ratio for a metallic structure of the invention, the prolate spheroid resonance is red shifted relative to a sphere with no lower limit (under the assumptions of a Drude dispersion model). On the other hand, the oblate resonances are "blue shifted" as the spheroid becomes increasingly flat, but up to a limit.

In various embodiments, the metallic structures can be a metallic structure disposed interior to the nanoparticle wherein a conductivity or a dimension (e.g. a lateral dimension or a thickness) of the metallic structure sets the surface plasmon resonance in the metallic structure to resonate at a frequency which provides spectral overlap with either the first wavelength $\lambda_1$ or the second wavelength $\lambda_2$. In various embodiments, the metallic structures can be a metallic multi-layer structure disposed interior to the nanoparticle wherein a conductivity or a dimension (e.g. a lateral dimension or a thickness) of the metallic structure sets the surface plasmon resonance in the metallic structure to resonate at the first wavelength $\lambda_1$ and the second wavelength $\lambda_2$. This capability once again permits radiation at $\lambda_1$ and $\lambda_2$ to be amplified.

In another embodiment, the invention provides a nanoparticle structure including a sub 1000 nm dielectric core and a metallic structure disposed in relation to the nanoparticle. The dielectric core includes at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$. Such nanoparticle structures can exhibit in certain embodiments surface plasmon resonance in the metallic structures to enhance upconversion of light from a first wavelength $\lambda_1$ to a second wavelength $\lambda_2$.

As described above, a shell (or other structure) is in particular designed with a layer thickness (or for example a lateral dimension) to enhance the photon upconversion process through plasmonic enhancement. The thickness of the shell (or other physical characteristic) is "tuned" in its thickness to the absorption process by having a dimension in which plasmons (i.e., electrons oscillations) in shell have a resonance in frequency which provides spectral overlap with the absorption band targeted. Thus, if the upconversion is to be stimulated by 980 nm NIR light, then the thickness of the shell is "tuned" in a thickness to where a plasmon resonance resonates at a frequency also of 980 nm (or in the neighborhood thereof as plasmon resonances are typically broad at these wavelengths).

Such a plasmon resonating shell can be made of numerous transition metals, including though not limited to gold, silver, platinum, palladium, nickel, ruthenium, rhenium, copper, and cobalt or a combination or alloys or layers thereof. Such a plasmon resonating shell can be also made of a combination of metals and non-metals. When formed of a gold nanoshell, the recommended thickness to resonate with 980 nm light is approximately 3.5 nm surrounding an 80 nm upconverting core, as projected by extended Mie theory calculations. (See Jain et al., *Nanolett.* 2007, 7(9), 2854 the entire contents of which are incorporated herein by reference.) FIG. 4B is reproduced from Jain et al and illustrates the capability in the invention to "tune" the metal shell to have a spectral overlap with the excitation and/or emission radiation wavelengths. This capability of matching or tuning of the frequencies provides an enhancement of the absorption which would not be present with a dielectric core alone.

In one embodiment of the invention, the metallic structures can be an alloy such as for example a Au:Ag alloy. The alloy content can be set to adjust the frequency of the surface plasmon resonance. In one embodiment of the invention, the metallic structures can be an alloy such as for example a Pt:Ag alloy. The alloy content can be set to adjust the frequency of the surface plasmon resonance. In one embodiment of the invention, the metallic structures can be an alloy such as for example a Pt:Au alloy. The alloy content can be set to adjust the frequency of the surface plasmon resonance.

In one embodiment of the invention, the nanoparticle can be an alloy of two or more materials. In this embodiment, the alloy can have a composition between the two or more materials which is set to a compositional value where excitation of the alloy at first wavelength $\lambda_1$ produces emission at the second wavelength $\lambda_2$. In one embodiment of the invention, the nanoparticle can be a zinc sulfide and zinc selenide alloy. In one embodiment of the invention, the nanoparticle can be a zinc sulfide and cadmium sulfide alloy.

In one embodiment of the invention, the zinc sulfide and zinc selenide nanoparticle alloy can have an alloy content set to provide a predetermined surface plasmon resonance. In one embodiment of the invention, the zinc sulfide and cadmium sulfide nanoparticle alloy can have an alloy content is set to provide a predetermined surface plasmon resonance.

Some techniques for producing nanoparticles and nanoparticle alloys which are suitable for the invention are described in the following documents, all of which are incorporated herein in their entirety: U.S. Pat. Nos. 7,645,318; 7,615,169; 7,468,146; 7,501,092; U.S. Pat. Appl. Publ. No. 2009/0315446; 2008/0277270; 2008/0277267; 2008/0277268; and WO 2009/133138.

In one embodiment of the invention, the nanoparticle can be a dielectric or semiconductor configured to generate an up converted or down converted wavelength $\lambda_2$. In one embodiment of the invention, the nanoparticle can include multiple dielectrics or semiconductors respectively configured to emit at different wavelengths for $\lambda_2$. In one embodiment of the invention, multiple nanoparticles having different dielectrics or semiconductors can be included in a mixture of the nanoparticles dispersed in the medium.

In one embodiment of the invention, the thickness of the metal shell is set depending on the absorption frequency (or in some cases the emission frequency) of the particular dopant ions in the dielectric core to enhance the total efficiency of the emission process of the upconverted light. Accordingly, the thickness of the shell can be considered as a tool that in one instance enhances the absorption of $\lambda_1$, and in another instance can be considered as a tool that enhances the emission of $\lambda_2$, or in other situations can be considered an enhancement feature that in combination enhances the overall net process.

Figure 5:
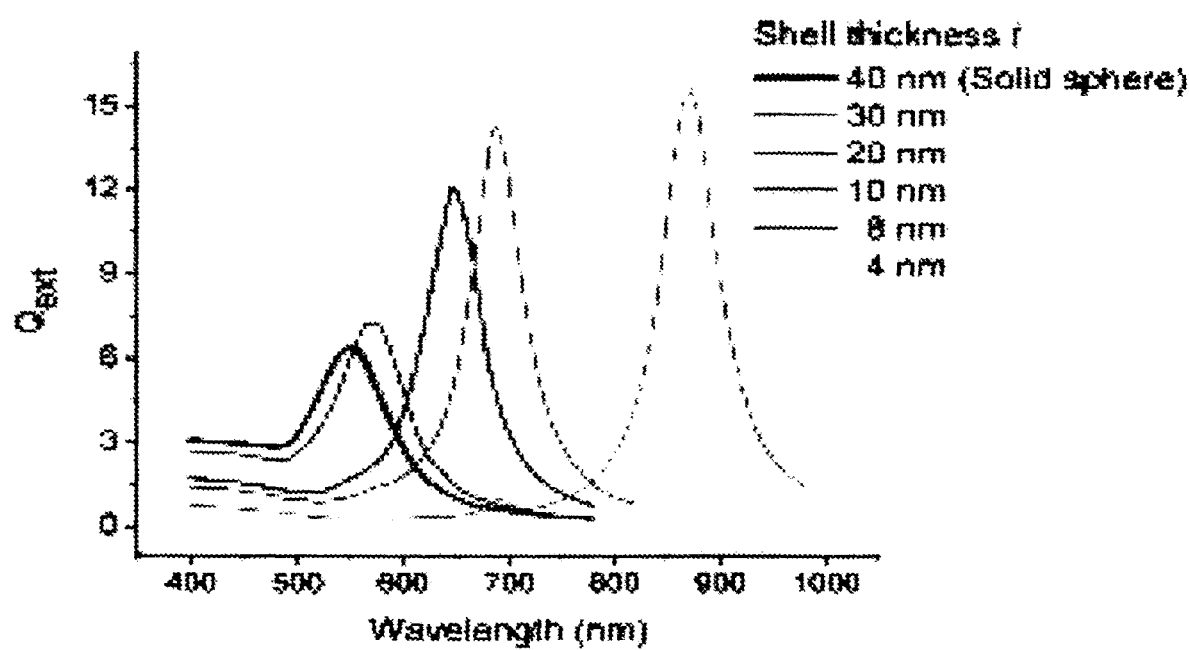
FIG. 5 is a schematic illustration of plasmon resonance as a function of shell thickness.

Additionally, plasmon-phonon coupling may be used to reduce a resonance frequency through the tuning of the bands to a degree off resonance. This may be useful in optimizing resonance energy transfer processes for the purpose of shifting the outputted color to a color desirable for a painted, colored, or displayed surface. In one example, FIG. 5 shows an example of the plasmon resonance shift as a function of shell thickness.

Here, in one embodiment of the invention, the capability to produce stimulated emission at a targeted wavelength or color is complemented by the ability to design nanoparticles for the color enhancing compositions that have designed absorption bands. Such absorption materials could for example further serve to improve the color purity of light observed from a paint, ink, dye, or otherwise reflecting surface treated with the color enhancing compositions of the invention.

Details of the preparation of this nanoparticle system are included in U.S. Ser. No. 12/725,108, the entire contents of which are incorporated herein by reference. The absorption spectrum of $Y_2O_3$ alone (lower trace) is fairly featureless, showing absorption due to the tri-arginine near 200 nm and a gentle slope associated with scattering and absorption by the $Y_2O_3$ nanoparticles extending into the visible portion of the spectrum. The gold-coated $Y_2O_3$ (upper trace), on the other hand, exhibit a strong absorption band at 546 nm, which is characteristic of the plasmonics resonance band due to the gold shell around the $Y_2O_3$ cores. The red-shifting of the plasmon absorption to 546 nm is consistent with the presence of a gold shell around a dielectric core.

In one embodiment of the invention, the materials for the upconverter dielectric core can include a wide variety of dielectric materials, as described above. In various embodiments of the invention, the upconverter dielectric core includes more specifically lanthanide doped oxide materials. Lanthanides include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Other suitable dielectric core materials include non-lanthanide elements such as yttrium (Y) and scandium (Sc). Hence, suitable dielectric core materials include $Y_2O_3$, $Y_2O_2S$, $NaYF_4$, $NaYbF_4$, Na-doped $YbF_3$, YAG, YAP, $Nd_2O_3$, $LaF_3$, $LaCl_3$, $La_2O_3$, $TiO_2$, $LuPO_4$, $YVO_4$, $YbF_3$, $YF_3$, or $SiO_2$. These dielectric cores can be doped with Er, Eu, Yb, Tm, Nd, Tb, Ce, Y, U, Pr, La, Gd and other rare-earth species or a combination thereof.

Lanthanides usually exist as trivalent cations, in which case their electronic configuration is (Xe) 4f$^n$, with n varying from 1 ($Ce^{3+}$) to 14 ($Lu^{3+}$). The transitions within the f-manifold are responsible for many of the photo-physical properties of the lanthanide ions, such as long-lived luminescence and sharp absorption and emission lines. The f-electrons are shielded from external perturbations by filled 5s and 5p orbitals, thus giving rise to line-like spectra. The f-f electronic transitions are LaPorte forbidden, leading to long excited state lifetimes, in the micro- to millisecond range.

Accordingly, examples of doped materials in the invention include oxides such as yttrium oxide and neodymium oxide and aluminum oxide as well as sodium yttrium fluoride and nanocrystalline perovskites and garnets such as yttrium aluminum garnet (YAG) and yttrium aluminum perovskite (YAP). Of these materials, doping is required for some, but not all of these materials, for promoting upconversion efficiencies. In various embodiments of the invention, the host nanocrystals are doped with trivalent rare earth lanthanide ions from those lanthanide series elements given above.

More specifically, in various embodiments of the invention, pairs of these dopants are introduced in order to make accessible more energy states in the host crystal. The activation and pumping of these energy states follows closely the principles discussed above with regard to FIG. 3. Doping concentrations in the invention can range from 0.2% to 20% roughly per ion into the host lattice or in a weight or mol % variation. The efficiency of the upconversion processes of specific bands in these materials can be modulated by the percentages doped to induce and enhance targeted emissions. Lanthanide doped upconverters while not limited to, can use the following mol percent dopant compositions: 5% Er, 10% Yb, 0.2% Tm+3% Yb, and 1% Er+10% Yb.

The size of the nanocrystal will also have an effect on the efficiency of the upconversion process, as a larger nanocrystal will have more sites for dopant ions to be accommodated into the host lattice, therefore enabling more emissions from the same doped host than if the nanocrystal were smaller. While the dopant percentages listed above are not rigidly fixed, these numbers provide a rudimentary teachings of the typical percentages one would use in obtaining a particular dielectric core material of the invention.

Moreover, some of these host crystals (e.g., neodymium oxide) in one embodiment of the invention may require no specific doping to facilitate upconversion, which has been seen in one instance in $Nd_2O_3$ with an excitation wavelength of 587 nm producing emissions at 372 nm, 402 nm, and 468 nm. See Que, W et al. Journal of Applied Physics 2001, vol 90, pg 4865, the entire contents of which are incorporated herein by reference. Doping neodymium oxide with $Yb^{3+}$, in one embodiment of the invention, would enhance upconversion through sensitizing the $Nd^{3+}$ ions with a lower energy $Yb^{3+}$ activator.

In one embodiment of the invention, the dielectric core is coated, such as for example with a metallic shell, to enhance electron-phonon coupling and thereby increase upconversion or down conversion efficiency, as discussed above. In another embodiment of the invention, the shell can include a $SiO_2$- and/or $TiO_2$-coating, and this coating is in one embodiment coated on doped $Y_2O_3$ upconverting nanoparticles to thereby, in some instances, increase the upconversion efficiency relative to an uncoated nanocrystal. In another embodiment of the invention, the shell can include a $SiO_2$- and/or $TiO_2$-coating, and this coating is in one embodiment coated on doped $Y_2O_3$ down converting nanoparticles to thereby, in some instances, increase the down conversion efficiency relative to an uncoated nanocrystal. Further, in one embodiment of the invention, the coating can be a polymer. In one embodiment, this coating is provided on $NaYF_4$:Ln/$NaYF_4$ dielectric core. Such coatings can increase the upconversion efficiency relative to an uncoated upconverter.

In another embodiment of the invention, phonon modes of an undoped host-lattice (e.g., $Y_2O_3$) nanocrystals are modulated, for example, by Au, Ag, Pt, and Pd shells of varying thicknesses. In various embodiments of the invention, the upconverter dielectric core and the shell system includes as upconverting nanocrystals $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells. In this system, the core diameter and shell outer/inner diameter of the metallic coatings can be set to dimensions that are expected to be tunable to a plasmon mode overlap.

In other embodiments as discussed below, the metal coating or the metallic structure can exist inside the dielectric and the relative position of the metal structure to the dielectric structure can enhance plasmon resonance. These structures with the metallic structure inside can be referred to as a metallic core up converter or a metallic core down converter. The metallic core technique for energy conversion is useful since it takes advantage of metal nano-particles that have improved surface morphology compared to shell coatings on core dielectrics. The metal or metallic alloy in the inner core metallic energy converter can be selected to tune its plasmonic activity. These structures with the metallic structure outside can be referred to as a core up converter or a core down converter.

In various embodiments of the invention, the upconverter or down converter dielectric core can be coated with thiol-terminated silanes to provide a coating of $SiO_2$ about the core of similar reactivity to $Y_2O_3$. In one embodiment of the invention, the above-described methodology is used to synthesize core-shell nanoparticles of $Y_2O_3$:Ln with $NaYF_4$ shells, $Y_2O_3$:Ln with Au(Ag,Pt) shells, $NaYF_4$:Ln with $Y_2O_3$ shells, $NaYF_4$:Ln with Au(Ag,Pt) shells where core and shell diameters varying from 2 to 20 nm. In these material systems, the tuned ratio of core-to-shell diameter may permit a plasmon-phonon resonance which should amplify absorption of NIR light and/or upconverted emission. In these material systems, control of the core and shell diameters is one factor determining the size dependent effect and subsequent tuning of plasmon-phonon resonance.

In one embodiment of the invention, the upconverter dielectric core can be mixed core-shell materials including for example semiconducting $Y_2O_3$ and $NaYF_4$ cores doped with various Ln series metals, which have been shown to possess large upconverting efficiencies. These doped $Y_2O_3$ and $NaYF_4$ cores will have shells of Au(Ag,Pt, Pd) or undoped $Y_2O_3$ and $NaYF_4$ matrices which have the potential to enhance or tune the phonon modes needed for energy transfer in the upconversion process. Solubility can be enhanced, for example, by addition of thiolated organics (Au shell), organic chain triethanolsilane ($Y_2O_3$ shell), and tri-octylphospine-oleic amine ($NaYF_4$ shell). All core-shell nanoparticles may further be solubilized into a colloidal suspension with the addition of triarginine peptide, polyethylene glycol, and polyethyleneimine surfactants.

FIG. 6A shows some of the various embodiments of the upconverter structures of the invention that can be designed: (a) a structure including upconverter (UC) molecules bound to a metal (gold) nanoparticle; (b) a structure including an UC-containing nanoparticle covered with metal nanoparticles, (c) a metal nanoparticle covered with an UC-containing nanocap; (d) an UC-containing nanoparticle covered with metal nanocap, (e) a metal nanoparticle covered with UC nanoshell, (f) an UC-containing nanoparticle covered with metal nanoshell, (g) an UC-containing nanoparticle covered with metal nanoshell with protective coating layer.

The configurations (while shown in the FIG. 6 series with UC-containing materials) would be applicable for enhancement for down converting materials such as the quantum dots described above. Moreover, in one embodiment of the invention, dielectric spacers (for examples silicates as discussed below) can be used with the structure of FIG. 6A-b to space apart the particle type metallic structures. In another embodiment of the invention, dielectric spacers can be used with the structure of FIG. 6A-d, f to space apart the metal layers, whether or not these layers are partial metal layers as in FIG. 6A-d or continuous metal layers as in FIG. 6A-f See FIGS. 6B-b, d, and f.

The plasmonic properties of various metallic structures, which have been investigated in the art and are suitable for the invention, include metallic nanoshells of spheroidal shapes [S. J. Norton and T. Vo-Dinh, "*Plasmonic Resonances of Nanoshells of Spheroidal Shape*", IEEE Trans. Nanotechnology, 6, 627-638 (2007)], oblate metal nanospheres [S. J. Norton, T. Vo-Dinh, "*Spectral bounds on plasmon resonances for Ag and Au prolate and oblate nanospheroids*", J. Nanophotonics, 2, 029501 (2008)], linear chains of metal nanospheres [S. J. Norton and T. Vo-Dinh, "Optical response of linear chains of metal nanospheres and nanospheroids", *J. Opt. Soc. Amer.*, 25, 2767 (2008)], gold nanostars [C. G. Khoury and T. Vo-Dinh, "*Gold Nanostars for Surface-Enhanced Raman Scattering: Synthesis, Characterization and Applications*", *J. Phys. Chem C*, 112, 18849-18859 (2008)], nanoshell dimmers [C. G. Khoury, S. J. Norton, T. Vo-Dinh, "*Plasmonics of 3-D Nanoshell Dimers Using Multipole Expansion and Finite Element Method, ACS Nano*, 3, 2776-2788 (2009)], and multi-layer metallic nanoshells [S. J. Norton, T. Vo-Dinh, "*Plasmonics enhancement of a luminescent or Raman-active layer in a multilayered metallic nanoshell*", *Applied Optics*, 48, 5040-5049 (2009)]. The entire contents of each of the above noted references in this paragraph are incorporated herein by reference. In various embodiments of the invention, multi-layer metallic nanoshells discussed in this application have the potential capability to enhance electromagnetically two spectral regions. Accordingly, the metallic structures of the invention can be used in the upconverting mode to enhance both the excitation at wavelength $\lambda_1$ and the emission at wavelength $\lambda_2$. This feature also can be used in the down converting to enhance primarily the emission at wavelength $\lambda_2$ and potentially the excitation at wavelength $\lambda_1$.

Such metallic structures in various embodiments of the invention include conducting materials made for example of metals, or doped glasses or doped semiconductors. These conducting materials can be in the form of pure or nearly pure elemental metals, alloys of such elemental metals, or layers of the conducting materials regardless of the constituency. The conducting materials can (as noted above) include non-metallic materials as minor components which do not at the levels of incorporation make the composite material insulating.

Similarly, in various embodiments of the invention, the up or down converting materials can include at least one of a dielectric, a glass, or a semiconductor. The up or down converting materials can include an alloy of two or more dielectric materials, an alloy of two or more glasses, or an alloy of two or more semiconductors.

Accordingly, FIG. 6A represents embodiments of the invention where the dielectric core is supplemented with a shell. The shell can include a metal layer of a prescribed thickness. The metal layer can include materials such as nickel, gold, iron, silver, palladium, platinum and copper and combinations thereof. The metal layer can be also made of a combination of metals and non-metals. The shell functions as a plasmonic shell where surface plasmons can form in the metal between the dielectric core and the outer environment acting as an exterior dielectric. The shell (as shown) may not be a complete shell. Partial metallic shells or metallic shells of varying thicknesses are also acceptable in the invention.

As discussed below, the metallic shells in another embodiment of the invention serve as scattering centers for UV light where UV light which, even if absorbed in a paint or coating layer contributes at a minimum to localized heating of the paint or coating layer material, will be scattered from the paint or coated layer.

FIG. 6B shows yet other embodiments of upconversion structures that have a dielectric layer between the metal and the UC materials.

FIG. 6C shows still further embodiments of plasmonics-active nanostructures having upconverting (UC) materials that can be designed: (a) a metal nanoparticle, (b) an UC nanoparticle core covered with metal nanocap, (c) a spherical metal nanoshell covering an UC spheroid core, (d) an oblate metal nanoshell covering UC spheroid core, (e) a metal nanoparticle core covered with UC nanoshell, (f) a metal nanoshell with protective coating layer, (g) multi layer metal nanoshells covering an UC spheroid core, (h) multi-nanoparticle structures, (i) a metal nanocube and nanotriangle/nanoprism, and (j) a metal cylinder.

Figure 6D:
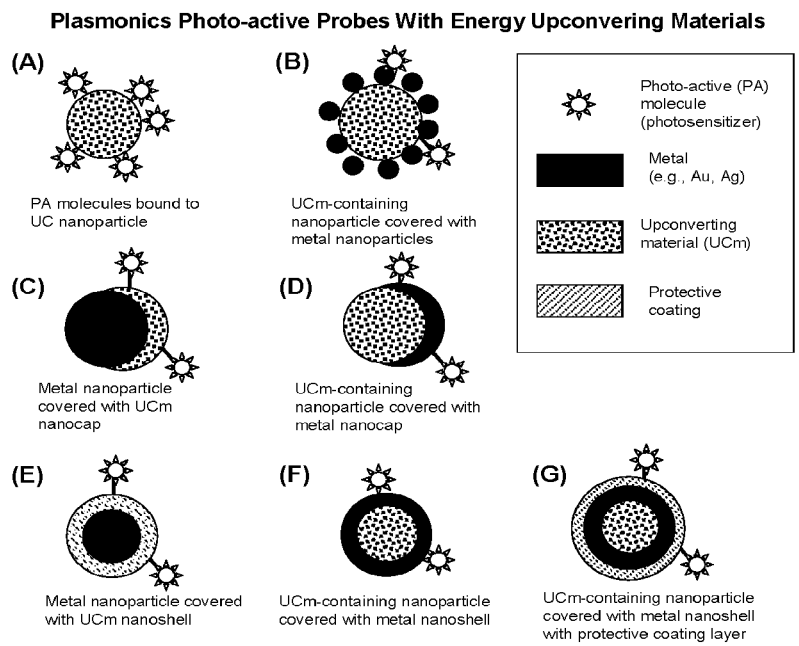
FIG. 6D is a schematic illustration of photo-active molecules linked to plasmonics-active upconverter structures of the invention.

FIG. 6D shows yet other embodiments of plasmonics-active nanostructures having upconverting materials with linked photo-active (PA) molecules that can be designed. For example, for the case of psoralen (as the PA molecule), the length of the linker between the PA molecule and the UC material or the metal surface is tailored such that it is sufficiently long to allow the PA molecules to be active (attach to DNA) and short enough to allow efficient excitation of light from the UC to efficiently excite the PA molecules. FIG. 6D shows (a) PA molecules bound to an UC nanoparticle, (b) an UC material-containing a nanoparticle covered with metal nanoparticles, (c) a metal nanoparticle covered with UC material nanocap, (D) an UC material-containing nanoparticle covered with metal nanocap, (e) a metal nanoparticle covered with an UC material nanoshell, (f) an UC material-containing nanoparticle covered with metal nanoshell, (g) an UC material-containing nanoparticle covered with metal nanoshell with protective coating layer.

With the upconverter and down converter structures of the invention, a plasmonics effect is advantageous. A plasmonics effect can increase the local intensity of the received light or the local intensity of the emitted light from the up and/or down converter structures of the invention. A plasmonics effect can occur throughout the electromagnetic region provided the suitable nanostructures, nanoscale dimensions, metal types are used. Plasmonic effects are possible over a wide range of the electromagnetic spectrum, ranging from gamma rays and X rays throughout ultraviolet, visible, infrared, microwave and radio frequency energy. However, for practical reasons, visible and NIR light are used for metal structures such as for example silver and gold nanoparticles, since the plasmon resonances for silver and gold occur in the visible and NIR region, respectively.

The color-shifting structures of the invention include in various embodiments nanoparticles of neodymium and ytterbium doped yttrium oxide, europium and ytterbium doped yttrium oxide, and any combination of rare earth trivalent ions doped into a neodymium oxide nanocrystal. The dual doped yttrium oxide of composition neodymium and ytterbium and also the dual doped europium and ytterbium are new for the yttrium oxide host lattice, although such dual doped systems have been shown to work in other host lattices such as YAG.

These dual doped lanthanide glasses have been shown to upconvert efficiently on bulk materials, and thereby can provide new upconverter structures at the nano-scale. There are a number of advantages offered by these yttrium oxide nanostructures of the invention. The small scale synthetic methodology for creating nanoscale yttrium oxide is easier to control and produce in yttrium oxide than in YAG. The host structure of yttrium oxide scintillates by down conversion. These combinations of dopants in yttrium oxide for example can provide predetermined emission colors for the yttrium oxide nanocrystal for the color shifting of the invention.

In one embodiment of the invention, a dual dopant permits excitation of either ion in the host glass. For instance, excitation by 980 nm light excites an ytterbium ion, where through transfer of energy from one excited state of the ytterbium ion to another dopant provides a mechanism for upconversion emission of light in the visible and NIR spectral regions.

Up-conversion phosphors similar in chemical compositions to the down-conversion fluorescent materials discussed above can be used. The up-conversion phosphors can include laser dyes, e.g., the organic small molecules that can be excited by the absorption of at least two infrared photons with emission of visible light. The up-conversion phosphors can include fluorescent polymers, e.g., the class of polymers that can be excited by the absorption of at least two infrared photons with emission of visible light. The up-conversion phosphors can include inorganic or ceramic particles or nano-particles, including the conventional up-conversion phosphors (e.g. metal fluorides, metal oxides) that can be excited by the absorption of at least two infrared photons with emission of visible light. The up-conversion phosphors can include semiconductor particles, including nano-particles such as II-VI or III-V compound semiconductors, e.g. quantum dots, described in details in the "down-conversion" semiconductors above.

Fluorescent up-conversion inorganic phosphors can include but are not limited to metal oxides, metal halides, metal chalcoginides (e.g. sulfides), or their hybrids, such as metal oxo-halides, metal oxo-chalcoginides. Fluorescent up-conversion inorganic phosphors are usually doped with rare earth elements (e.g. $Yb^{3+}$, $Er^{3+}$, $Tm^{3+}$). Some host examples include, but are not limited to: $NaYF_4$, $YF_3$, $BaYF_5$, $LaF_3$, $La_2MoO_8$, $LaNbO_4$, $LnO_2S$; where Ln is the rare earth elements, such as Y, La, Gd).

These up conversion and down conversion materials, according to the invention, are a mixture of color emitters configured to emit, upon exposure to a light source, visible light at a first wavelength $\lambda_1$ in response to absorption of light or energy across a band of wavelengths inside and outside the visible spectrum. The visible light emission is enhanced relative to an amount of light which would be emitted only by reflection of the first wavelength $\lambda_1$.

The color emitters particles can have a diameter less than about 1000 nanometers. The light emitting particles (up or down) can include a metallic structure disposed in relation to the particle. A physical characteristic of the metallic structure is set to a value where a surface plasmon resonance in the metallic structure resonates at a frequency which provides spectral overlap with either the first wavelength $\lambda_1$. The physical characteristic of the metallic structure is set to a value where a surface plasmon resonance in the metallic structure resonates at a frequency which provides enhanced emission at the first wavelength $\lambda_1$.

As detailed below, the mixture of color-emitters can be attached to a dye molecule of a display. The mixture of color-emitters can be a color emitting pixel display element. The mixture of color-emitters can be a component of a color filter. The mixture of color-emitters can be a component of a color filter for a display. The mixture of color-emitters can be a component of a colored surface. The mixture of color-emitters can be a component of a colored reflective surface. The mixture of color-emitters can be a component of a colored reflective surface in a pixel for a display. The mixture of color-emitters can be a component of a white-light emitting pixel display element. The mixture of color-emitters can be a paint component. The mixture of color-emitters can be a component disposed on glass beads in a retroreflective paint. The mixture of color-emitters can be a component of a binder layer securing glass beads in a retroreflective paint to a base paint. The mixture of color-emitters can be an ink component.

The mixture of color-emitters can be at least one of red, blue, and green emitters configured to produce red, blue, and green emissions from an up conversion process. The mixture of color-emitters can be at least one of red, blue, and green emitters configured to produce red, blue, and green emissions from a down conversion process. The mixture of color-emitters can be at least one of red, blue, and green emitters configured to produce red, blue, and green emissions from a mixture of up converters and down converters.

The mixture of color-emitters can be fluorescent emitters including at least one of europium, terbium, cerium, and erbium or combinations thereof. The mixture of color-emitters can include a first material configured to emit a first visible color in response to absorption of ultraviolet light and a second material configured to emit a second visible color in response to absorption of infrared light, wherein the second visible color is different from the first visible color. The mixture of color-emitters can include a third material configured to emit a third visible color in response to absorption of the ultraviolet light, wherein the third visible color is different from the first visible color and the second visible color. The first visible color, the second visible color, and the third visible color can be the primary colors or a mixture of the primary colors. Alternatively or in addition, the mixture of color-emitters can include a third material configured to emit a third visible color in response to absorption of the infrared light. The third visible color can be different from the first visible color and the second visible color.

The mixture of color-emitters can include a first material configured to emit a first visible color in response to absorption of ultraviolet light and a second material configured to emit a second visible color in response to absorption of infrared light. The second visible color can be substantially the same color as the first visible color. The mixture of color-emitters can include a third material configured to emit a third visible color in response to absorption of the ultraviolet light. The third visible color can be different from the first visible color and the second visible color. Alternatively or in addition, the mixture of color-emitters can include a third material configured to emit a third visible color in response to absorption of the infrared light. The third visible color can be different from the first visible color and the second visible color. The first visible color, the second visible color, and the third visible color can be the primary colors or a mixture of the primary colors.

The mixture of color-emitters can include a metallic structure disposed in relation to a nanoparticle emitter. The metallic structure can be a metallic shell including at least one of a spherical shell, an oblate shell, a crescent shell, or a multilayer shell. The metallic structure can be at least one of Au, Ag, Cu, Ni, Pt, Pd, Co, Ru, Rh, Al, Ga, or a combination or alloys or layers thereof. The nanoparticle emitter can beat least one of $Y_{23}$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof. The nanoparticle emitter can include a dopant including at least one of Er, Eu, Yb, Tm, Nd, Tb, Ce, Y, U, Pr, La, Gd and other rare-earth species or a combination thereof. The dopant can have a concentration of 0.01%-50% by mol concentration.

The color-emitters can be a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^3$; ZnS:$Tb^3$; $Y_2O_3$: $Tb^{3+}$; $Y_2O_3$:$Tb^{3+}$, $Er^{3+}$; ZnS:$Mn^{2+}$; ZnS:Mn,$Er^{3+}$, alkali lead silicate including compositions of $SiO_2$, $B_2O_3$, $Na_2O$, $K_2O$, PbO, MgO, or Ag, and combinations or alloys or layers thereof. The color-emitters can be a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof. The dielectric up converter can have a particle diameter ranging from at least one of 2-1000 nm, 2-100 nm, 2-50 nm, 2-20 nm, or 2-10 nm. The dielectric up converter can include a dopant of at least one of Er, Eu, Yb, Tm, Nd, Tb, Ce, Y, U, Pr, La, Gd and other rare-earth species or a combination thereof. The dopant can have a concentration of 0.01%-50% by mol concentration. A metallic structure can be disposed in relation to the dielectric up converter, and the metallic structure includes at least one of Au, Ag, Cu, Ni, Pt, Pd, Co, Ru, Rh, Al, Ga, or alloys or layers thereof. The dielectric up converter can be configured to exhibit visible emission upon interaction with NIR light.

Coating Applications:

Almost all surfaces of products exposed to our environment are either coated, painted, stained, or sealed with a protect that helps the underlying material resist deterioration from the environmental factors such as sun, wind, raid, moisture, salt, acid, and alkali exposure. Stainless steel, aluminum, and copper are a few examples of materials who do not necessarily require a coated, painted, stained, or sealed protective layer. The coated surfaces are almost always of a particular color chosen to improve the attractiveness of the object.

As described at http://www.howeverythingworks.org/supplements/paint.pdf, pigment particles in paint are responsible for the opacity or color of the paint. Pure white paint has pigment that absorbs no light but rather scatters light in random directions. White pigment particles are clear and have relatively high refractive indices. The pigment particles are embedded in a polymer layer. As light tries to pass through the paint, part of the light is reflected at every boundary between polymer and pigment, and almost none of the light reaches the back of the layer. Because the pigment particles in the paint are typically rough and randomly oriented, the pigment particles scatter the light in every direction making the paint appear to be white. This high reflectivity gives paint its hiding power-its ability to prevent light from reaching the material beneath the paint and then returning to paint's surface.

Paints with very high refractive index pigments are best at hiding the surfaces they cover. Absorption of light in the pigments will give the paint. For example, a pigment which absorbs blue light will give the paint a yellow tint. The reflected light has a color characteristic of the non-absorbed colors of the spectrum. In other words, colored pigments give paints their colors by selectively absorbing some of the spectrum of light striking the paint.

U.S. Pat. No. 4,283,320 (the entire contents of which are incorporated herein by reference) describes an opacified latex paint having small particle film-forming latex binders in combination with minor amounts of opacifying pigment, and substantial amounts of non-film-forming polymeric particles (plastic pigment) provides a semi-gloss latex paint composition having excellent hard enamel surfaces along with desirable film integrity properties. The plastic pigment particles in U.S. Pat. No. 4,283,320 are between about 0.1 and 0.5 microns and contain 0.2 to 2% copolymerized monomers containing carboxylic acid groups. The semi-gloss plastic pigment latex paint of U.S. Pat. No. 4,283,320 is compounded at pigment-volume-content (PVC) between about 30% and 45% and considerably higher than conventional high quality enamel latex paints. Into the latex paint of U.S. Pat. No. 4,283,320 or onto painted surface of U.S. Pat. No. 4,283,320, in one embodiment of the invention, the color enhancing mixtures described herein are applied.

U.S. Pat. No. 5,134,186 (the entire contents of which are incorporated herein by reference) describes a paint having a film former and polymeric composition. The polymeric composition comprises about 30 to about 50 weight percent of a substantially non-self-polymerizable monomer and about 50 to about 70 weight percent of a copolymerizable monomer having a water-soluble homopolymer. Into the latex paint of U.S. Pat. No. 5,134,186 or onto painted surface of U.S. Pat. No. 5,134,186, in one embodiment of the invention, the color enhancing mixtures described herein are applied.

U.S. Pat. No. 4,789,694 (the entire contents of which are incorporated herein by reference) describes a paint coating composition having a cationic free, functional emulsion polymer mixture adapted to be coreacted at room temperature with glycoluril to provide a cured thermoset paint film. The curing copolymerizes ethylenically unsaturated monomers, including functional monomers, but excluding amine monomers, in an aqueous polymerization medium, followed by ion exchange of the resulting reactive emulsion polymer. The glycoluril can be processed through an ion exchange step separately or in conjunction with the reactive emulsion polymer. Into the latex paint of U.S. Pat. No. 4,789,694 or onto painted surface of U.S. Pat. No. 4,789,694, in one embodiment of the invention, the color enhancing mixtures described herein are applied.

U.S. Pat. No. 4,613,633 (the entire contents of which are incorporated herein by reference) describes a copolymer latex having heterogeneous polymer particles which is particularly suitable for paper coating, and to a paper coating composition comprising this latex which gives coated paper having improved adaptability to blister packaging and printing. Into the latex paint of U.S. Pat. No. 4,613,633 or onto painted surface of U.S. Pat. No. 4,613,633, in one embodiment of the invention, the color enhancing mixtures described herein are applied.

U.S. Pat. No. 7,682,435 (the entire contents of which are incorporated herein by reference) describes an oil-based pigmented ink composition containing at least a pigment, a polymer compound and an organic solvent, which contains, as the organic solvent, methoxybutyl acetate in an amount of 20 to 90% by weight based on the entire ink composition; and particularly to the above oil-based pigmented ink composition, which contains, as the other organic solvent, a nitrogen-containing and/or oxygen-containing heterocyclic compound in an amount of 1 to 50% by weight based on the entire ink composition and/or a (poly)alkylene glycol derivative in an amount of 1 to 50% by weight based on the entire ink composition; and to the above oil-based pigmented ink composition, which has a flash point of 61° C. or higher, a viscosity of 2.0 to 6.5 cp at 25° C., and a surface tension of 20 to 40 mN/m at 25° C. Into the oil based pigmented ink of U.S. Pat. No. 7,682,435 or onto painted surface of U.S. Pat. No. 7,682,435, in one embodiment of the invention, the color enhancing mixtures described herein are applied.

U.S. Pat. Application Publ. No. 20090088500 (the entire contents of which are incorporated herein by reference) describes an oil-based ink composition having a colorant, an organic solvent and a polymeric compound, and optionally an alkylamine ethylene oxide derivative as a pH adjusting agent, in which the pH of an aqueous phase is from 5.5 to 10, when ions in the ink composition are transferred to water. This oil-based ink composition prevents corrosion of a nozzle plate and is improved in storage stability, and thus can ensure printer reliability such as ink-jet stability obtainable even after long storage thereof, and can withstand outdoor service environments. Into the oil-based ink composition of U.S. Pat. Application Publ. No. 20090088500, in one embodiment of the invention, the color enhancing mixtures described herein are applied.

In general, the color enhancing mixtures described herein are applicable to other paints or inks to enhance the color perceived by an observer.

Human eyes are not instruments which measure precise wavelengths of light. Instead, a human eye looks for three different ranges of wavelengths. Within the retina of the human eye, there are specialized cells that only detect light of certain wavelengths. Some of these cells detect reddish light, others detect greenish light, and still others detect bluish light. These three types of color sensitive cells are called cone cells. Cone cells are most abundant in the fovea—the region of high visual acuity near the center of the retina. Retinal cells are more light-sensitive than cone cells but can not distinguish color. Rod cells sense light and dark. It might seem as through these three types of color sensors will only allow one to see three colors. Yet, a wide variety of colors are perceived when two or more of the color sensors are stimulated at once. Each sensor informs the brain about how much light it sees and the brain interprets the mixture of responses as a particular color.

In general, visible light of a particular wavelength stimulates all three types of cone cells to some extent. However, the cells do not respond equally to each wavelength of light. When exposed 680 nm (680 nanometer) light, the cone cells specialized for reddish light respond much more strongly than those specialized for greenish or bluish light. Because of this strong response by the red sensors, the light appears to be red. Yellow light at 580 nm is in between red and green light. Both the red sensitive cone cells and the green sensitive cone cells respond moderately when exposed to yellow light. The brain interprets this balanced response as yellow light.

But the same response can be invoked from your retina by exposing it to an equal mixture of pure red and green lights. Again, both the red sensitive and green sensitive cone cells respond moderately, and it appears to the brain as yellow light, even though there is no pure yellow light at 580 nm reaching your retina. Likewise, a mixture of pure red, green, and blue lights can make one see virtually any color. The only problem comes in choosing the pure red, green, and blue wavelengths. This is the technique used by a television. It creates relatively pure red, green, and blue lights with phosphor dots and "tricks" the eyes into seeing any color across the visible spectrum.

Accordingly, in a red paint, this paint absorbs light that would stimulate green or blue sensors of your eyes. All that is left is reflected light that stimulates red sensors, so the eye perceives the paint as red. Most paint pigments are based on specific molecules that absorb light in a particular range of wavelengths. Many metal compounds, including those of copper, chromium, iron, antimony, nickel, and lead absorb certain wavelengths of light and appear brightly colored. If one starts with white light and removes various amounts of the three primary colors of light, one can create any color of paint. If you remove all light, the paint appears to be black. A yellow pigment absorbs some blue light, and a cyan pigment absorbs some red light. What is left is mostly green light. The more of each primary pigment added to the paint, the more completely the paint will absorb its color of light, and the deeper the color the paint will become.

Inks are similar to paints except that inks contain dissolved dyes rather than solid pigment particles. Inks do not contain any reflective white pigments. Inks themselves tend to be transparent but colored. Inks rely on the underlying paper to reflect light. Paper consists mainly of cellulose, a clear natural polymer. Because this cellulose is finely divided in paper, it reflects light at each surface and the paper appears white. Often white paint pigments are applied to paper during manufacture to make the paper even whiter.

In one aspect of the invention, the conventional dynamic of the absorption of light in a paint normally resulting only in the heating of the paint is changed to a dynamic of the absorbed light (normally lost from the absorption) being emitted a color of light of intended paint color. Thus, the brightness of the paint or ink or coating is enhanced over that which would normally be lost to absorption. Furthermore, "color shifting" from bands of light outside the visible in the ultraviolet or infrared which normally contribute nothing to the perceived light reflected to the eye provides an additional source of color enhancement.

Conventionally, in the production of the fluorescent ink, fluorescent pigments were employed in place of organic or inorganic color pigments exhibiting absorption in a visible light region and being used in the ordinary printing inks. In order to identify fluorescent images formed on an image-printed article, it is required to irradiate the image-printed article with ultraviolet rays employed as an exciting light. When the image-printed article was irradiated with ultraviolet rays, the ultraviolet rays are absorbed by the fluorescent substance of fluorescent images, thereby causing the emission of fluorescence in the visible region. This fluorescence was recognized through visual observation or using a camera, and represents a limited demonstration of the concept utilized and yet extended by the present invention. In one aspect of the invention here, a mixture of down-converting particles tuned to a specific excitation and emission are used instead of a fixed fluorescent particle. In one aspect of the invention here, a mixture of down-converting particles tuned to a specific excitation and emission are used instead of or in complement to the mixture of down-converting particles.

As described in U.S. Pat. No. 6,744,960 (the entire contents of which are incorporated herein by reference) and applicable to this invention, pump radiation may comprise natural light, i.e., sunlight, or artificial light such as from UV or blue light emitting diodes (LED) or fluorescent lights. The light incident on the fluorescent structure need only comprise radiation having wavelengths within the absorption spectrum of the quantum dots. Since the absorption spectrum of the quantum dots comprises wavelengths shorter than the wavelength of emission from the quantum dots, the pump radiation includes wavelengths shorter than the emitted wavelengths. For example, sunlight can be employed to pump a fluorescent structure 10 having a layer of quantum dots comprising CdSe particles 5.0 nm in diameter, which emit at an optical wavelength of 625 nm, since the sun radiates light across a broad spectrum including light having wavelengths at least 50 nm shorter than 625 nm. Alternatively, such a fluorescent structure can be pumped with one or more light emitting diodes (LEDs) that provide light of, for example, 550 nm. Incandescent lights as well as ultraviolet light sources such as UV LEDs would also be capable of exciting the layer of quantum dots.

The fluorescent structures described in U.S. Pat. No. 6,744,960 and applicable to this invention can be employed in various applications requiring bright, narrowband illumination. For example, light sources of colored illumination are useful in constructing signs, in creating artistic or architectural designs, and in producing bright regions of color, including outlines, bands and borders on products including but not limited to furniture, automobiles, appliances, electronics, clothes or any other object where bright color is useful for aesthetic or functional purposes. These fluorescent structures are advantageously capable of producing intense colored light illumination during daytime when exposed to daylight. Since, quantum dots do not degrade with exposure to UV rays such as produced by the sun, the structure has a long lifetime and can be incorporated in architectural features, such as a border to highlight a rooftop of a building during the daytime.

Yet, unlike that in U.S. Pat. No. 6,744,960, in this invention, upconverting particles stimulated by IR light from natural or artificial sources complement the fluorescence and yield even brighter structures. Moreover, mixtures of the down converters permit a wider spectrum of the "out-of-band" color region from the natural or artificial radiation source to be utilized and tuned for example to a specific color emission or to a mixture of primary color emissions.

In still another embodiment of the invention, there is provided a light emitting composition including first color emitters configured to emit, upon exposure to an energy source, visible light at a target color in response to absorption of energy at a first band of wavelengths and second color emitters configured to emit, upon exposure to the energy source, visible light offset from the target color in response to absorption of energy at the first band of wavelengths, Light intensity observable at the target color is enhanced relative to reflected white light without emission from the first and second color emitters. Further, by offsetting the emissions about the target color, the resulting color would appear to the human eye to be richer in color. The offset can be an offset of 5, 10, 15, 20, 25, and 30 nm or more. The offset can be a positive or negative offset from the target color. More specifically, a color purity or chromaticity can be changed by the offset defined above.

In another embodiment, the offset values can produce a saturation quality where the target color will appear different under different lighting conditions. For instance, a room painted to a specific target color by the mixtures of different color emitters will appear different at night (under artificial lighting conditions) than in daylight. The offset can be an offset of 50, 100, 150, 200, 250, and 300 nm or more. The offset can be a positive or negative offset from the target color.

Moreover, a target color can vary from its original color by adding white pigment to make a lighter version or by adding black pigment to make a darker version.

Table 1 included below includes the recognized wavelength intervals for the major visible color bands.

TABLE 1

| color | wavelength interval |
|---|---|
| red | ~700-635 nm |
| orange | ~635-590 nm |
| yellow | ~590-560 nm |
| green | ~560-490 nm |
| blue | ~490-450 nm |
| violet | ~450-400 nm |

Figure 7:
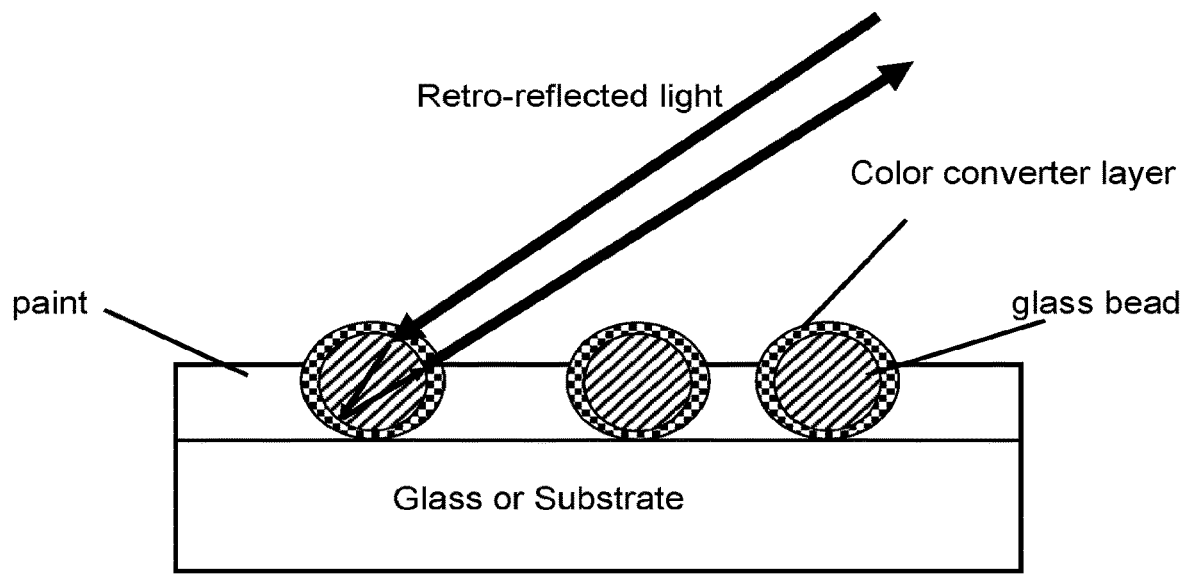
FIG. 7 is a schematic representation of the retro-reflective paint geometry using the color shifting particles of this invention.

One area of particular application for the color shifting particle mixtures would be their use as coatings on glass beads for use in retro-reflective paints. FIG. 7 shows a schematic representation of the retro-reflective paint geometry. The glass bead serves as an optical element directing incident light along a path of reflection back to the observer that is nearly, if not perfectly, aligned with the incident ray. Instead of diffuse scatter, the light is directed back and appears brighter than "normal." In this invention, the color shifting particle mixtures would be applied to the paint binder or, as shown in FIG. 7 as a color converter layer on the glass bead so that light (not of the color of the painted surface) would be converted to that color of the painted surface (or of a combination of primary color emissions simulating the color of the painted surface) so that additional light enhancement is realizable.

In conventional retroreflective road paint applications, there exist two classes of retroreflective beads: IGB-I and IGB-II. IGB-I is used to be mixed with the paint prior to stripping the road. As the paint layers wear, the beads are exposed giving the enhanced visibility of road markings IGB-II is used to be dropped on the freshly stripped paint surface on the road to give immediate enhanced visibility to night drivers. Table 2 (reproduced below from http://www.indoglassbeads.com/road-marking-glass-beading.htm) provides recognized specifications for these materials.

TABLE 2

| Chemical & Physical Properties | |
|---|---|
| Basic material | SiO2 69-71% |
| Shape | Spherical |
| Color | Clear |
| Specify gravity g/cm3 | 2.5 |
| Hardness (Moh's) | 6.0 |
| Refractive Index | 1.5-1.55 |

| Type | Sieve Size um | Retained by % |
|---|---|---|
| IGB-I | 1180 | 0-3 |
| (Intermix) | 650 | 5-20 |
|  | 425 | 65-95 |
|  | <425 | 0-10 |
|  | Roundness | >70% |
| IGB-II | 850 | 0-5 |
| (Drop On) | 600 | 5-20 |
|  | 300 | 30-75 |
|  | 180 | 10-30 |
|  | <180 | 0-15 |
|  | Roundness | >80% |

U.S. Pat. No. 5,650,213 (the entire contents of which are incorporated herein by reference) describe retroreflective compositions having anon-volatile matrix material, a volatile constituent, and a plurality of retroreflective microsphere beads where the ratio of the volume of matrix material to the volume of retroreflective microsphere beads is in the range of 75% to 185%. The retroreflective microsphere beads in U.S. Pat. No. 5,650,213 had a diameter of 20 to 200 microns, were constructed of glass, and had an index of refraction ranging from 1.7 to 2.5. These and other retroreflective compositions include (in one embodiment of the invention), the color enhancing mixtures of the invention coated thereon or in the paint composition itself.

Accordingly, in this invention, a glass bead in for example a blue paint would have down converters and up converters in the color converter layer on the glass bead so that white light (for example as from a head light on a car) would have its UV and IR light converted more to blue light thereby producing more blue light to be reflected from the blue painted surface. Alternatively, for a green painted surface, white light would have its UV and IR light converted more to green thereby producing more green light to be reflected from the glass bead in the painted surface.

Figure 8:
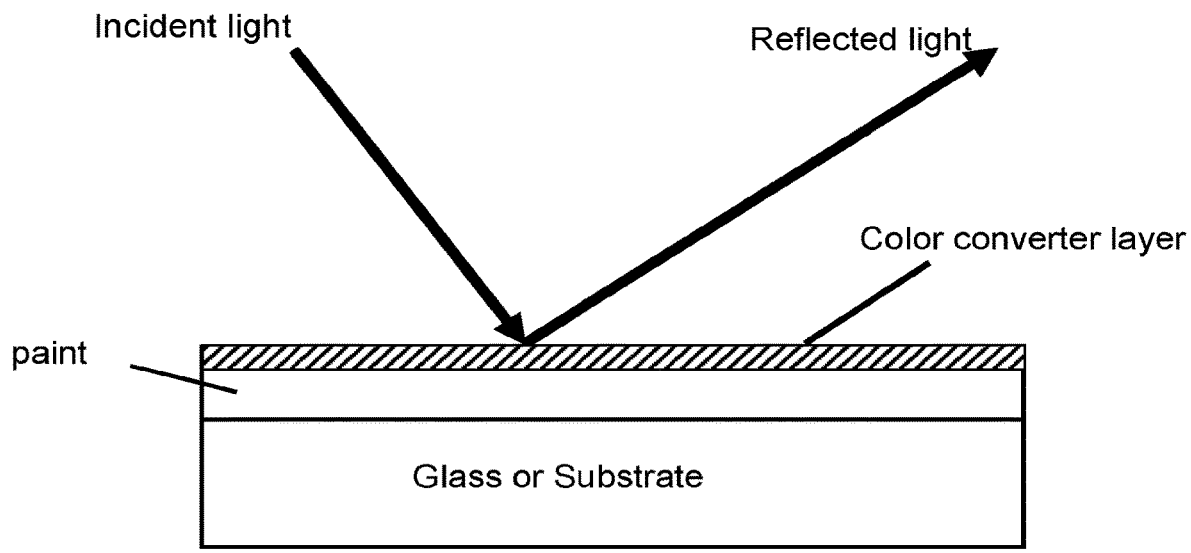
FIG. 8 is a schematic representation of a top coat on a painted surface which includes the color shifting particles of this invention.

FIG. 8 shows a schematic representation of a painted surface in which a color shifting layer in disposed as a topcoat. Similar to above before, a blue paint would have down converters and up converters in the color converter layer applied at a topcoat so that white light (for example as from a head light on a car) would have its UV and IR light converted more to blue light thereby producing more blue light to be reflected from the blue painted surface. Alternatively, for a green painted surface, white light would have its UV and IR light converted more to green light thereby producing more green light to be reflected from the glass bead in the painted surface.

In another embodiment, the colors in the visible part of the spectrum are also color shifted. A blue paint would have down converters and up converters in the color converter layer applied at a topcoat so that white light (for example as from a head light on a car) would have its deep blue and red-green light converted more to blue light thereby producing more blue light to be reflected from the blue painted surface. Alternatively, for a green painted surface, white light would have its blue and red light converted more to green light thereby producing more green light to be reflected from the glass bead in the painted surface.

Stated differently, with the color shifting particles of the invention in the color converter layer, the red paint or ink has color shifting particles which down convert the spectrum of light of a higher energy than red (e.g., a blue light) and up convert the spectrum of light of a lower energy than red (e.g., near IR and IR light). Similarly, the green paint or ink has color shifting particles which down convert the spectrum of light of a higher energy than green (e.g., a blue light) and up convert the spectrum of light of a lower energy than green (e.g., red, near IR, and IR light). Similarly, the blue paint or ink has color shifting particles which down convert the spectrum of light of a higher energy than blue (e.g., a UV light) and up convert the spectrum of light of a lower energy than blue (e.g., green, red, near IR, and IR light).

Cosmetic Products:

Cosmetics are substances used to enhance the appearance or odor of the human body. Cosmetics include but are not limited to skin-care creams, lotions, powders, perfumes, lipsticks, fingernail and toe nail polish, eye and facial makeup, permanent waves, colored contact lenses, hair colors, hair sprays and gels, deodorants, baby products, bath oils, bubble baths, bath salts, butters and many other types of products. A subset of cosmetics is called "make-up," which refers primarily to colored products intended to alter the user's appearance. Many manufacturers distinguish between decorative cosmetics and care cosmetics.

In one aspect of the invention, the color mixtures described above are included in those cosmetics that are intended to alter the user's appearance. In one aspect of the invention, the color mixtures described above are included in those cosmetics that are used to protect the body from the harmful UV aging effects.

Accordingly, those products where the color mixtures described above would be suitable for inclusion include but are not limited to lipstick, lip gloss, lip liner, lip plumper, lip balm, lip conditioner, lip primer, and lip boosters. Those products further include foundation, used to smooth out the face and cover spots or uneven skin coloration, usually a liquid, cream, or powder. Those products further include powders, used to give a matte finish, and also to conceal small flaws or blemishes. Those products further include rouge, blush or blusher, cheek coloring used to bring out the color in the cheeks and make the cheekbones appear more defined. Those products further include bronzers, used to give skin a bit of color by adding a golden or bronze glow. Those products further include mascara used to darken, lengthen, and thicken the eyelashes (available in natural colors such as brown and black, but also comes in bolder colors such as blue, pink, or purple). Those products further include eye liners, eye shadows, eye shimmers, and glitter eye pencils as well as different color pencils used to color and emphasize the eyelids, eyebrow pencils, creams, waxes, gels and powders used to color and define the brows. Those products further include nail polish, used to color the fingernails and toenails. Those products further include concealers and makeup used to cover any imperfections of the skin.

Also included in the general category of cosmetics are skin care products. These include creams and lotions to moisturize the face and body, sunscreens to protect the skin from damaging UV radiation, and treatment products to repair or hide skin imperfections (acne, wrinkles, dark circles under eyes, etc.). Cosmetics can be liquid or cream emulsions; powders, both pressed and loose; dispersions; and anhydrous creams or sticks.

In this application area, the color mixtures of the invention can both provide color shifting capability (as detailed above), but can also moderate UV light damage to skin or hair exposed to UV light irradiation. The cosmetics in this way can additionally or optionally provide a protective coating which has a mixture of light scattering and light emitting particles configured, upon exposure to UV light, to convert a first part of the UV light into visible light, emit from the mixture a fraction of the visible light, and reflect from the mixture a second part of the UV light such that the second part of the UV light is not absorbed by the skin or hair.

For example, while not limited to the details described below, UV light from the sun incident on the protective coating could have 50% or more of the UV light reflected due to the index of refraction change between air and the protective coating. That part of the UV light entering the interior layers of the protective coating converted into visible light. Other parts of the UV light would be scattered from protective coating and not incident on the underlying surface.

Regardless, the color shifting mixtures of the invention can include a cosmetically acceptable medium compatible with all skin, lip, or hair materials with which it comes into contact with. When these composition are to be applied in the form of an emulsion, the composition may optionally additionally include a surfactant, preferably in a quantity of 0 to 30% by weight, preferably from 0.01 to 30% by weight based on the total weight of the composition. The emulsion may be a single or multiple emulsion. The color shifting mixtures of the invention may be present in any one or more of these phases.

According to the application envisaged, the composition may also additionally include at least one film-forming polymer, in particular for mascaras, eyeliner or hair compositions of the lacquer type. The polymer may be dissolved or dispersed in a cosmetically acceptable medium and possibly associated with at least one coalescing agent and/or at least one plasticizer. The composition according to the invention may also include a fat phase that contains in particular at least one liquid fat and/or at least one fat that is solid at ambient temperature and atmospheric pressure. Liquid fats, often called oils, may constitute 0 to 90%, preferably 0.01 to 85% by weight based on the total weight of the fat phase. Solid or pasty fats may be chosen in particular from waxes, gums and mixtures thereof. The composition may contain 0 to 50%, preferably 0.01 to 40%, and in particular 0.1 to 30% by weight of solid or pasty fats based on the total weight of the composition.

The composition according to the invention may additionally include 0 to 30%, preferably 0.01 to 35% by weight of other particles based on the total weight of the composition. These particles may in particular be a pigment other than the color mixtures of the invention, a pearl pigment or a filler. The presence of these other particles makes it possible in particular to make the composition opaque.

In addition, the composition according to the invention may include ingredients conventionally present in such compositions, such as preservatives, antioxidants, thickeners, perfumes, moisturizing agents, sun filters, essential oils, vegetable extracts and vitamins.

In one embodiment of the invention, the color shifting mixtures of the invention can be used in shampoos, conditioners, gels, styling compounds, sprays, and other beauty products. In one embodiment of the invention, the color shifting mixtures of the invention are added to these hair and beauty products to increase the sheen of one's hair for example. The sheen in one's hair is a property of the surface finish of the hair and the scattering of the light at the top surfaces. Standard hair treatments "repair" i.e., fill the surfaces torn in the hair by aging, excessive washing, etc. In this embodiment of the invention the color converters in the hair treatments also fill into the broken surfaces. The effect would be to provide a surface of the hair which reflects more visible light and also has less diffusive scatter, by the filing and smoothing of the surfaces.

The color shifting mixtures of the invention can include (in addition to the up converters and down converters described herein) a number of other emulsions and conditioning agents such as described in U.S. Pat. Appl. No. 2005/0136258, U.S. Pat. Appl. No. 2005/0265935, U.S. Pat. Appl. No. 2006/0083762, U.S. Pat. Appl. No. 2006/0165621, U.S. Pat. Appl. No. 2007/0274938, and U.S. Pat. No. 7,608,237, the entire contents of each of these patent documents are incorporated herein by reference.

Displays:

In a conventional electronic ink display, i.e. an electrophoretic display, titanium dioxide particles approximately one micrometer in diameter are dispersed in a hydrocarbon oil. A dark-colored dye is also added to the oil, along with surfactants and charging agents that cause the particles to take on an electric charge. This mixture is placed between two parallel, conductive plates are typically separated by a gap of 10 to 100ΦDm. Upon applying a voltage the two plates, the particles will migrate electrophoretically to the plate bearing the opposite charge from that on the particles. When the particles are located at the front (viewing) side of the display, it appears white, because light is scattered back to the viewer by the high-index "white" titanium dioxide particles. When the particles are located at the rear side of the display, the display appears dark, because the incident light is absorbed by the colored dye. If the rear electrode is divided into a number of small picture elements (pixels), then an image can be formed by applying the appropriate voltage to each region of the display to create a pattern of reflecting and absorbing regions.

U.S. Pat. Appl. Publ. No. 20040257330 (the entire contents of which are incorporated herein by reference) describes details of formation of a conventional electronic ink display that would be applicable to the base components depicted in the displays of this invention. U.S. Pat. Appl. Publ. No. 20040257330 describes for example that it is possible to use a liquid filling the pixel cells, which is high insulative and colorless and transparent, including: aromatic hydrocarbons, such as toluene, xylene, ethylbenzene and dodecylbenzene; aliphatic hydrocarbons, such as hexane, cyclohexane, kerosine, normal paraffin and isoparaffin; halogenated hydrocarbons, such as chloroform, dichloromethane, pentachloromethane, tetrachloroethylene, trifluoroethylene and tetrafluoroethylene, various natural or synthetic oils, etc. These may be used singly or in mixture of two or more species.

A dispersion liquid can be used which may be colored with oil soluble dye having a color of R (red), G (green), B (blue), C (cyan), M (magenta), Y (yellow), etc. Examples of the dye may preferably include azo dyes, anthraquinone dyes, quinoline dyes, nitro dyes, nitroso dyes, penoline dyes, phthalocyanine dyes, metal complex salt dyes, naphthol dyes, benzoquinone dyes, cyanine dyes, indigo dyes, quinoimine dyes, etc. These may be used in combination. Examples of the oil soluble dye may include Vari Fast Yellow (1101, 1105, 3108, 4120), Oil Yellow (105, 107, 129, 3G, GGS), Vari Fast Red (1306, 1355, 2303, 3304, 3306, 3320), Oil Pink 312, Oil Scarlet 308, Oil Violet 730, Vari Fast Blue (1501, 1603, 1605, 1607, 2606, 2610, 3405). Oil Blue (2N, BOS, 613), Macrolex Blue RR, Sumiplast Gren G, Oil Green (502, BG), etc. A concentration of these dyes may preferably be 0.1-3.5 wt. %.

At the particle surface of the electrophoretic particles in the pixels, at least an amphipathic residual group derived from a reactive surfactant is fixed. Particles used for reaction may include organic or inorganic particles, pigment particles coated with a polymer, and polymer particles coated with a dye. An average particle size of these particles may be 10 nm to 5 μm, preferably 15 nm to 2 μm.

Examples of organic pigments which can be used in the pixel cells include azo pigments, phthalocyanine pigments, quinacridone pigments, isoindolinone pigments isoindolin pigments, dioazine pigments, perylene pigments, perinone pigments, thioindigo pigments, quinophthalone pigments, anthraquinone pigments, nitro pigments, and nitroso pigments. Specific examples thereof may include: rod pigments, such as Quinacridone Red, Lake Red, Brilliant Carmine, Perylene Red, Permanent Red, Toluidine Red and Madder Lake; green pigments, such as Diamond Green Lake, Phthalocyanine Green, and Pigment Green; blue pigments, such as Victoria Blue Lake, Phthalocyanine Blue, and Fast Sky Blue; yellow pigments, such as Hansa Yellow, Fast Yellow, Disazo Yellow, Isoindolinone Yellow, an Quinophthalone Yellow; and black pigments, such as Aniline Block and Diamond Black.

Examples of the inorganic pigments which can be used in the pixel cells include: white pigments, such as titanium oxide, aluminum oxide, zinc oxide, lead oxide, and zinc sulfide; black pigments, such as carbon black, manganese ferrite block, cobalt ferrite black, and titanium black; red pigments, such as cadmium red, red iron oxide, and molybdenum red; green pigments, such as chromium oxide, viridian, titanium cobalt green, cobalt green, and victoria green; blue pigments, such as ultramarine blue, prussian blue, and cobalt blue; and yellow pigments, such as cadmium yellow, titanium yellow, yellow iron oxide, chrome yellow, and antimony yellow.

As the pigment particles coated with a polymer, it is possible to use particles of the above described pigments coated with a polymer, such as polystyrene, polyethylene, polymethylacrylate, and polymethylmethacrylate. Coating of the pigment particles with the polymer may be performed by using a known method such as a polymer precipitation method or suspension polymerization.

As the polymer particles colored with a dye, it is possible to use particles of preliminarily synthesized crosslinkable polymer fine particles colored with a dye, particles obtained through suspension polymerization or emulsion polymerization of a polymerizable monomer containing a dye, etc.

In the electrophoretic particles to which surface at least the reactive surfactant-derived amphipathic residual group can be fixed, when the reactive surfactant is adsorbed by the particle surface and co-polymerized, a comonomer to be co-polymerized with the reactive surfactant is solubilized in the adsorption layer and polymerized or co-polymerized with the use of a polymerization initiator. As a result, the reactive surfactant-derived amphipathic residual group can be fixed at the particle surface.

Specific formulation procedures described in U.S. Pat. Appl. Publ. No. 20040257330 are suitable for this invention. Accordingly, in this invention, white electrophoretic particles and a dispersion medium colored with a blue dye can be filled in a pixel cell. The electrophoretic particles can be positively charged by fixing an amphipathic residual group derived from a reactive surfactant having a cationic functional group. When an electric field E is applied to the electrophoretic liquid, the positively charged electrophoretic particles are moved toward the upper side of the cell and distributed over the upper display surface. As a result, when the cell is observed from above, the cell looks white due to distribution of the white electrophoretic display. On the other hand, when the electric field E is applied to the electrophoretic liquid in an opposite direction, white electrophoretic particles are moved toward the bottom of the cell and distributed thereover, so that the cell looks blue when observed from above.

Accordingly, in this invention, a colorless dispersion medium and two types (white and black) of electrophoretic particles can be included in a pixel cell. The white electrophoretic particles are positively charged by fixing an amphipathic residual group derived from a reactive surfactant having a cationic functional group, and the black electrophoretic particles are negatively charged by fixing an amphipathic residual group derived from an anionic functional group. When an electric field E is applied to the electrophoretic liquid, the positively charged white electrophoretic particles are moved toward the upper side of the cell and the negatively charged black electrophoretic particles 1 e are moved toward the lower (bottom) side of the cell. As a result, when the cell is observed from above, the cell looks white due to distribution of the white electrophoretic display. On the other hand, when the electric field E is applied to the electrophoretic liquid in the opposite direction, the black electrophoretic particles are moved toward the upper side of the cell, and the white electrophoretic particles are moved toward the bottom of the cell, so that the cell looks black when observed from above.

U.S. Pat. Appl. Publ. No. 20040257330 describes for example a surfactant synthesis example where 4.8 g (41 mmol) of chlorosulfuric acid was gradually added dropwise to 35 ml of pyridine cooled at 0° C., followed by stirring for 30 minutes. To the reactive mixture, 9 ml of a pyridine solution containing 7.0 g (41 mmol) of 10-undecene alcohol was gradually added dropwise, followed by stirring for 1 hour at 0° C. and further stirring for 20 hours at 55° C. The reaction mixture was poured into a saturated sodium hydrogen-carbonate aqueous solution cooled at 0° C., and stirred for 1 hour and further stirred of 20 hours at room temperature. After the reaction, the solvent of the reaction mixture was distilled off under reduced pressure. To the residue, acetone was added to precipitate a crystal. The crystal was dissolved in methanol and thereafter, a methanol insoluble content was removed, followed by removal of the solvent under reduced pressure to obtain a crystal. The crystal was recrystallized from a mixture solvent (methanol/acetone=1/3) to obtain a reactive surfactant having an anionic functional group represented by the following formula (Yield: 80%).

CH2=CH—(CH2)9-OSO3Na

As a result of 1H-NMR (400 MHz, CD 3, OD) of the resultant reactive surfactant, measured values (δ/ppm) including 1.33 (12H), 1.68 (2H), 2.02 (2H), 4.00 (2H), 4.95 (2H) and 5.83 (1H) were obtained, thus identifying synthesis of the objective reactive surfactant (33).

U.S. Pat. Appl. Publ. No. 20040257330 describes thereafter the process for making a pixel solution, 5 wt. parts of titanium oxide and 3 wt. parts of the reactive surfactant prepared in the synthesis example above were added in 100 wt. parts of water, followed by irradiation of ultrasonic wave to form a bimolecular adsorption layer of the reactive surfactant at the surface of titanium oxide particles.

To the above treated particles, 2 wt. parts of di-n-butyl fumarate and 0.05 wt. part of potassium persulfate were added, followed by polymerization reaction for 48 hours at 60° C. in a nitrogen atmosphere. After coarse particles contained in the reaction mixture were removed with a filter, objective particles contained in the removed with a filter, objective particles contained in the reaction mixture were separated by centrifugation. The resultant precipitate was repeatedly recovered by filtration and washed, followed by drying to obtain particles to which the reactive surfactant-derived amphipathic residual group was fixed at the particle surface.

The obtained particles were subjected to salt exchange reaction by using a methanol solution o of n-hexadecyltrimethylammonium hydride (C16H33(CH3)3NOH), followed by washing of excessive ions with acetonitrile to obtain objective electrophoretic particles.

An electrophoretic liquid was prepared by dispersing 5 wt. parts of the electrophoretic particles in 50 wt. parts of isoparaffin ("Isopar H", mfd. by Exxon Corp.) colored blue by the addition of 0.1 wt. part of a dye ("Oil Blue N", mfd. by Aldrich Corp.). The prepared electrophoretic liquid was filled and sealed in a plurality of cells In this invention, the particles in U.S. Pat. Appl. Publ. No. 20040257330 (e.g., the titanium oxide) would be replaced with a mixture of color emitting particles or larger microscopic particle of the titanium oxide would be coated with nano-meter size mixtures of the color emitters of the invention.

Figure 9A:
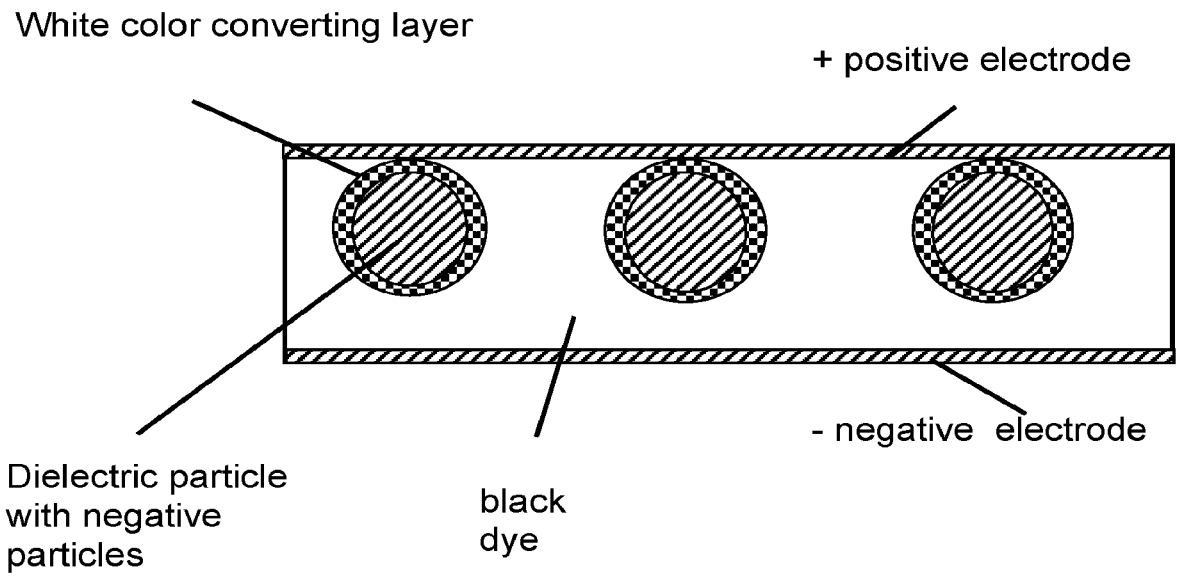
FIGS. 9A-9D are schematic representations of an electronic ink display using the color shifting particles of this invention.

FIG. 9A shows one example of an electronic ink display where a white color converting layer is applied for example to dielectric (e.g., titanium dioxide) particles. Here, depending on the voltage state of a pixel, the "white particles" in the black or dark dye are either drawn up to the near surface of the top electrode where white light is reflected or are repelled face the top electrode where the black dye, not at the near surface of the top electrode, absorbs incident light. The contrast then depends on the amount of light reflected from the "white particles" as opposed to the light not reflected from the blue dye. Here, in this embodiment, the dielectric particles include the color shifting particles of this invention to produce more white light by up converting of the infrared part of the spectrum and down converting of the UV part of the spectrum.

Upon reversing the charge on the top electrode, the dielectric particles is attracted to the bottom electrode, and little if any light is reflected. Thus, the voltage state of each pixel thus determines whether that pixel appears white or black to the observer on the top side.

The excitation light for the display shown in FIG. 9 may be an ultraviolet light source or a black body or solar source (having wavelengths in the ultraviolet), in accordance with various embodiments of the invention. If the excitation light is ultraviolet light, then when the light emitting material emits visible light in response to the ultraviolet light, a down-conversion physical phenomenon occurs. Specifically, ultraviolet light has a shorter wavelength and higher energy than visible light. Accordingly, when the light emitting material absorbs the ultraviolet light and emits lower energy visible light, the ultraviolet light is down-converted to visible light because the ultraviolet light's energy level decreases when it is converted into visible light. In embodiments, the light emitting material is fluorescent material.

The excitation light for the display shown in FIG. 9 may be infrared light source or a black body or solar source (having wavelengths in the infrared), in accordance with various embodiments of the invention. If the excitation light is infrared light, then when the light emitting material emits visible light in response to the infrared light, an up-conversion physical phenomenon occurs. Specifically, infrared light has a longer wavelength and lower energy than visible light. Accordingly, when the light emitting material absorbs the infrared light and emits higher energy visible light, the infrared light is up-converted to visible light because the infrared light's energy level increases when it is converted into visible light. Accordingly, in down-conversion embodiments, when ultraviolet light is absorbed by light emitting particles on the blue dye, visible light is emitted from the light emitting particles. Likewise, in up-conversion embodiments, when infrared light is absorbed by light emitting particles, visible light is emitted from the light emitting particles.

The size of the particles in the white light converting layer may be smaller than the wavelength of visible light, which may reduce or eliminate visible light scattering by the particles. Examples of particles that are smaller than the wavelength of visible light are nanoparticles or molecules. According to these embodiments, each of the light emitting particles could have a diameter that is less than about 500 nanometers. According to these embodiments, each of the light emitting particles could have a diameter that is less than about 400 nanometers. According to embodiments, each of the light emitting particles could have s a diameter that is less than about 300 nanometers. According to these embodiments, each of the light emitting particles could have a diameter that is less than about 200 nanometers. According to these embodiments, each of the light emitting particles could have a diameter that is less than about 100 nanometers. The light emitting particles may be individual molecules.

Figure 9B:
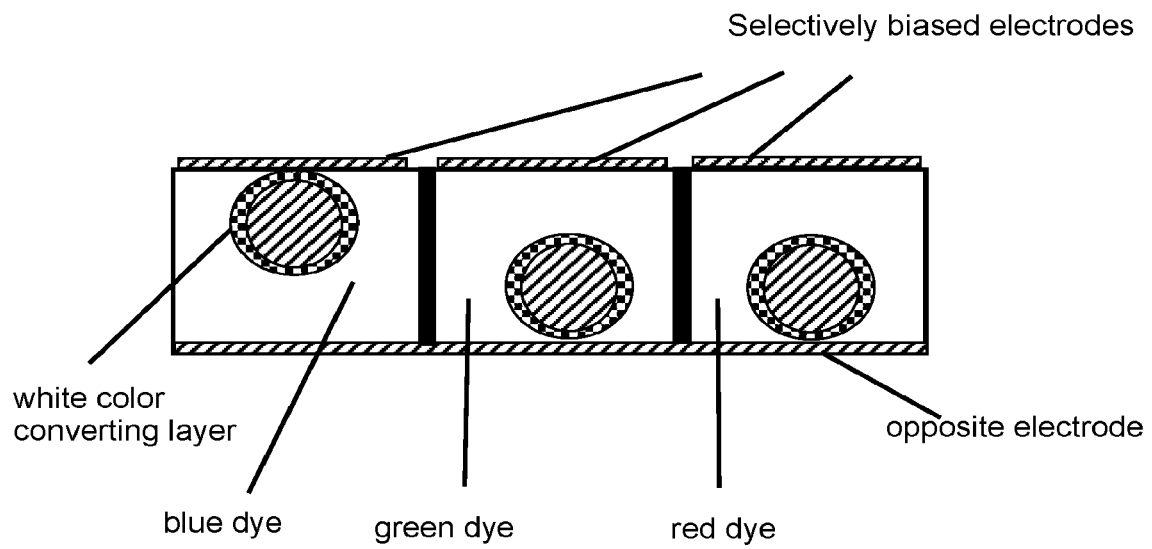

Different types of light emitting particles may be used together that have different physical characteristics. For example, in order to emit color images from selected pixels of the display of FIG. 9B, for example, different types of dyes may be utilized in pixels associated with different colors. FIG. 9B shows three pixels including respectively, red, green and blue dyes. When the top electrode attracts the dielectric particles with the white color enhancing layers to the top surface, the dye molecules in those pixels are displaced, turning that particular pixel the color of the dye. In one embodiment of the invention, the dyes (similar to the inks described below) contain nanoparticles of the color-shifting mixtures.

For example, a first type of light emitting particles may be associated with the color red, a second type of light emitting particles may be associated with the color green, and a third type of light emitting particles may be associated with the color blue. Although the example first type, second type, and third type of light emitting particles are primary colors, other combinations of colors (e.g. types of colors and number of colors) can be used to facilitate a color display.

Figure 9C:
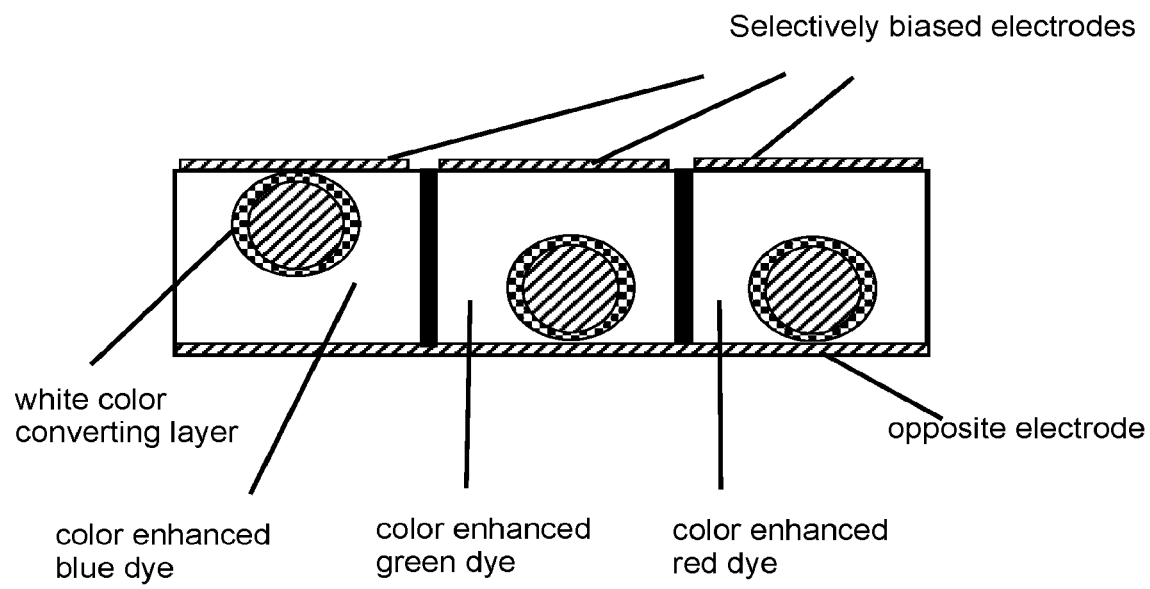

FIG. 9C shows another embodiment in which three pixels include respectively, red, green and blue dyes where the dyes themselves have contain the color-shifting (and thus color enhancing) mixtures. When the top electrode attracts the dielectric particles with the white color enhancing layers to the top surface, the dye molecules in those pixels are displaced, turning that particular pixel the color of the color-enhanced dye. In one embodiment of the invention, the dyes (similar to the inks described below) contain nanoparticles of the color-shifting mixtures.

Figure 9D:
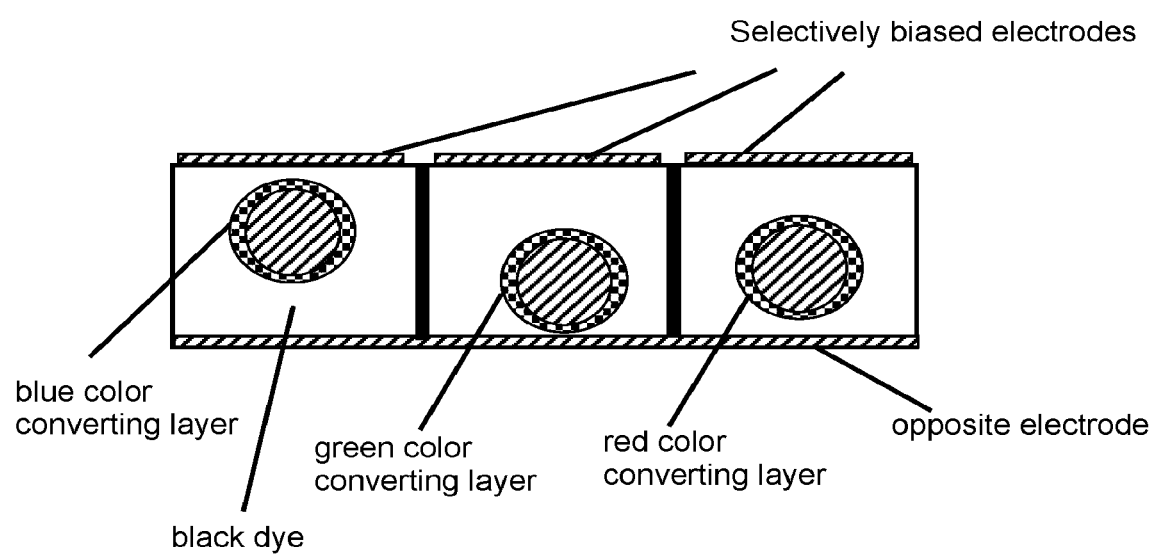

FIG. 9D shows another embodiment in which three pixels include dielectric particles with respectively, red, green and blue color enhancing layers. When the top electrode attracts the dielectric particles with the distinct color enhancing layers to the top surface, the dye molecules in those pixels are displaced, turning that particular pixel the color of the dielectric particle's converting layer.

Figure 10A:
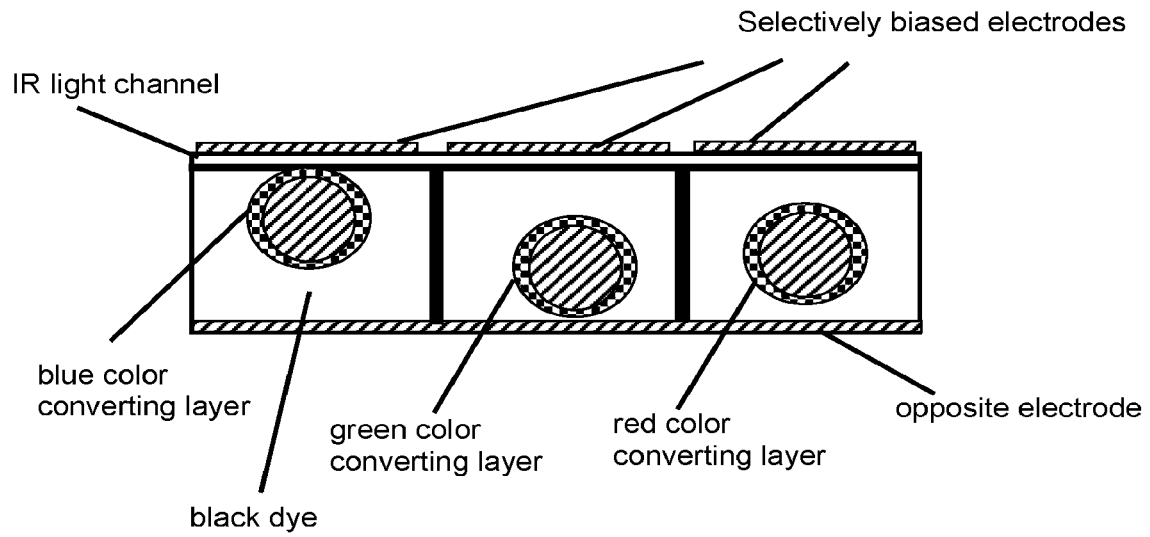
FIGS. 10A-10C are schematic representations of IR light activated displays using the color shifting particles of this invention.

FIG. 10A shows one example of an IR light activated display of the invention. Accordingly, in this embodiment, a display can be produced utilizing color shifting particles of different upconversion color emission characteristics segregated into different display pixels.

In this embodiment, an IR laser illuminates a near surface of a pixilated surface having the color shifting particles attracted thereto (by selectively biasing separate pixels). In one embodiment, IR light is emitted so as to undergo total internal reflection along the interior surface of the IR light channel plate. For the IR light channel plate, typically crystalline materials are transparent in the of 980 nm (NIR) light range; quartz, glass, $Y_2O_3$, etc. Also, small polymers (length/molecular weight) can also be transmissive but transmission in the range of IR is dependent on type and length etc.

In one embodiment, the IR light channel plate contains within itself scattering centers which scatter light off axis so as to illuminate a portion of the pixel region close to the IR light channel plate. In the example shown in FIG. 10, an IR light channel provides IR light propagation across the pixilated surface. The IR light in this example only stimulates the blue color converting layer, as the bias electrode above the blue pixel has attracted the blue color converting layer (e.g., with negative particles) to the near surface, while the red and green color converting layers are repelled.

Different types of light emitting particles may absorb different ranges of excitation light to emit the different colors. Accordingly, the wavelength range of the excitation light may be modulated in order to control the visible color emitted from the light emitting particles. In embodiments, different types of light emitting particles may be mixed together and integrated into/onto a substrate or in the dyes or inks of the pixel. By modulating the wavelength of the excitation light, along with spatial modulation and intensity modulation of the excitation light, visible light with specific color characteristics can be created in substrate. For example, by selectively exciting specific combinations of different types of light emitting particles associated with primary colors, virtually any visible color can be emitted.

Figure 10B:
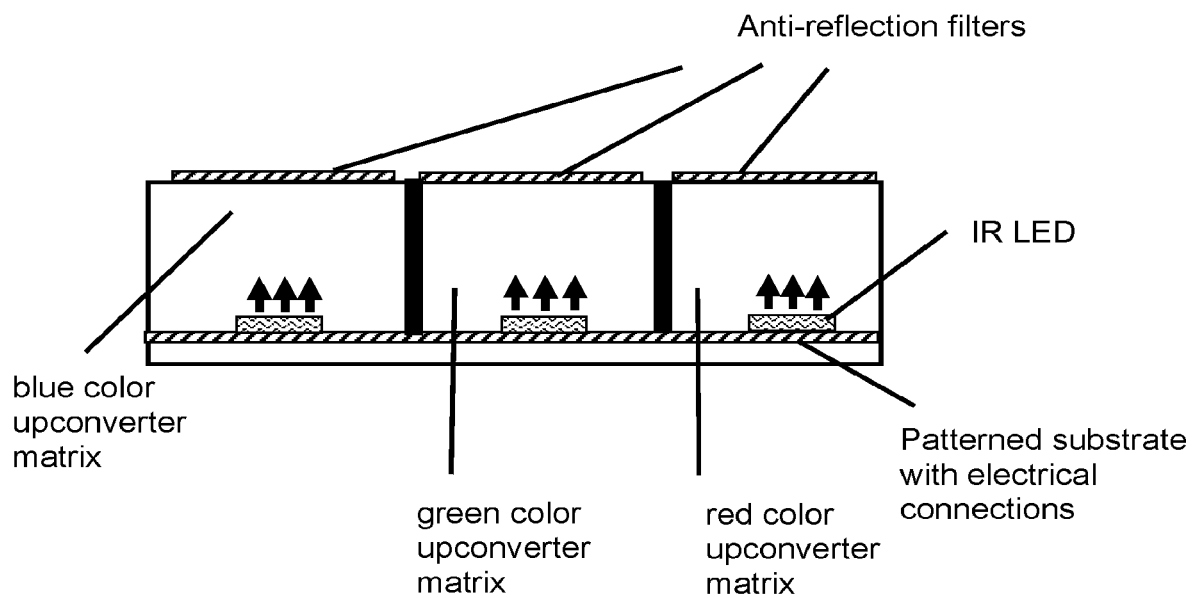

FIG. 10B shows another example of an IR light activated display of the invention. In this embodiment, infrared light emitting diodes are patterned on a substrate. The pattern of diodes are registered with a pattern of pixels. Each of the pixels contains a specific color emitter, for example a blue color upconverter matrix containing the color shifting mixtures of the invention.

In one embodiment, anti-reflective coatings or filters can be applied. For example, a reflective layer may be employed on surface opposite the LED light sources to reflect unconverted light back through the color shifting particle mixture. Indeed, as in laser cavity designs, this color pass filer would reflect light of the "wrong" unconverted wavelength back through the color shifting particle mixture for increased conversion.

U.S. Pat. No. 6,054,724 (the entire contents of which are incorporated herein by reference) describes ways to produce arrays of infrared light emitting diodes. The techniques described in that patent would be applicable for forming the patterned substrate containing the infrared light emitting LEDs shown in FIG. 10B. Alternatively, bonding technologies can be used to take diced laser diodes and mount laser diodes into the red, blue, and green pixel elements shown in FIG. 10B.

U.S. Pat. No. 6,104,740 (the entire contents of which are incorporated herein by reference) describes ways to produce arrays of infrared light emitting diodes and blue light emitting diodes on the same chip. The techniques described in that patent would be applicable for forming the patterned substrate containing the infrared light emitting LEDs shown in FIG. 10B. In this case, some of the light emitting LEDs would be blue light emitters, whose light could be either directly passed through the display or itself down converted.

Figure 10C:
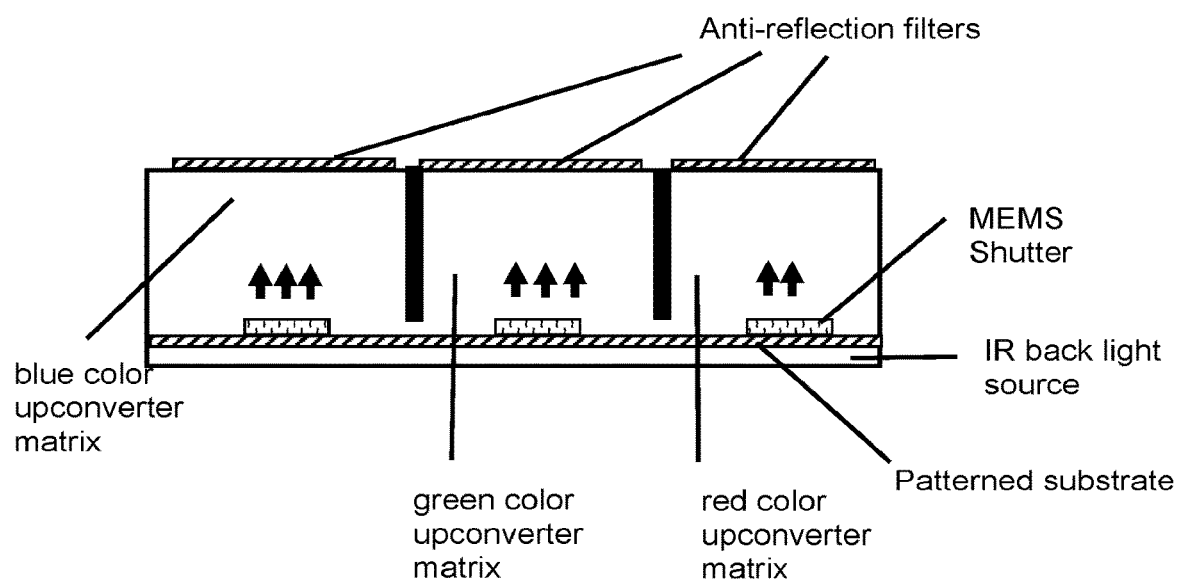

FIG. 10C shows another example of an IR light activated display of the invention. In this embodiment, microelectrical mechanical systems (MEMS) are patterned on a substrate. The MEMS devices contain shutters which when open allow IR light from a back light source to pass through holes in the substrate and illuminate respective pixels. Each of the pixels contains a specific color emitter, for example a blue color upconverter matrix containing the color shifting mixtures of the invention. The IR back light source may be a an infrared glow bar with appropriate filters or could be light diffused from an IR LED or IR laser source.

Figure 11:
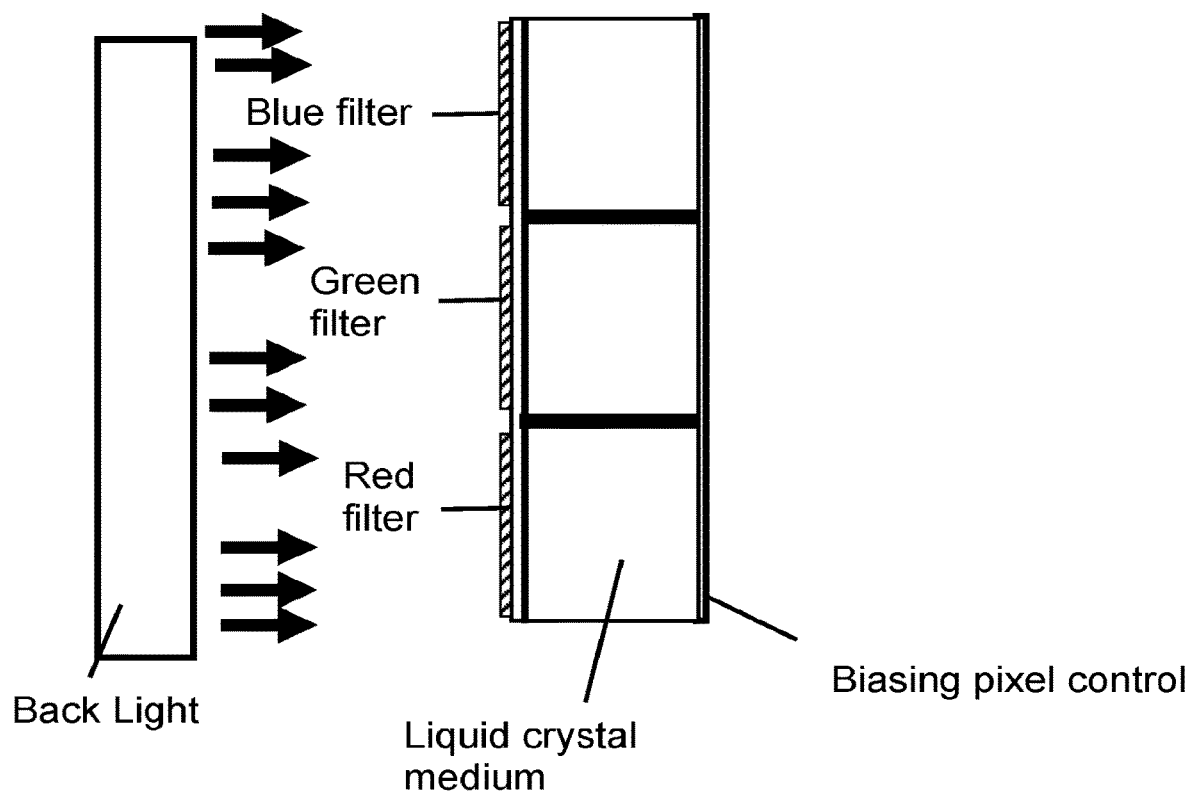
FIG. 11 is a schematic representation of a LCD light activated display in which the color filters have the color shifting particles of this invention.

FIG. 11 shows one example of a liquid crystal (LC) light activated display in which the color filters have the color shifting particles of this invention. In one embodiment of this invention, the color shifting particles can be employed in the color filter elements associated with conventional liquid crystal display technology. In this embodiment, light from a back light source passes through red, blue, and green color filters disposed in front of respective pixels of the liquid crystal display. Normally, light of the "wrong" color from the white back light would be merely absorbed making no contribution to the front side luminance of the display. With the color shifting particles of the invention, the white light for the red filter has color shifting particles which down convert the spectrum of light of a higher energy than red (e.g., a blue light) and up convert the spectrum of light of a lower energy than red (e.g., near IR and IR light). Similarly, the white light for the green filter has color shifting particles which down convert the spectrum of light of a higher energy than green (e.g., a blue light) and up convert the spectrum of light of a lower energy than green (e.g., red, near IR, and IR light). Similarly, the white light for the blue filter has color shifting particles which down convert the spectrum of light of a higher energy than blue (e.g., a UV light) and up convert the spectrum of light of a lower energy than blue (e.g., green, red, near IR, and IR light).

Similar principles would apply to reflective LCD structures where ambient light is passed through LC elements and reflected from colored surfaces back through the LC elements to be viewed. Here, the colored surfaces would have their respective reflected light luminance increased by color shifting particles which down convert the spectrum of light of a higher energy than red (e.g., a blue light) and up convert the spectrum of light of a lower energy than red (e.g., near IR and IR light) to reflect a higher luminance of red. Similarly, the white light for the green filter has color shifting particles which down convert the spectrum of light of a higher energy than green (e.g., a blue light) and up convert the spectrum of light of a lower energy than green (e.g., red, near IR, and IR light) to reflect a higher luminance of green. Similarly, the white light for the blue filter has color shifting particles which down convert the spectrum of light of a higher energy than blue (e.g., a UV light) and up convert the spectrum of light of a lower energy than blue (e.g., green, red, near IR, and IR light) to reflect a higher luminance of blue.

In various embodiments, reflective layers can be used at respective color pixels, and these reflective layers can be selective waveband reflective layers to compensate for varying emission efficiencies of different light emitting materials. For example, if light emitting materials that emit red light from the red pixel emit light at a higher intensity than light emitting materials from a blue pixel emit blue light, a selective waveband reflective layer may compensate for these differences in emission efficiencies. For example, a "blue" reflective layer may reflect blue light with a higher intensity than a "red" reflective layer reflects red light.

Aging Resistance:

Chalking, blistering, and cracking are common signs of the aging of latex and oil based paints. UV light exposure plays a significant role in the deterioration of paint pigments leading to these visual discrepancies. In one embodiment of the invention, UV light (and thus the energy contained in the UV light) is converted and/or scattered back away from a coated or painted or stained surface.

In this embodiment, a protective coating for moderating UV light damage to an object exposed to UV light irradiation is provided. The protective coating has a mixture of light scattering and light emitting particles configured, upon exposure to UV light, to convert a first part of the UV light into visible light, emit from the mixture a fraction of the visible light, and reflect from the mixture a second part of the UV light such that the second part of the UV light is not absorbed by said object.

For example, while not limited to the details described below, UV light from the sun incident on the protective coating could have 50% or more of the UV light reflected due to the index of refraction change between air and the protective coating. That part of the UV light entering the interior layers of the protective coating converted into visible light. Other parts of the UV light would be scattered from protective coating and would not be incident on the underlying surface.

Other Applications:

The color enhancing mixtures of the invention described above are applicable across a broad variety of artificially colored products. These products included (in addition to those products listed above) the following non-exhaustive list of products. For example, the color enhancing mixtures of the invention described above can be included in or on the surface of building products such as concrete products, asphalt, pavement, bathroom and kitchen tiles, structural tiles, pavers, bricks (e.g., as a glazing bricks) and other glazing or glazed products.

In one illustrative example, the color contrast of tennis court lines in day light or artificial light could be enhanced by the color mixtures of the present invention. Moreover, depending on the mixture additives which could include down converters targeted to for example a primary emission line in a plasma or arc discharge lamp, under artificial lighting (such as night-time lighting), the tennis pavement and the lines could exhibit a significant color change at nighttime, adding attraction to tennis as a night time sport.

Other products where the color enhancing mixtures would have value would be jewelry, rings, earrings, necklaces, braclets, mood rings, candles, epoxies, contact lens, rubber products, plastic products. Of particular example, contact lenses permit one to change their eye color. Besides adding the color enhancing mixtures of the invention to the typical colorants used in this product, the colorants can be added as the retroreflective glass spheres described above in order to produce a "cat-eyed" effect of reflecting light from a source more directionally to an observer.

U.S. Pat. No. 6,896,369 (the entire contents of which are incorporated herein by reference) describes the construction of colored contact lenses. In one embodiment of this invention, the color enhancing mixtures of the invention (with or without a retroreflective component) would be added to the multicolored pattern region having an epithelial region, a pupillary margin region, a collarette region, crypts of Fuchs elements, and a dilator pupillae region. These regions would have a plurality of colored elements or a combination of colored and non-colored elements. A colored element would be a colorant sufficiently opaque to mask the underlying region of the wearer's iris. An uncolored element would preferably clear, but may be slightly colored by a colorant which is sufficiently non-opaque so as not to mask the underlying region of the wearer's iris. To the colorants of U.S. Pat. No. 6,896,369, the color enhancing mixtures of the invention are added.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended claims, the invention may be practiced otherwise than as specifically described herein.

The invention claimed is:

1. A light display comprising:
   at least one of a color filter or a color reflective surface;
   color emitters included in the color filter or the color reflective surface, and including,
   first color emitters configured to emit, upon exposure to a light source, visible light at a target color in response to absorption of energy across a first band of wavelengths, and
   second color emitters configured to emit, upon exposure to the light source, visible light at the target color in response to absorption of energy across a second band of wavelengths, wherein a mixture of the first and second color emitters comprises a component of a color reflective surface of the display, and
   wherein light intensity observable at the target color is enhanced relative to reflected white light without emission from the first and second color emitters.

2. The display of claim 1, wherein the first target color and the second target color are the same.

3. The display of claim 1, wherein the first target color and the second target color are different.

4. The display of claim 1, wherein at least one of the first and second color emitters comprises light emitting particles having a diameter less than about 1000 nanometers.

5. The display of claim 4, wherein the light emitting particles comprise a particle having a metallic structure disposed in relation to the particle,
   wherein a physical characteristic of the metallic structure is set to a value where a surface plasmon resonance in the metallic structure resonates at a frequency which provides enhanced emission at the target color.

6. The display of claim 4, wherein a mixture of the first and second color emitters comprises at least one of red, blue, and green emitters configured to produce red, blue, and green emissions from an up conversion process.

7. The display of claim 1, wherein a mixture of the first and second color emitters is attached to dye molecule in a pixel of the display.

8. The display of claim 1, wherein a mixture of the first and second color emitters comprises a component of a color emitting pixel element of the display.

9. The display of claim 1, wherein a mixture of the first and second color emitters comprises a component of a color filter of the display.

10. The display of claim 1, wherein a mixture of the first and second color emitters comprises a component of a color filter for a display of the display.

11. The display of claim 1, wherein a mixture of the first and second color emitters comprises a component of a color surface of the display.

12. The display of claim 1, wherein a mixture of the first and second color emitters comprises a component of a color reflective surface in a pixel of the display.

13. The display of claim 1, wherein a mixture of the first and second color emitters comprises a component of a white-light emitting pixel display element of the display.

14. The display of claim 1, wherein a mixture of the first and second color emitters comprises at least one of red, blue, and green emitters configured to produce red, blue, and green emissions from an up conversion process.

15. The display of claim 1, wherein mixtures of the first and second color emitters comprise at least one of red, blue, and green emitters configured to produce red, blue, and green emissions from an up conversion process.

16. The display of claim 1, wherein a mixture of the first and second color emitters comprises at least one of red, blue, and green emitters configured to produce red, blue, and green emissions from a down conversion process.

17. The display of claim 1, wherein mixtures of the first and second color emitters comprises at least one of red, blue, and green emitters configured to produce red, blue, and green emissions from a down conversion process.

18. The display of claim 1, wherein a mixture of the first and second color emitters comprises at least one of red, blue, and green emitters configured to produce red, blue, and green emissions from a mixture of up converters and down converters.

19. The display of claim 1, wherein mixtures of the first and second color emitters comprises at least one of red, blue, and green emitters configured to produce red, blue, and green emissions from mixtures of up converters and down converters.

20. The display of claim 1, wherein a mixture of the first and second color emitters comprises a mixture of fluorescent emitters including at least one of europium, terbium, cerium, and erbium or combinations thereof.

21. The display of claim 1, wherein mixtures of the first and second color emitters comprise mixtures of fluorescent emitters including at least one of europium, terbium, cerium, and erbium or combinations thereof.

22. The display of claim 1, wherein at least one of the first or second color emitters comprises:
 a first material configured to emit a first visible color in response to absorption of ultraviolet light; and
 a second material configured to emit a second visible color in response to absorption of infrared light, wherein the second visible color is different from the first visible color.

23. The display of claim 22, further comprising a third material configured to emit a third visible color in response to absorption of the ultraviolet light, wherein the third visible color is different from the first visible color and the second visible color.

24. The display of claim 23, wherein the first visible color, the second visible color, and the third visible color are primary colors.

25. The display of claim 23, further comprising a third material configured to emit a third visible color in response to absorption of the infrared light, wherein the third visible color is different from the first visible color and the second visible color.

26. The display of claim 1, wherein at least one of the first or second color emitters comprises:
 a first material configured to emit a first visible color in response to absorption of ultraviolet light; and
 a second material configured to emit a second visible color in response to absorption of infrared light, wherein the second visible color is substantially the same color as the first visible color.

27. The display of claim 24, further comprising a third material configured to emit a third visible color in response to absorption of the ultraviolet light, wherein the third visible color is different from the first visible color and the second visible color.

28. The display of claim 24, further comprising a third material configured to emit a third visible color in response to absorption of the infrared light, wherein the third visible color is different from the first visible color and the second visible color.

29. The display of claim 28, wherein the first visible color, the second visible color, and the third visible color are at least two of the primary colors.

30. The display of claim 1, wherein at least one of the first and second color emitters comprises a metallic structure disposed in relation to a nanoparticle emitter.

31. The display of claim 30, wherein the metallic structure comprises a metallic shell having at least one of a spherical shell, an oblate shell, a crescent shell, a multilayer shell, a star-shaped shell, a cone-shaped shell, or a rod-shaped shell.

32. The display of claim 30, wherein said metallic structure comprises at least one of Au, Ag, Cu, Ni, Pt, Pd, Co, Ru, Rh, Al, Ga, or a combination or alloys or layers thereof.

33. The display of claim 30, wherein the nanoparticle emitter comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

34. The display of claim 33, wherein the nanoparticle comprises a dopant including at least one of Er, Eu, Yb, Tm, Nd, Tb, Ce, Y, U, Pr, La, Gd and other rare-earth species or a combination thereof.

35. The display of claim 34, wherein the dopant is included at a concentration of 0.01%-50% by mol concentration.

36. The display of claim 1, wherein at least one of the first and second color emitters comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; ZnS: Mn,$Er^{3+}$.

37. The display of claim 1, wherein at least one of the first and second color emitters comprises a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

38. The display of claim 37, wherein the dielectric up converter has a diameter ranging from at least one of 2-1000 nm, 2-100 nm, 2-50 nm, 2-20 nm, or 2-10 nm.

39. The display of claim 37, wherein:
 the dielectric up converter comprises a dopant including at least one of Er, Eu, Yb, Tm, Nd, Tb, Ce, Y, U, Pr, La, Gd and other rare-earth species or a combination thereof; and
 the dopant has a concentration of 0.01%-50% by mol concentration.

40. The display of claim 37, further comprising a metallic structure disposed in relation to the dielectric up converter, and the metallic structure includes at least one of Au, Ag, Cu, Ni, Pt, Pd, Co, Ru, Rh, Al, Ga, or alloys or layers thereof.

41. The display of claim 37, wherein the dielectric up converter is configured to exhibit visible emission upon interaction with NIR light.

42. The display of claim 1, wherein at least one of the first and second color emitters comprise an upconverter including at least one of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}:Cs_2NaGdCl_6$, $Nd^{3+}$, $Yb^{3+}$: $Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

43. A light display comprising:
 at least one of a color filter or a color reflective surface;
 color emitters included in the color filter or the color reflective surface, and including,
 first color emitters configured to emit, upon exposure to a light source, visible light at a target color in response to absorption of energy across a first band of wavelengths, and
 second color emitters configured to emit, upon exposure to the light source, visible light at the target color in response to absorption of energy across a second band of wavelengths,
 wherein a mixture of the first and second color emitters is attached to a dye molecule in a pixel of the display, wherein light intensity observable at the target color is enhanced relative to reflected white light without emission from the first and second color emitters.

44. The display of claim 43, wherein the first target color and the second target color are the same.

45. The display of claim 43, wherein the first target color and the second target color are different.

46. The display of claim 43, wherein at least one of the first and second color emitters comprises light emitting particles having a diameter less than about 1000 nanometers.

47. The display of claim 46, wherein the light emitting particles comprise a particle having a metallic structure disposed in relation to the particle,
wherein a physical characteristic of the metallic structure is set to a value where a surface plasmon resonance in the metallic structure resonates at a frequency which provides enhanced emission at the target color.

48. The display of claim 46, wherein a mixture of the first and second color emitters comprises at least one of red, blue, and green emitters configured to produce red, blue, and green emissions from an up conversion process.

49. The display of claim 43, wherein a mixture of the first and second color emitters comprises a component of a color emitting pixel element of the display.

50. The display of claim 43, wherein a mixture of the first and second color emitters comprises a component of a color filter of the display.

51. The display of claim 43, wherein a mixture of the first and second color emitters comprises a component of a color filter for a display of the display.

52. The display of claim 43, wherein a mixture of the first and second color emitters comprises a component of a color surface of the display.

53. The display of claim 43, wherein a mixture of the first and second color emitters comprises a component of a color reflective surface in a pixel of the display.

54. The display of claim 43, wherein a mixture of the first and second color emitters comprises at least one of red, blue, and green emitters configured to produce red, blue, and green emissions from an up conversion process.

55. The display of claim 43, wherein mixtures of the first and second color emitters comprise at least one of red, blue, and green emitters configured to produce red, blue, and green emissions from an up conversion process.

56. The display of claim 43, wherein a mixture of the first and second color emitters comprises at least one of red, blue, and green emitters configured to produce red, blue, and green emissions from a down conversion process.

57. The display of claim 43, wherein mixtures of the first and second color emitters comprises at least one of red, blue, and green emitters configured to produce red, blue, and green emissions from a down conversion process.

58. The display of claim 43, wherein a mixture of the first and second color emitters comprises at least one of red, blue, and green emitters configured to produce red, blue, and green emissions from a mixture of up converters and down converters.

59. The display of claim 43, wherein mixtures of the first and second color emitters comprises at least one of red, blue, and green emitters configured to produce red, blue, and green emissions from mixtures of up converters and down converters.

60. The display of claim 43, wherein a mixture of the first and second color emitters comprises a mixture of fluorescent emitters including at least one of europium, terbium, cerium, and erbium or combinations thereof.

61. The display of claim 43, wherein mixtures of the first and second color emitters comprise mixtures of fluorescent emitters including at least one of europium, terbium, cerium, and erbium or combinations thereof.

62. The display of claim 43, wherein at least one of the first or second color emitters comprises:
a first material configured to emit a first visible color in response to absorption of ultraviolet light; and
a second material configured to emit a second visible color in response to absorption of infrared light, wherein the second visible color is different from the first visible color.

63. The display of claim 62, further comprising a third material configured to emit a third visible color in response to absorption of the ultraviolet light,
wherein the third visible color is different from the first visible color and the second visible color.

64. The display of claim 63, wherein the first visible color, the second visible color, and the third visible color are primary colors.

65. The display of claim 63, further comprising a third material configured to emit a third visible color in response to absorption of the infrared light,
wherein the third visible color is different from the first visible color and the second visible color.

66. The display of claim 43, wherein at least one of the first or second color emitters comprises:
a first material configured to emit a first visible color in response to absorption of ultraviolet light; and
a second material configured to emit a second visible color in response to absorption of infrared light, wherein the second visible color is substantially the same color as the first visible color.

67. The display of claim 64, further comprising a third material configured to emit a third visible color in response to absorption of the ultraviolet light,
wherein the third visible color is different from the first visible color and the second visible color.

68. The display of claim 64, further comprising a third material configured to emit a third visible color in response to absorption of the infrared light,
wherein the third visible color is different from the first visible color and the second visible color.

69. The display of claim 68, wherein the first visible color, the second visible color, and the third visible color are at least two of the primary colors.

70. The display of claim 43, wherein at least one of the first and second color emitters comprises a metallic structure disposed in relation to a nanoparticle emitter.

71. The display of claim 70, wherein the metallic structure comprises a metallic shell having at least one of a spherical shell, an oblate shell, a crescent shell, a multilayer shell, a star-shaped shell, a cone-shaped shell, or a rod-shaped shell.

72. The display of claim 70, wherein said metallic structure comprises at least one of Au, Ag, Cu, Ni, Pt, Pd, Co, Ru, Rh, Al, Ga, or a combination or alloys or layers thereof.

73. The display of claim 70, wherein the nanoparticle emitter comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

74. The display of claim 73, wherein the nanoparticle comprises a dopant including at least one of Er, Eu, Yb, Tm, Nd, Tb, Ce, Y, U, Pr, La, Gd and other rare-earth species or a combination thereof.

75. The display of claim 74, wherein the dopant is included at a concentration of 0.01%-50% by mol concentration.

76. The display of claim 43, wherein at least one of the first and second color emitters comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS: Mn,$Er^{3+}$.

77. The display of claim 43, wherein at least one of the first and second color emitters comprises a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

78. The display of claim 77, wherein the dielectric up converter has a diameter ranging from at least one of 2-1000 nm, 2-100 nm, 2-50 nm, 2-20 nm, or 2-10 nm.

79. The display of claim 77, wherein:
the dielectric up converter comprises a dopant including at least one of Er, Eu, Yb, Tm, Nd, Tb, Ce, Y, U, Pr, La, Gd and other rare-earth species or a combination thereof; and
the dopant has a concentration of 0.01%-50% by mol concentration.

80. The display of claim 77, further comprising a metallic structure disposed in relation to the dielectric up converter, and the metallic structure includes at least one of Au, Ag, Cu, Ni, Pt, Pd, Co, Ru, Rh, Al, Ga, or alloys or layers thereof.

81. The display of claim 77, wherein the dielectric up converter is configured to exhibit visible emission upon interaction with NIR light.

82. The display of claim 43, wherein at least one of the first and second color emitters comprise an upconverter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$: $Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2$—$Ga_2O_3$—$R_2O$ (R=Li, Na, K) glasses, and metal-to-ligand charge transfer (MLCT) transition materials, and MLCT transition materials including [Ru(dmb)$_3$]$^{2+}$ (dmb=4,4"-dimethyl-2,2"-bipyridine).

83. A light display comprising:
at least one of a color filter or a color reflective surface;
color emitters included in the color filter or the color reflective surface, and including,
first color emitters configured to emit, upon exposure to a light source, visible light at a target color in response to absorption of energy across a first band of wavelengths, and
second color emitters configured to emit, upon exposure to the light source, visible light at the target color in response to absorption of energy across a second band of wavelengths,
wherein at least one of the first and second color emitters comprises light emitting particles having a diameter less than about 1000 nanometers,
wherein the light emitting particles comprise a particle having a metallic structure disposed in relation to the particle,
wherein a physical characteristic of the metallic structure is set to a value where a surface plasmon resonance in the metallic structure resonates at a frequency which provides enhanced emission at the target color wherein light intensity observable at the target color is enhanced relative to reflected white light without emission from the first and second color emitters.

84. The display of claim 83, wherein the first target color and the second target color are the same.

85. The display of claim 83, wherein the first target color and the second target color are different.

86. The display of claim 83, wherein a mixture of the first and second color emitters comprises at least one of red, blue, and green emitters configured to produce red, blue, and green emissions from an up conversion process.

87. The display of claim 83, wherein a mixture of the first and second color emitters comprises a component of a color emitting pixel element of the display.

88. The display of claim 83, wherein a mixture of the first and second color emitters comprises a component of a color filter of the display.

89. The display of claim 83, wherein a mixture of the first and second color emitters comprises a component of a color filter for a display of the display.

90. The display of claim 83, wherein a mixture of the first and second color emitters comprises a component of a color surface of the display.

91. The display of claim 83, wherein a mixture of the first and second color emitters comprises a component of a color reflective surface in a pixel of the display.

92. The display of claim 83, wherein a mixture of the first and second color emitters comprises a component of a white-light emitting pixel display element of the display.

93. The display of claim 83, wherein a mixture of the first and second color emitters comprises at least one of red, blue, and green emitters configured to produce red, blue, and green emissions from an up conversion process.

94. The display of claim 83, wherein mixtures of the first and second color emitters comprise at least one of red, blue, and green emitters configured to produce red, blue, and green emissions from an up conversion process.

95. The display of claim 83, wherein a mixture of the first and second color emitters comprises at least one of red, blue, and green emitters configured to produce red, blue, and green emissions from a down conversion process.

96. The display of claim 83, wherein mixtures of the first and second color emitters comprises at least one of red, blue, and green emitters configured to produce red, blue, and green emissions from a down conversion process.

97. The display of claim 83, wherein a mixture of the first and second color emitters comprises at least one of red, blue, and green emitters configured to produce red, blue, and green emissions from a mixture of up converters and down converters.

98. The display of claim 83, wherein mixtures of the first and second color emitters comprises at least one of red, blue, and green emitters configured to produce red, blue, and green emissions from mixtures of up converters and down converters.

99. The display of claim 83, wherein a mixture of the first and second color emitters comprises a mixture of fluorescent emitters including at least one of europium, terbium, cerium, and erbium or combinations thereof.

100. The display of claim 83, wherein mixtures of the first and second color emitters comprise mixtures of fluorescent emitters including at least one of europium, terbium, cerium, and erbium or combinations thereof.

101. The display of claim 83, wherein at least one of the first or second color emitters comprises:
a first material configured to emit a first visible color in response to absorption of ultraviolet light; and a second material configured to emit a second visible color in response to absorption of infrared light, wherein the second visible color is different from the first visible color.

102. The display of claim 101, further comprising a third material configured to emit a third visible color in response to absorption of the ultraviolet light, wherein the third visible color is different from the first visible color and the second visible color.

103. The display of claim 102, wherein the first visible color, the second visible color, and the third visible color are primary colors.

104. The display of claim 101, further comprising a third material configured to emit a third visible color in response to absorption of the infrared light, wherein the third visible color is different from the first visible color and the second visible color.

105. The display of claim 83, wherein at least one of the first or second color emitters comprises:
a first material configured to emit a first visible color in response to absorption of ultraviolet light; and
a second material configured to emit a second visible color in response to absorption of infrared light, wherein the second visible color is substantially the same color as the first visible color.

106. The display of claim 105, further comprising a third material configured to emit a third visible color in response to absorption of the ultraviolet light, wherein the third visible color is different from the first visible color and the second visible color.

107. The display of claim 105, further comprising a third material configured to emit a third visible color in response to absorption of the infrared light, wherein the third visible color is different from the first visible color and the second visible color.

108. The display of claim 107, wherein the first visible color, the second visible color, and the third visible color are at least two of the primary colors.

109. The display of claim 83, wherein at least one of the first and second color emitters comprises a metallic structure disposed in relation to a nanoparticle emitter.

110. The display of claim 109, wherein the metallic structure comprises a metallic shell having at least one of a spherical shell, an oblate shell, a crescent shell, a multilayer shell, a star-shaped shell, a cone-shaped shell, or a rod-shaped shell.

111. The display of claim 109, wherein said metallic structure comprises at least one of Au, Ag, Cu, Ni, Pt, Pd, Co, Ru, Rh, Al, Ga, or a combination or alloys or layers thereof.

112. The display of claim 109, wherein the nanoparticle emitter comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

113. The display of claim 112, wherein the nanoparticle comprises a dopant including at least one of Er, Eu, Yb, Tm, Nd, Tb, Ce, Y, U, Pr, La, Gd and other rare-earth species or a combination thereof.

114. The display of claim 113, wherein the dopant is included at a concentration of 0.01%-50% by mol concentration.

115. The display of claim 83, wherein at least one of the first and second color emitters comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

116. The display of claim 83, wherein at least one of the first and second color emitters comprises a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

117. The display of claim 116, wherein the dielectric up converter has a diameter ranging from at least one of 2-1000 nm, 2-100 nm, 2-50 nm, 2-20 nm, or 2-10 nm.

118. The display of claim 116, wherein:
the dielectric up converter comprises a dopant including at least one of Er, Eu, Yb, Tm, Nd, Tb, Ce, Y, U, Pr, La, Gd and other rare-earth species or a combination thereof; and
the dopant has a concentration of 0.01%-50% by mol concentration.

119. The display of claim 116, further comprising a metallic structure disposed in relation to the dielectric up converter, and the metallic structure includes at least one of Au, Ag, Cu, Ni, Pt, Pd, Co, Ru, Rh, Al, Ga, or alloys or layers thereof.

120. The display of claim 116, wherein the dielectric up converter is configured to exhibit visible emission upon interaction with NIR light.

121. The display of claim 83, wherein at least one of the first and second color emitters comprise an upconverter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine).

122. A light display comprising:
at least one of a color filter or a color reflective surface;
color emitters included in the color filter or the color reflective surface, and including,
first color emitters configured to emit, upon exposure to a light source, visible light at a target color in response to absorption of energy across a first band of wavelengths, and
second color emitters configured to emit, upon exposure to the light source, visible light at the target color in response to absorption of energy across a second band of wavelengths,
wherein a mixture of the first and second color emitters comprises at least one of red, blue, and green emitters configured to produce red, blue, and green emissions from an up conversion process,
wherein light intensity observable at the target color is enhanced relative to reflected white light without emission from the first and second color emitters.

123. The display of claim 122, wherein the first target color and the second target color are the same.

124. The display of claim 122, wherein the first target color and the second target color are different.

125. The display of claim 122, wherein at least one of the first and second color emitters comprises light emitting particles having a diameter less than about 1000 nanometers.

126. The display of claim 122, wherein a mixture of the first and second color emitters comprises a component of a color emitting pixel element of the display.

127. The display of claim 122, wherein a mixture of the first and second color emitters comprises a component of a color filter of the display.

128. The display of claim 122, wherein a mixture of the first and second color emitters comprises a component of a color filter for a display of the display.

129. The display of claim 122, wherein a mixture of the first and second color emitters comprises a component of a color surface of the display.

130. The display of claim 122, wherein a mixture of the first and second color emitters comprises a component of a color reflective surface in a pixel of the display.

131. The display of claim 122, wherein a mixture of the first and second color emitters comprises a component of a white-light emitting pixel display element of the display.

132. The display of claim 122, wherein a mixture of the first and second color emitters comprises at least one of red, blue, and green emitters configured to produce red, blue, and green emissions from a down conversion process.

133. The display of claim 122, wherein mixtures of the first and second color emitters comprises at least one of red, blue, and green emitters configured to produce red, blue, and green emissions from a down conversion process.

134. The display of claim 122, wherein a mixture of the first and second color emitters comprises at least one of red, blue, and green emitters configured to produce red, blue, and green emissions from a mixture of up converters and down converters.

135. The display of claim 122, wherein a mixture of the first and second color emitters comprises a mixture of fluorescent emitters including at least one of europium, terbium, cerium, and erbium or combinations thereof.

136. The display of claim 122, wherein mixtures of the first and second color emitters comprise mixtures of fluorescent emitters including at least one of europium, terbium, cerium, and erbium or combinations thereof.

137. The display of claim 122, wherein at least one of the first or second color emitters comprises:
a first material configured to emit a first visible color in response to absorption of ultraviolet light; and
a second material configured to emit a second visible color in response to absorption of infrared light, wherein the second visible color is different from the first visible color.

138. The display of claim 137, further comprising a third material configured to emit a third visible color in response to absorption of the ultraviolet light, wherein the third visible color is different from the first visible color and the second visible color.

139. The display of claim 138, wherein the first visible color, the second visible color, and the third visible color are primary colors.

140. The display of claim 138, further comprising a third material configured to emit a third visible color in response to absorption of the infrared light, wherein the third visible color is different from the first visible color and the second visible color.

141. The display of claim 122, wherein at least one of the first or second color emitters comprises:
a first material configured to emit a first visible color in response to absorption of ultraviolet light; and
a second material configured to emit a second visible color in response to absorption of infrared light, wherein the second visible color is substantially the same color as the first visible color.

142. The display of claim 141, further comprising a third material configured to emit a third visible color in response to absorption of the ultraviolet light, wherein the third visible color is different from the first visible color and the second visible color.

143. The display of claim 141, further comprising a third material configured to emit a third visible color in response to absorption of the infrared light, wherein the third visible color is different from the first visible color and the second visible color.

144. The display of claim 143, wherein the first visible color, the second visible color, and the third visible color are at least two of the primary colors.

145. The display of claim 122, wherein at least one of the first and second color emitters comprises a metallic structure disposed in relation to a nanoparticle emitter.

146. The display of claim 145, wherein the metallic structure comprises a metallic shell having at least one of a spherical shell, an oblate shell, a crescent shell, a multilayer shell, a star-shaped shell, a cone-shaped shell, or a rod-shaped shell.

147. The display of claim 145, wherein said metallic structure comprises at least one of Au, Ag, Cu, Ni, Pt, Pd, Co, Ru, Rh, Al, Ga, or a combination or alloys or layers thereof.

148. The display of claim 145, wherein the nanoparticle emitter comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

149. The display of claim 145, wherein the nanoparticle emitter comprises a dopant including at least one of Er, Eu, Yb, Tm, Nd, Tb, Ce, Y, U, Pr, La, Gd and other rare-earth species or a combination thereof.

150. The display of claim 149, wherein the dopant is included at a concentration of 0.01%-50% by mol concentration.

151. The display of claim 122, wherein at least one of the first and second color emitters comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb $ZnS:Tb^{3+}$, $Er^{3+}$; $ZnS:Tb^{3+}$; $Y_2O_3:Tb^{3+}$; $Y_2O_3:Tb^{3+}$, $Er^{3+}$; $ZnS:Mn^{2+}$; $ZnS:Mn,Er^{3+}$.

152. The display of claim 122, wherein at least one of the first and second color emitters comprises a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

153. The display of claim 152, wherein the dielectric up converter has a diameter ranging from at least one of 2-1000 nm, 2-100 nm, 2-50 nm, 2-20 nm, or 2-10 nm.

154. The display of claim 152, wherein:
the dielectric up converter comprises a dopant including at least one of Er, Eu, Yb, Tm, Nd, Tb, Ce, Y, U, Pr, La, Gd and other rare-earth species or a combination thereof; and
the dopant has a concentration of 0.01%-50% by mol concentration.

155. The display of claim 152, further comprising a metallic structure disposed in relation to the dielectric up converter, and the metallic structure includes at least one of Au, Ag, Cu, Ni, Pt, Pd, Co, Ru, Rh, Al, Ga, or alloys or layers thereof.

156. The display of claim 37, wherein the dielectric up converter is configured to exhibit visible emission upon interaction with NIR light.

157. The display of claim 122, wherein at least one of the first and second color emitters comprise an upconverter including at least one of $Tm^{3+}$ doped flourozirconate glasses, $LuPO_4:Yb^{3+}$, $Tm^{3+}$, and $YbPO_4:Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}:Cs_2NaGdCl_6$, $Nd^{3+}$, $Yb^{3+}$: $Cs_2NaGdCl_6$, $Nd^{3+}$ and $Ho^{3+}$ co-doped-based $ZrF_4$ fluoride glasses, $Tm^{3+}/Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4-dimethyl-2,2-bipyridine).

158. A light display comprising:
at least one of a color filter or a color reflective surface;
color emitters included in the color filter or the color reflective surface, and including,
first color emitters configured to emit, upon exposure to a light source, visible light at a target color in response to absorption of energy across a first band of wavelengths, and
second color emitters configured to emit, upon exposure to the light source, visible light at the target color in response to absorption of energy across a second band of wavelengths,
wherein at least one of the first or second color emitters comprises:
a first material configured to emit a first visible color in response to absorption of ultraviolet light; and
a second material configured to emit a second visible color in response to absorption of infrared light, wherein the second visible color is either different from or substantially the same color as the first visible color,
wherein light intensity observable at the target color is enhanced relative to reflected white light without emission from the first and second color emitters.

159. The display of claim 158, wherein the first target color and the second target color are the same.

160. The display of claim 158, wherein the first target color and the second target color are different.

161. The display of claim 158, wherein at least one of the first and second color emitters comprises light emitting particles having a diameter less than about 1000 nanometers.

162. The display of claim 161, wherein a mixture of the first and second color emitters comprises at least one of red, blue, and green emitters configured to produce red, blue, and green emissions from an up conversion process.

163. The display of claim 158, wherein a mixture of the first and second color emitters comprises a component of a color emitting pixel element of the display.

164. The display of claim 158, wherein a mixture of the first and second color emitters comprises a component of a color filter of the display.

165. The display of claim 158, wherein a mixture of the first and second color emitters comprises a component of a color filter for a display of the display.

166. The display of claim 158, wherein a mixture of the first and second color emitters comprises a component of a color surface of the display.

167. The display of claim 158, wherein a mixture of the first and second color emitters comprises a component of a color reflective surface in a pixel of the display.

168. The display of claim 158, wherein a mixture of the first and second color emitters comprises a component of a white-light emitting pixel display element of the display.

169. The display of claim 158, wherein a mixture of the first and second color emitters comprises at least one of red, blue, and green emitters configured to produce red, blue, and green emissions from a down conversion process.

170. The display of claim 158, wherein mixtures of the first and second color emitters comprises at least one of red, blue, and green emitters configured to produce red, blue, and green emissions from a down conversion process.

171. The display of claim 158, wherein a mixture of the first and second color emitters comprises at least one of red, blue, and green emitters configured to produce red, blue, and green emissions from a mixture of up converters and down converters.

172. The display of claim 158, wherein a mixture of the first and second color emitters comprises a mixture of fluorescent emitters including at least one of europium, terbium, cerium, and erbium or combinations thereof.

173. The display of claim 158, wherein mixtures of the first and second color emitters comprise mixtures of fluorescent emitters including at least one of europium, terbium, cerium, and erbium or combinations thereof.

174. The display of claim 158, wherein the second visible color is different from the first visible color.

175. The display of claim 174, further comprising a third material configured to emit a third visible color in response to absorption of the ultraviolet light, wherein the third visible color is different from the first visible color and the second visible color.

176. The display of claim 175, wherein the first visible color, the second visible color, and the third visible color are primary colors.

177. The display of claim 175, further comprising a third material configured to emit a third visible color in response to absorption of the infrared light, wherein the third visible color is different from the first visible color and the second visible color.

178. The display of claim 158, wherein the second visible color is substantially the same color as the first visible color.

179. The display of claim 178, further comprising a third material configured to emit a third visible color in response to absorption of the ultraviolet light, wherein the third visible color is different from the first visible color and the second visible color.

180. The display of claim 178, further comprising a third material configured to emit a third visible color in response to absorption of the infrared light, wherein the third visible color is different from the first visible color and the second visible color.

181. The display of claim 180, wherein the first visible color, the second visible color, and the third visible color are at least two of the primary colors.

182. The display of claim 158, wherein at least one of the first and second color emitters comprises a metallic structure disposed in relation to a nanoparticle emitter.

183. The display of claim 182, wherein the metallic structure comprises a metallic shell having at least one of a spherical shell, an oblate shell, a crescent shell, a multilayer shell, a star-shaped shell, a cone-shaped shell, or a rod-shaped shell.

184. The display of claim 182, wherein said metallic structure comprises at least one of Au, Ag, Cu, Ni, Pt, Pd, Co, Ru, Rh, Al, Ga, or a combination or alloys or layers thereof.

185. The display of claim 182, wherein the nanoparticle emitter comprises at least one of $Y_2O_3$, $Y_2O_2S$, $NaYF_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, or SiO$_2$ or alloys or layers thereof.

186. The display of claim 185, wherein the nanoparticle comprises a dopant including at least one of Er, Eu, Yb, Tm, Nd, Tb, Ce, Y, U, Pr, La, Gd and other rare-earth species or a combination thereof.

187. The display of claim 185, wherein the dopant is included at a concentration of 0.01%-50% by mol concentration.

188. The display of claim 158, wherein at least one of the first and second color emitters comprises a down converter including at least one of Y$_2$O$_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:Tb$^{3+}$, Er$^{3+}$; ZnS:Tb$^{3+}$; Y$_2$O$_3$:Tb$^{3+}$; Y$_2$O$_3$:Tb$^{3+}$, Er$^{3+}$; ZnS:Mn$^{2+}$; ZnS: Mn,Er$^{3+}$.

189. The display of claim 158, wherein at least one of the first and second color emitters comprises a dielectric up converter including at least one of Y$_2$O$_3$, Y$_2$O$_2$S, NaYF$_4$, NaYbF$_4$, YAG, YAP, Nd$_2$O$_3$, LaF$_3$, LaCl$_3$, La$_2$O$_3$, TiO$_2$, LuPO$_4$, YVO$_4$, YbF$_3$, YF$_3$, Na-doped YbF$_3$, or SiO$_2$ or alloys or layers thereof.

190. The display of claim 189, wherein the dielectric up converter has a diameter ranging from at least one of 2-1000 nm, 2-100 nm, 2-50 nm, 2-20 nm, or 2-10 nm.

191. The display of claim 189, wherein:
the dielectric up converter comprises a dopant including at least one of Er, Eu, Yb, Tm, Nd, Tb, Ce, Y, U, Pr, La, Gd and other rare-earth species or a combination thereof; and
the dopant has a concentration of 0.01%-50% by mol concentration.

192. The display of claim 189, further comprising a metallic structure disposed in relation to the dielectric up converter, and the metallic structure includes at least one of Au, Ag, Cu, Ni, Pt, Pd, Co, Ru, Rh, Al, Ga, or alloys or layers thereof.

193. The display of claim 189, wherein the dielectric up converter is configured to exhibit visible emission upon interaction with NIR light.

194. The display of claim 158, wherein at least one of the first and second color emitters comprise an upconverter including at least one of Tm$^{3+}$ doped flourozirconate glasses, LuPO$_4$:Yb$^{3+}$, Tm$^{3+}$, and YbPO$_4$:Er$^{3+}$ nanocrystals, tellurium and germanium oxides, tellurium and germanium oxides doped with at least one Tm, Yb, Ho, Er, or Pr, Yb$^{3+}$ doped BaZrO$_3$, Nd$^{3+}$:Cs$_2$NaGdCl$_6$, Nd$^{3+}$, Yb$^{3+}$: Cs$_2$NaGdCl$_6$, Nd$^{3+}$ and Ho$^{3+}$ co-doped-based ZrF$_4$ fluoride glasses, Tm$^{3+}$/Yb$^{3+}$-codoped TeO$_2$—Ga$_2$O$_3$—R$_2$O (R=Li, Na, K) glasses, and metal-to-ligand charge transfer (MLCT) transition materials, and MLCT transition materials including [Ru(dmb)$_3$]$^{2+}$ (dmb=4,4-dimethyl-2,2-bipyridine).

195. A light display comprising:
at least one of a color filter or a color reflective surface;
color emitters included in the color filter or the color reflective surface, and including,
first color emitters configured to emit, upon exposure to a light source, visible light at a target color in response to absorption of energy across a first band of wavelengths, and
second color emitters configured to emit, upon exposure to the light source, visible light at the target color in response to absorption of energy across a second band of wavelengths,
wherein at least one of the first and second color emitters comprises a metallic structure disposed in relation to a nanoparticle emitter,
wherein the metallic structure comprises a metallic shell having at least one of a spherical shell, an oblate shell, a crescent shell, a multilayer shell, a star-shaped shell, a cone-shaped shell, or a rod-shaped shell,
wherein light intensity observable at the target color is enhanced relative to reflected white light without emission from the first and second color emitters.

196. The display of claim 195, wherein the first target color and the second target color are the same.

197. The display of claim 195, wherein the first target color and the second target color are different.

198. The display of claim 195, wherein at least one of the first and second color emitters comprises light emitting particles having a diameter less than about 1000 nanometers.

199. The display of claim 198, wherein a mixture of the first and second color emitters comprises at least one of red, blue, and green emitters configured to produce red, blue, and green emissions from an up conversion process.

200. The display of claim 195, wherein a mixture of the first and second color emitters comprises a component of a color emitting pixel element of the display.

201. The display of claim 195, wherein a mixture of the first and second color emitters comprises a component of a color filter of the display.

202. The display of claim 195, wherein a mixture of the first and second color emitters comprises a component of a color filter for a display of the display.

203. The display of claim 195, wherein a mixture of the first and second color emitters comprises a component of a color surface of the display.

204. The display of claim 195, wherein a mixture of the first and second color emitters comprises a component of a color reflective surface in a pixel of the display.

205. The display of claim 195, wherein a mixture of the first and second color emitters comprises a component of a white-light emitting pixel display element of the display.

206. The display of claim 195, wherein a mixture of the first and second color emitters comprises at least one of red, blue, and green emitters configured to produce red, blue, and green emissions from a down conversion process.

207. The display of claim 195, wherein mixtures of the first and second color emitters comprises at least one of red, blue, and green emitters configured to produce red, blue, and green emissions from a down conversion process.

208. The display of claim 195, wherein a mixture of the first and second color emitters comprises at least one of red, blue, and green emitters configured to produce red, blue, and green emissions from a mixture of up converters and down converters.

209. The display of claim 195, wherein mixtures of the first and second color emitters comprises at least one of red, blue, and green emitters configured to produce red, blue, and green emissions from mixtures of up converters and down converters.

210. The display of claim 195, wherein a mixture of the first and second color emitters comprises a mixture of fluorescent emitters including at least one of europium, terbium, cerium, and erbium or combinations thereof.

211. The display of claim 195, wherein mixtures of the first and second color emitters comprise mixtures of fluorescent emitters including at least one of europium, terbium, cerium, and erbium or combinations thereof.

212. The display of claim 211, further comprising a third material configured to emit a third visible color in response to absorption of the ultraviolet light, wherein the third visible color is different from the first visible color and the second visible color.

213. The display of claim 212, wherein the first visible color, the second visible color, and the third visible color are primary colors.

214. The display of claim 212, further comprising a third material configured to emit a third visible color in response to absorption of the infrared light, wherein the third visible color is different from the first visible color and the second visible color.

215. The display of claim 213, further comprising a third material configured to emit a third visible color in response to absorption of the ultraviolet light, wherein the third visible color is different from the first visible color and the second visible color.

216. The display of claim 213, further comprising a third material configured to emit a third visible color in response to absorption of the infrared light, wherein the third visible color is different from the first visible color and the second visible color.

217. The display of claim 216, wherein the first visible color, the second visible color, and the third visible color are at least two of the primary colors.

218. The display of claim 195, wherein said metallic structure comprises at least one of Au, Ag, Cu, Ni, Pt, Pd, Co, Ru, Rh, Al, Ga, or a combination or alloys or layers thereof.

219. The display of claim 195, wherein the nanoparticle emitter comprises at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

220. The display of claim 219, wherein the nanoparticle comprises a dopant including at least one of Er, Eu, Yb, Tm, Nd, Tb, Ce, Y, U, Pr, La, Gd and other rare-earth species or a combination thereof.

221. The display of claim 220, wherein the dopant is included at a concentration of 0.01%-50% by mol concentration.

222. The display of claim 195, wherein at least one of the first and second color emitters comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS: Mn,$Er^{3+}$.

223. The display of claim 195, wherein at least one of the first and second color emitters comprises a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

224. The display of claim 223, wherein the dielectric up converter has a diameter ranging from at least one of 2-1000 nm, 2-100 nm, 2-50 nm, 2-20 nm, or 2-10 nm.

225. The display of claim 223, wherein:
the dielectric up converter comprises a dopant including at least one of Er, Eu, Yb, Tm, Nd, Tb, Ce, Y, U, Pr, La, Gd and other rare-earth species or a combination thereof; and
the dopant has a concentration of 0.01%-50% by mol concentration.

226. The display of claim 223, further comprising a metallic structure disposed in relation to the dielectric up converter, and the metallic structure includes at least one of Au, Ag, Cu, Ni, Pt, Pd, Co, Ru, Rh, Al, Ga, or alloys or layers thereof.

227. The display of claim 223, wherein the dielectric up converter is configured to exhibit visible emission upon interaction with NIR light.

228. The display of claim 195, wherein at least one of the first and second color emitters comprise an upconverter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$: $Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4-dimethyl-2,2-bipyridine).

229. A light display comprising:
at least one of a color filter or a color reflective surface;
color emitters included in the color filter or the color reflective surface, and including,
first color emitters configured to emit, upon exposure to a light source, visible light at a target color in response to absorption of energy across a first band of wavelengths, and
second color emitters configured to emit, upon exposure to the light source, visible light at the target color in response to absorption of energy across a second band of wavelengths,
wherein at least one of the first and second color emitters comprises:
(i) a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof, or
(ii) an upconverter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$: $Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including $[Ru(dmb)_3]^{2+}$ (dmb=4,4'-dimethyl-2,2'-bipyridine),
wherein light intensity observable at the target color is enhanced relative to reflected white light without emission from the first and second color emitters.

230. The display of claim 229, wherein the first target color and the second target color are the same.

231. The display of claim 229, wherein the first target color and the second target color are different.

232. The display of claim 229, wherein at least one of the first and second color emitters comprises light emitting particles having a diameter less than about 1000 nanometers.

233. The display of claim 232, wherein a mixture of the first and second color emitters comprises at least one of red, blue, and green emitters configured to produce red, blue, and green emissions from an up conversion process.

234. The display of claim 229, wherein a mixture of the first and second color emitters comprises a component of a color emitting pixel element of the display.

235. The display of claim 229, wherein a mixture of the first and second color emitters comprises a component of a color filter of the display.

236. The display of claim 229, wherein a mixture of the first and second color emitters comprises a component of a color filter for a display of the display.

237. The display of claim 229, wherein a mixture of the first and second color emitters comprises a component of a color surface of the display.

238. The display of claim 229, wherein a mixture of the first and second color emitters comprises a component of a color reflective surface in a pixel of the display.

239. The display of claim 229, wherein a mixture of the first and second color emitters comprises a component of a white-light emitting pixel display element of the display.

240. The display of claim 229, wherein a mixture of the first and second color emitters comprises at least one of red, blue, and green emitters configured to produce red, blue, and green emissions from a down conversion process.

241. The display of claim 229, wherein mixtures of the first and second color emitters comprises at least one of red, blue, and green emitters configured to produce red, blue, and green emissions from a down conversion process.

242. The display of claim 229, wherein a mixture of the first and second color emitters comprises at least one of red, blue, and green emitters configured to produce red, blue, and green emissions from a mixture of up converters and down converters.

243. The display of claim 229, wherein mixtures of the first and second color emitters comprises at least one of red, blue, and green emitters configured to produce red, blue, and green emissions from mixtures of up converters and down converters.

244. The display of claim 229, wherein a mixture of the first and second color emitters comprises a mixture of fluorescent emitters including at least one of europium, terbium, cerium, and erbium or combinations thereof.

245. The display of claim 229, wherein mixtures of the first and second color emitters comprise mixtures of fluorescent emitters including at least one of europium, terbium, cerium, and erbium or combinations thereof.

246. The display of claim 245, further comprising a third material configured to emit a third visible color in response to absorption of the ultraviolet light, wherein the third visible color is different from the first visible color and the second visible color.

247. The display of claim 246, wherein the first visible color, the second visible color, and the third visible color are primary colors.

248. The display of claim 247, further comprising a third material configured to emit a third visible color in response to absorption of the infrared light, wherein the third visible color is different from the first visible color and the second visible color.

249. The display of claim 247, further comprising a third material configured to emit a third visible color in response to absorption of the ultraviolet light, wherein the third visible color is different from the first visible color and the second visible color.

250. The display of claim 247, further comprising a third material configured to emit a third visible color in response to absorption of the infrared light, wherein the third visible color is different from the first visible color and the second visible color.

251. The display of claim 250, wherein the first visible color, the second visible color, and the third visible color are at least two of the primary colors.

252. The display of claim 229, wherein at least one of the first and second color emitters comprises a down converter including at least one of $Y_2O_3$; ZnS; ZnSe; MgS; CaS; Mn, Er ZnSe; Mn, Er MgS; Mn, Er CaS; Mn, Er ZnS; Mn,Yb ZnSe; Mn,Yb MgS; Mn, Yb CaS; Mn,Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn,$Er^{3+}$.

253. The display of claim 229, wherein at least one of the first and second color emitters comprises a dielectric up converter including at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, or $SiO_2$ or alloys or layers thereof.

254. The display of claim 253, wherein the dielectric up converter has a diameter ranging from at least one of 2-1000 nm, 2-100 nm, 2-50 nm, 2-20 nm, or 2-10 nm.

255. The display of claim 253, wherein:
the dielectric up converter comprises a dopant including at least one of Er, Eu, Yb, Tm, Nd, Tb, Ce, Y, U, Pr, La, Gd and other rare-earth species or a combination thereof; and
the dopant has a concentration of 0.01%-50% by mol concentration.

256. The display of claim 253, further comprising a metallic structure disposed in relation to the dielectric up converter, and the metallic structure includes at least one of Au, Ag, Cu, Ni, Pt, Pd, Co, Ru, Rh, Al, Ga, or alloys or layers thereof.

257. The display of claim 253, wherein the dielectric up converter is configured to exhibit visible emission upon interaction with NIR light.

258. The display of claim 229, wherein at least one of the first and second color emitters comprise an upconverter including at least one of $Tm^{3+}$ doped flourozirconate glasses, $LuPO_4$:$Yb^{3+}$, $Tm^{3+}$, and $YbPO_4$:$Er^{3+}$ nanocrystals, tellurium and germanium oxides, tellurium and germanium oxides doped with at least one Tm, Yb, Ho, Er, or Pr, $Yb^{3+}$ doped $BaZrO_3$, $Nd^{3+}$:$Cs_2NaGdCl_6$, $Nd^{3+}$, $Yb^{3+}$:$Cs_2NaGdCl_6$, $Nd^{3+}$ and $Ho^{3+}$ co-doped-based $ZrF_4$ fluoride glasses, $Tm^{3+}$/$Yb^{3+}$-codoped $TeO_2$—$Ga_2O_3$—$R_2O$ (R=Li, Na, K) glasses, and metal-to-ligand charge transfer (MLCT) transition materials, and MLCT transition materials including [Ru(dmb)$_3$]$^{2+}$ (dmb=4,4-dimethyl-2,2-bipyridine).

* * * * *